US007368236B2

(12) United States Patent
Gold et al.

(10) Patent No.: US 7,368,236 B2
(45) Date of Patent: *May 6, 2008

(54) METHODS OF PRODUCING NUCLEIC ACID LIGANDS

(75) Inventors: Larry Gold, Boulder, CO (US); Craig Tuerk, Boulder, CO (US)

(73) Assignee: Gilead Sciences, Inc., Foster City, CA (US)

( * ) Notice: Subject to any disclaimer, the term of this patent is extended or adjusted under 35 U.S.C. 154(b) by 495 days.

This patent is subject to a terminal disclaimer.

(21) Appl. No.: 10/818,954

(22) Filed: Apr. 6, 2004

(65) Prior Publication Data

US 2004/0241731 A1    Dec. 2, 2004

Related U.S. Application Data

(60) Continuation of application No. 10/040,497, filed on Jan. 7, 2002, now Pat. No. 6,716,583, which is a continuation of application No. 09/165,616, filed on Oct. 2, 1998, now Pat. No. 6,334,318, which is a continuation of application No. 08/748,697, filed on Nov. 13, 1996, now Pat. No. 5,817,785, which is a continuation of application No. 08/442,062, filed on May 16, 1995, now Pat. No. 5,595,877, which is a division of application No. 07/964,624, filed on Oct. 21, 1992, now Pat. No. 5,496,938, which is a continuation-in-part of application No. 07/714,131, filed on Jun. 10, 1991, now Pat. No. 5,475,096, which is a continuation-in-part of application No. 07/536,428, filed on Jun. 11, 1990, now abandoned.

(51) Int. Cl.
*C12Q 1/68* (2006.01)
*C12P 19/34* (2006.01)
*G01N 33/566* (2006.01)
*C07H 21/04* (2006.01)
*C07H 21/00* (2006.01)

(52) U.S. Cl. .................. 435/6; 435/91.2; 436/501; 536/23.1; 536/25.3

(58) Field of Classification Search ..................... None
See application file for complete search history.

(56) References Cited

U.S. PATENT DOCUMENTS

| | | |
|---|---|---|
| 5,223,409 A | 6/1993 | Ladner et al. |
| 5,270,163 A | 12/1993 | Gold et al. |
| 5,527,894 A | 6/1996 | Gold et al. |
| 5,595,877 A | 1/1997 | Gold et al. |
| 5,817,785 A | 10/1998 | Gold et al. |
| 5,958,691 A | 9/1999 | Pieken et al. |

FOREIGN PATENT DOCUMENTS

GB    2 183 661 A    6/1987

| | | | |
|---|---|---|---|
| WO | WO 88/09810 A1 | * | 12/1988 |
| WO | WO 89/06694 | | 7/1989 |
| WO | WO 91/19813 | | 12/1991 |
| WO | WO 92/14843 | | 9/1992 |
| WO | WO 93/04204 | | 3/1993 |

OTHER PUBLICATIONS

Bartel et al. (1991) Cell 67:529.
Bass and Cech (1984) Nature 308:820.
Bock et al. (1992) Nature 355:564.
Carey et al. (1983) Biochemistry 22:2601.
Ellington & Szostak (1990) Absract of papers presented at the 1990 meeting on RNA Processing, Cold Springs Harbor Laboratory, Cold Spring Harbor, NY, p. 84.
Joyce (1989) Gene 82:83.
Joyce and Inoue (1989) Nucleic Acid Research 17:711.
Kacian et al. (1972) PNAS USA 69:3038.
Kinzler and Vogelstein (1989) Nuc. Acids. Res. 17:3645.
Kramer et al. (1974) J. Mol. Biol. 89:719.
Levisohn and Spiegelman (1969) PNAS USA 63:805.
Levisohn and Spiegelman (1968) PNAS USA 60:866.
Milligan et al. (1993) Journal of Medicinal Chemistry 36(14):1923.
Mills et al. (1973) Science 180:916.
Mills et al. (1967) PNAS USA 58:217.
Oliphant et al. (1989) Mol. Cell Biol. 9:2944.
Oliphant and Struhl (1988) Nucleid Acid Research 16:7673.
Oliphant et al. (1986) Gene 44:177.
Oliphant and Struhl (1987) Methods in Enzymology 155:568.
Rich et al. (1984) Ann Rev. Biochem. 53:791.
Robertson and Joyce (1990) Nature 344:467.
Romaniuk et al. (1987) Biochemistry 26:1563.
Schimmel (1989) Cell 59:9.
Saffhill et al. (1970) J. Mol. Biol. 51:531.
Szostak, "Structure and Activity of Ribozymes" in Reading the Molecules of Life, (S.A. Benner ed.) Springer-Verlag Berlin Heidelbeg, pp. 87-113, (1988).
Thiesen and Bach (1990) Nucleic Acid Research 18:3203.
Tuerk et al. (1988) Proc. Natl. Acad. Sci. USA 85:1364.
Tuerk and Gold (1990) Science 249:505.
Uhlenbeck et al. (1983) J. Biomol. Structure and Dynamics 1:539.
Witherell and Uhlenbeck (1989) Biochemistry 28:71.
Yarus (1988) Science 240:1751.
Uhlmann et al, (1990) Chemical Reviews 90:544-584.
Martin, (1992) Journal of Medicinal Chemistry 35:2145-2154.
Ostendorf and Floege (1999) *Medizinische Klinik* 94(4):219-23, Aptamere: ein neuer Ansatz für Interventionsstudien und zur Entwicklung zukünftiger Therapieansätze, abstract only.

* cited by examiner

*Primary Examiner*—Tracy Vivlemore
(74) *Attorney, Agent, or Firm*—Swanson & Bratschun, L.L.C.

(57) ABSTRACT

The present invention includes methods for the identification and production of improved nucleic acid ligands based on the SELEX process. Also included are nucleic acid ligands to the HIV-RT protein identified according to the methods described therein.

56 Claims, 32 Drawing Sheets

● : denotes a 2' O-methyl instead of an OH, denoted by (O), at this position on the ribose

```
5'-GGUCCGAAGUGCAACGGGAAAAUGCACU-[30N]-
              CUAUGAAAGAAUUUUAUAUCUCUAUUGAAAC-3'
                     SEQ ID NO.:37
```

| Isolate number | Sequence | SEQ ID NO: |
|---|---|---|
| 3,22,29 | uAGCUCGUGAGGCUUU—CGUGCUGUUCGAGcuau | 14 |
| 14 | uGCAUGUGAGGCGGU—AACGCUGUUCGGUGCu | 15 |
| 20 | uGGUGAUGAGGCCG——AUGCUGUUCGUCGCCGcu | 16 |
| 4 | uGACGCGCGAGGUCUU—GGUACUGUUCGGUGGCUcu | 17 |
| 30 | uCUGGGUGAGACUUG——AAGUCGUUCGCCAGGUcu | 18 |
| 38 | uCCCGGUGAAGCAUA——AUGCUGUUCGUGGGGUcu | 19 |
| 39 | uGGGAGUGAGGUU————CCCCGUUCGUCCCGCACCcu | 20 |
| 2,6,9 | uAGCGAUGUGAAGUGA————UACUGGUCGAUCGUGcu | 21 |
| 13,26 | uCACAGUGAGCCUU——CUGGUGGUCGUGUGUGcu | 22 |
| 7 | uUGUUGUGAGUGGUUGAUUCCAUGGUCGAACcu | 23 |
| 35 | uGCCUGUGAGCUGU——UUAGCGGUCGAGGUCGUcu | 24 |
| 24 | uCAAGCCGAAGACUU——AGUCUGCUCGCUGUGcu | 25 |
| 8 | uUGCGUCGAAGUUAA——UUCUGGUCGAUGCCAcu | 26 |
| 40 | uUUCAAUGAGGUAUG-UAAUGAUGGUCGUGCGCcu | 27 |
| 1 | uGCGGGAGAGUCUU————UUGACGUUGCUCCUGCGcu | 28 |
| 17 | uCAUGGGAGCCCAUCGA-UUCUGGGUGUUGCCuauga | 29 |
| 23,27 | uUGCACAGAGCCAAA————UUUGGUGUUGCUGUGcu | 30 |
| 18,34 | uGGCCAGAGCUUAAA——UUCAAGUGUUGCUGGCcu | 31 |
| 19 | uCAUAGCAGUCCUUGAUACUAUGGAUGGUGGcuauga | 32 |
| 37 | uGGAUGCAAGUUAA——CUCUGGUGGCAUCCGUCcu | 33 |
| 31 | uCAGUGGAGAUUAAGCCUCGCUAGGGGCCGcuau | 34 |

FIG. 9

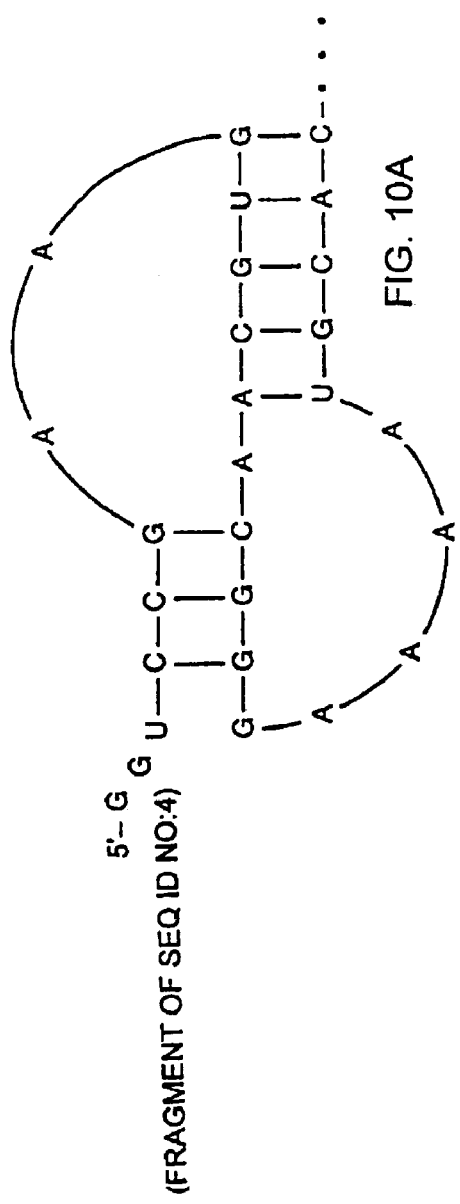
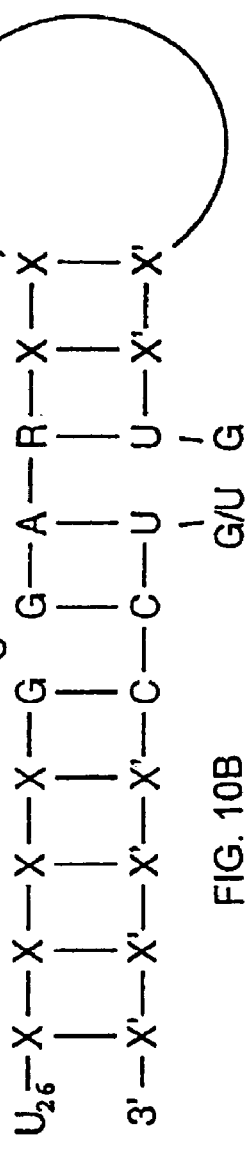
FIG. 10A (FRAGMENT OF SEQ ID NO:4)
FIG. 10B (SEQ ID NO:38)
FIG. 10C (SEQ ID NO:39)

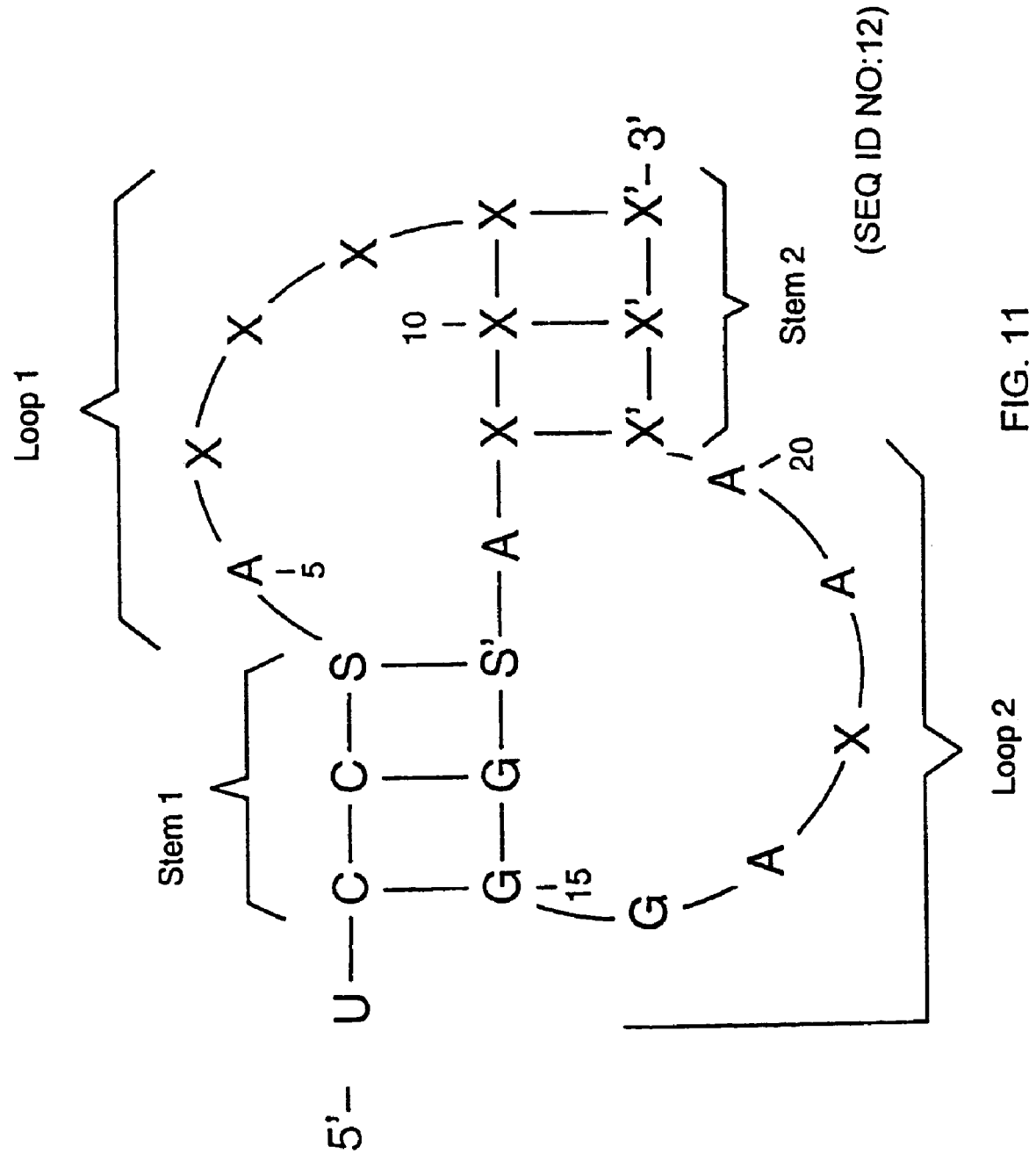
FIG. 11 (SEQ ID NO:12)

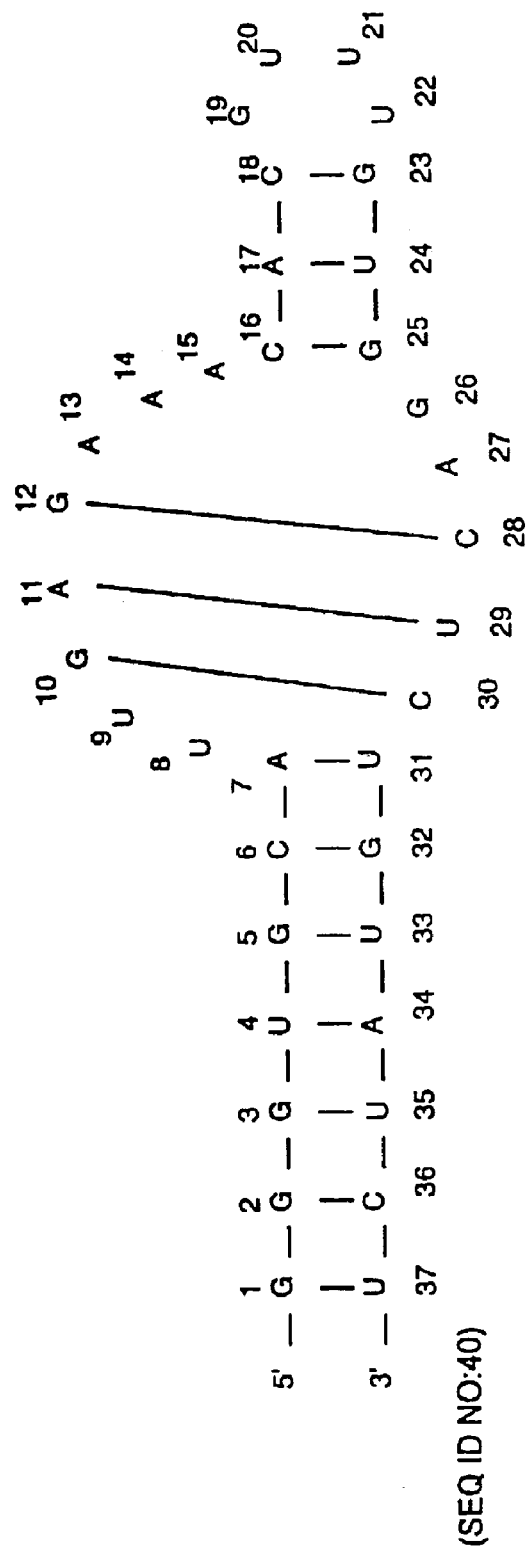
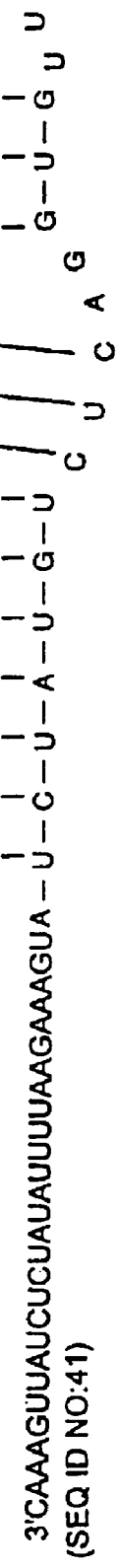
FIG. 12A
FIG. 12B
FIG. 12C
(SEQ ID NO:40)
3' CAAAGUUAUCUCUAUAUAUUUUAAGAAAGUA 5'
(SEQ ID NO:41)
(SEQ ID NO:42)  5' GTTTCAATAGAGATATAAAATTC 3'

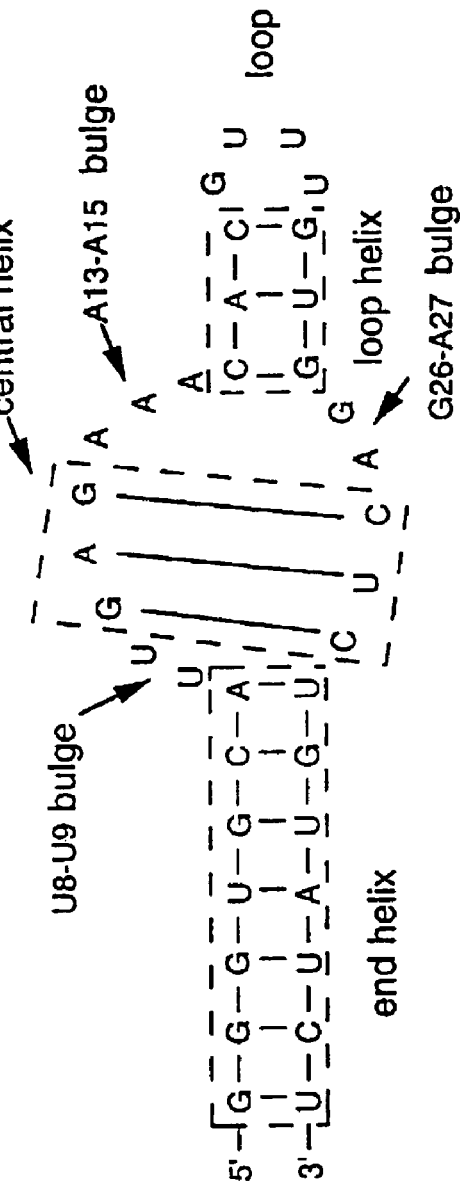

(SEQ ID NO:40)

(SEQ ID NO:40)

(SEQ ID NO:40)

(SEQ ID NO:40)

(SEQ ID NO:40)

SEQ ID NO.:43

5'-GGGACUAUUGAUGGCCUUCCGACC-6a-CACACAGAGGUAAAGAGGAUCCGGG-3'

| Biased ligand sequences | | SEQ ID NO.: |
|---|---|---|
| 6a | GGGUGCAUUGAGAAACACGU-UUGUGGACUCUGUAUCU | 40 |
| 1 | UGGUGCGUUGAGAAACAGGU-UUUUGGACUCCGUACCa | 45 |
| 2 | GUAUGCAUUGAGAGUCACAC-UUGUGGACUCUGCAUCC | 46 |
| 3 | AGAUGGAUUGAGAAACACUA-UUAUGGACUCUCCAUCG | 47 |
| 4 | AGCUUCGUCGAGAUACACGU-UGAUGGACUCCGAAGCA | 48 |
| 5 | UCGUACGUUGAGAAACAAGU-UUAUGGACUCCGUACCU | 49 |
| 6 | UCGAUCGUUGAGAUACACGC-UAGUGGACUCCGAAACU | 50 |
| 8 | UACUGCAUCGAGAUACACGU-UUGUGGACUCUGCACAU | 51 |
| 9 | UGAUACGUUGAGAAACACAA-UGCUGGACUCCGCAUCC | 52 |
| 10 | GCCUGCAUUGAGAAACAGGA-UUCUGGACUCUGCCACU | 53 |
| 12 | CGCUAUGUUGAAACACUU-UGCUGGACUCCGUAGCU | 54 |
| 13 | UACUGCAUCGAGAAACACGU-AAGUG-ACUCUGCAUCC | 55 |
| 15 | CGGUACGUCGAGAUACACGA-AGAUGGACUCCGUAUCG | 56 |

FIG. 21-A

| | | SEQ ID NO. |
|---|---|---|
| 17 | AACUCCAUCGAGAAACACGA-UAGUGGACUCUGGAGCU | 57 |
| 18 | GGAGACGUCGAGAAACACGU-UUGUGGACUCCGUCUCU | 58 |
| 21 | AGCUACAUCGAGAAACAAGA-UUUUGGACUCUGUAGCG | 59 |
| 23 | AAGUGCAUUGAGAUACAAAU-GAUGGACUCUGGAGCU | 60 |
| 24 | UGCUACGUUGAGAUACACGU-UGAUGCACUCCGUAGCU | 61 |
| 25 | AGCUACGUUGAGADACACGUUACGUGG-CUCCGUAGCC | 62 |
| 27 | GAGUGGCUCGAGAAACAGGU-UGCUGGACUCGCCACAU | 63 |
| 28 | UCGUGCGUCGAGCAACACGU-UGAUGGACUCCGCACAG | 64 |
| 29 | GGCACCGUUGAGAAACACAU-GCGUGGACUCCGUGCCC | 65 |
| 30 | UCCUGCAUUGAGAAACAGUG-AUCUGGACUCUGCAACU | 66 |
| 31 | CUGUGGAUUGAGCAACACGU-GAGUGGACUCUCCACAU | 67 |
| 32 | CCGUGCGUUGAGACACACAC-CGAUGGACUCCGCAUGU | 68 |
| 33 | AGCUGCAUCGAGAUACACGA-UUUGUGGACUCUGCAGCC | 69 |
| 35 | AGAUUCGUUGAGAAACACAU-GGGUGGACUCUCCGCUA | 70 |
| 36 | AGAUGGAUUGAGAAACACGU-UCGUGGACUCUCCAACU | 71 |
| 37 | GACUGCAUCGAGAAACACUG-AUGUGGCCUCCGCACGG | 72 |

FIG. 21-B

| | | SEQ ID NO.: |
|---|---|---|
| 38 | AGCUACGUUGAGAAACAGUA-UAAUGGACUCCGUAGCU | 73 |
| 40 | GAGUGCGUCGAGAAACACAU-UUGUGGACUCCGCACAC | 74 |
| 42 | UCGUACGUUGAGAAACACGC-UAGUGGACUCCGUAUGU | 75 |
| 43 | AGAUACGUUGAGAGACACGC-ACGUGGACUCCGUAUCU | 76 |
| 44 | AGGAUCACAGAGAAACACGUGGGUGG-CUCCCUCUAU | 77 |
| 45 | GUGCGCAUCGAGAAACACGU-UGAUGGACUCUCGCAUGCAC | 78 |
| 47 | GAGAGGAUCGAGAAACACGU-AUGUGGACUCUCCAUCU | 79 |
| 48 | GGAUGGAUUGAGACACACGU-AUGUGGACUCUCCAUCA | 80 |
| 49 | UCGGGCAUUGAGAAACACGU-AGAUGGACUCUCUCA | 81 |
| 50 | UGGACCGUAGAGAAACACGUUUGAUGG-CUCCCUCUGU | 82 |

FIG. 21-C

| 6a | G1/U37 | G2/C36 | G3/U35 | U4/A34 | G5/U33 | C6/G32 | A7/U31 | C16/G25 | A17/U24 | C18/G23 | G19/U22 |
|---|---|---|---|---|---|---|---|---|---|---|---|
| WT | 2 | 16 | 8 | 28 | 2 | 28 | 16 | 38 | 38 | 19 | 9 |
| AU | 6 | 0 | 6 | 0 | 10 | 0 | 16 | 0 | 38 | 0 | 2 |
| UA | 2 | 1 | 0 | 28 | 2 | 0 | 0 | 0 | 0 | 2 | 1 |
| GC | 5 | 16 | 7 | 2 | 18 | 6 | 18 | 0 | 0 | 3 | 3 |
| CG | 1 | 2 | 8 | 0 | 1 | 28 | 1 | 38 | 0 | 19 | 1 |
| GU | 1 | 1 | 8 | 0 | 2 | 0 | 1 | 0 | 0 | 1 | 9 |
| UG | 4 | 1 | 0 | 2 | 0 | 1 | 0 | 0 | 0 | 0 | 0 |
| AC | 3 | 3 | 0 | 0 | 1 | 0 | 2 | 0 | 0 | 0 | 1 |
| CA | 1 | 1 | 2 | 0 | 0 | 0 | 0 | 0 | 0 | 9 | 0 |
| other | 16 | 13 | 7 | 8 | 2 | 3 | 0 | 0 | 0 | 4 | 14 |

FIG. 23A

| 6a | G1/U37 | G2/C36 | G3/U35 | U4/A34 | G5/U33 | C6/G32 | A7/U31 | C16/G25 | A17/U24 | C18/G23 | G19/U22 |
|---|---|---|---|---|---|---|---|---|---|---|---|
| WT | .05 | .42 | .21 | .74 | .05 | .74 | .42 | 1.00 | 1.00 | .50 | .24 |
| AU | .16 | .00 | .16 | .00 | .26 | .00 | .42 | .00 | 1.00 | .00 | .05 |
| UA | .05 | .03 | .00 | .74 | .05 | .00 | .00 | .00 | .00 | .05 | .03 |
| GC | .13 | .42 | .18 | .05 | .47 | .16 | .47 | .00 | .00 | .08 | .08 |
| CG | .03 | .05 | .21 | .00 | .03 | .74 | .03 | 1.00 | .00 | .50 | .03 |
| GU | .03 | .03 | .21 | .00 | .05 | .00 | .03 | .00 | .00 | .03 | .24 |
| UG | .11 | .03 | .00 | .05 | .00 | .03 | .00 | .00 | .00 | .00 | .03 |
| AC | .08 | .08 | .05 | .00 | .03 | .00 | .05 | .00 | .00 | .00 | .03 |
| CA | .03 | .03 | .18 | .00 | .00 | .00 | .00 | .00 | .00 | .24 | .00 |
| other | .42 | .34 | .18 | .21 | .05 | .08 | .00 | .00 | .00 | .11 | .37 |

FIG. 23B

| 6a | G1/U37 | G2/C36 | G3/U35 | U4/A34 | G5/U33 | C6/G32 | A7/U31 | | C16/G25 | A17/U24 | C18/G23 | G19/U22 |
|---|---|---|---|---|---|---|---|---|---|---|---|---|
| WT | -.34 | .03 | -.18 | .35 | -.34 | .35 | .03 | | .61 | .61 | .11 | -.15 |
| AU | .08 | -.02 | .08 | -.02 | .19 | -.02 | .03 | | -.02 | .61 | -.02 | -.03 |
| UA | .04 | .01 | -.02 | .35 | .04 | -.02 | -.02 | | -.02 | -.02 | .04 | .01 |
| GC | .05 | .03 | .11 | .04 | .40 | .14 | .46 | | -.02 | -.02 | .06 | .00 |
| CG | .01 | .04 | .19 | -.02 | .01 | .35 | .01 | | .61 | -.02 | .11 | .01 |
| GU | -.34 | -.05 | -.18 | -.02 | -.34 | -.02 | -.05 | | -.02 | -.08 | .01 | -.15 |
| UG | .09 | .01 | -.02 | -.08 | -.02 | -.05 | -.02 | | -.08 | -.02 | -.08 | -.02 |
| AC | .06 | .00 | -.02 | .04 | .01 | -.02 | -.03 | | -.02 | -.08 | -.02 | .01 |
| CA | .01 | .01 | .04 | -.08 | -.02 | -.08 | -.02 | | -.08 | -.02 | .16 | -.02 |
| other | .17 | .09 | -.07 | -.04 | -.20 | -.17 | -.25 | | -.25 | -.25 | -.15 | .12 |

FIG. 23C

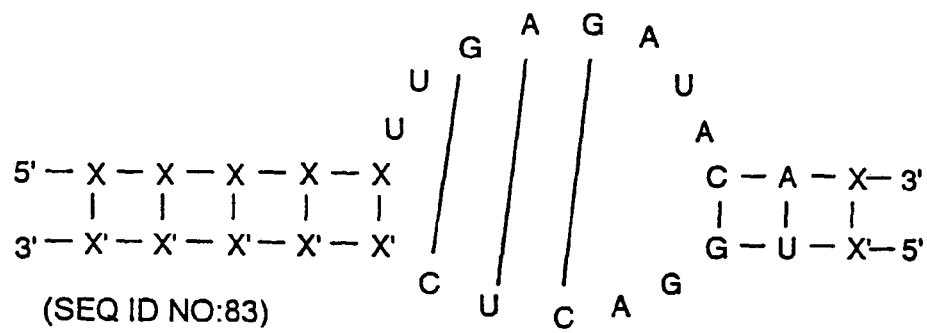
FIG. 24A (SEQ ID NO:83)
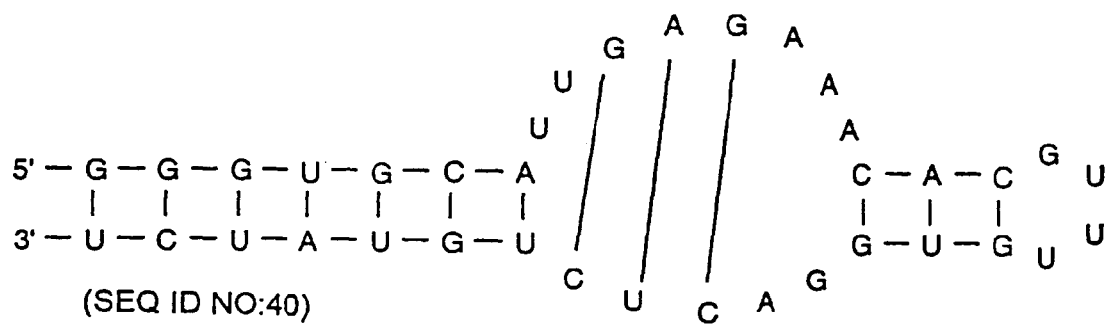
FIG. 24B (SEQ ID NO:40)
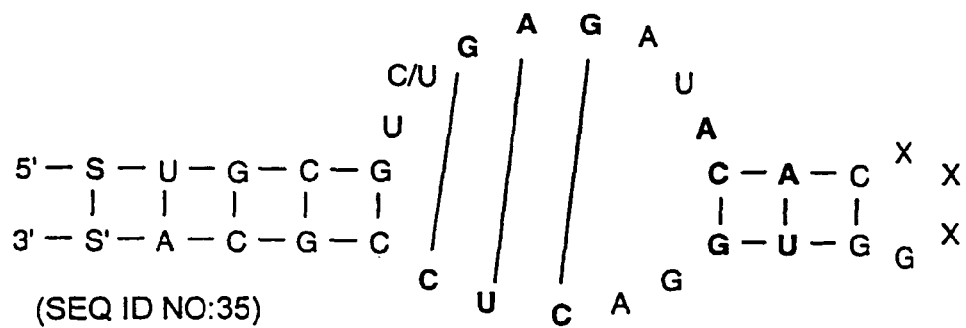
FIG. 24C (SEQ ID NO:35)

SEQUENCE LISTING (1) GENERAL INFORMATION:

(iii) NUMBER OF SEQUENCES: 83

(2) INFORMATION FOR SEQ ID NO: 1:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (xi) SEQUENCE DESCRIPTION: SEQ ID NO: 1:

UUCCGNNNNN NNNCGGGAAA A                                              21

(2) INFORMATION FOR SEQ ID NO: 2:

(i) SEQUENCE CHARACTERISTICS:
          (A) LENGTH: 24 base pairs
          (B) TYPE: nucleic acid
          (C) STRANDEDNESS: single
          (D) TOPOLOGY: linear (xi) SEQUENCE DESCRIPTION: SEQ ID NO: 2:

UCCGNNNNNN NNCGGGAAAA NNNN                                           24

(2) INFORMATION FOR SEQ ID NO: 3:

(i) SEQUENCE CHARACTERISTICS:
          (A) LENGTH: 27 base pairs
          (B) TYPE: nucleic acid
          (C) STRANDEDNESS: single
          (D) TOPOLOGY: linear (xi) SEQUENCE DESCRIPTION: SEQ ID NO: 3:

NNUUCCGNNN NNNNNCGGGA AAANNNN                                        27

(2) INFORMATION FOR SEQ ID NO: 4:

(i) SEQUENCE CHARACTERISTICS:
          (A) LENGTH: 57 base pairs
          (B) TYPE: nucleic acid
          (C) STRANDEDNESS: single
          (D) TOPOLOGY: linear (xi) SEQUENCE DESCRIPTION: SEQ ID NO: 4:

GGUCCGAAGU GCAACGGGAA AAUGCACUAU GAAAGAAUUU UAUAUCUCUA               50

UUGAAAC                                                              57

(2) INFORMATION FOR SEQ ID NO: 5:

(i) SEQUENCE CHARACTERISTICS:
          (A) LENGTH: 31 base pairs
          (B) TYPE: nucleic acid
          (C) STRANDEDNESS: single
          (D) TOPOLOGY: linear (xi) SEQUENCE DESCRIPTION: SEQ ID NO: 5:

CCGGATCCGT TCAATAGAG ATATAAAATT C                                    31

(2) INFORMATION FOR SEQ ID NO: 6:

(i) SEQUENCE CHARACTERISTICS:
          (A) LENGTH: 55 base pairs

```
            (B) TYPE: nucleic acid
            (C) STRANDEDNESS: single
            (D) TOPOLOGY: linear (xi) SEQUENCE DESCRIPTION: SEQ ID NO: 6:

GGGCAAGCTT TAATACGACT CACTATAGGT CCGAAGTGCA ACGGGAAAAT        50

GCACT                                                        55

(2) INFORMATION FOR SEQ ID NO: 7:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (xi) SEQUENCE DESCRIPTION: SEQ ID NO: 7:

GTTTCAATAG AGATATAAAA TTCTTTCATA G                            31

(2) INFORMATION FOR SEQ ID NO: 8:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (xi) SEQUENCE DESCRIPTION: SEQ ID NO: 8:

GTTTCAATAG AGATATAAAA TTCTTTCATA GNNNNNNNNN NNNNNNNNNN        50

NNNNNNNNNN NAGTGCATTT TCCCGTTGCA CTTCGGACC                    89

(2) INFORMATION FOR SEQ ID NO: 9:

(i) SEQUENCE CHARACTERISTICS:
            (A) LENGTH: 85 base pairs
            (B) TYPE: nucleic acid
            (C) STRANDEDNESS: single
            (D) TOPOLOGY: linear (xi) SEQUENCE DESCRIPTION: SEQ ID NO: 9:

CCCGGATCCT CTTTACCTCT GTGTGAGATA CAGAGTCCAC AAACGTGTTC        50

TCAATGCACC CGGTCGGAAG GCCATCAATA GTCCC                        85

(2) INFORMATION FOR SEQ ID NO: 10:

(i) SEQUENCE CHARACTERISTICS:
            (A) LENGTH: 49 base pairs
            (B) TYPE: nucleic acid
            (C) STRANDEDNESS: single
            (D) TOPOLOGY: linear (xi) SEQUENCE DESCRIPTION: SEQ ID NO: 10:

CCGAAGCTTA ATACGACTCA CTATAGGGAC TATTGATGGC CTTCCGACC         49

(2) INFORMATION FOR SEQ ID NO: 11:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO: 11:

CCCGGATCCT CTTTACCTCT GTGTG                                   25
```

(2) INFORMATION FOR SEQ ID NO: 12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ix) FEATURE:
        (D) OTHER INFORMATION: N's at positions 9-1
            paired with N's at positions 21-23

(xi) SEQUENCE DESCRIPTION: SEQ ID NO: 12:

UCCSANNNNN NASGGGANAA NNN                                            23

(2) INFORMATION FOR SEQ ID NO: 13:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION: N at position 29-36
            variable length of 6-8 bases (xi) SEQUENCE DESCRIPTION: SEQ ID NO: 13:

GGUCCGAAGU GCAACGGGGA AAAUGCACNN NNNNNNNNNN NNNNNNNNNN          50

NNNNNNNNNN NNNNNN                                                    66

(2) INFORMATION FOR SEQ ID NO: 14:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 14:

GGUCCGAAGU GCAACGGGAA AAUGCACUAG CUCGUGAGGC UUUCGUGCUG          50

UUCCGAGCUA UGAAAGAAUU UUAUAUCUCU AUUGAAAC                       88

(2) INFORMATION FOR SEQ ID NO: 15:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 15:

GGUCCGAAGU GCAACGGGAA AAUGCACUGC AUGUGAGGCG GUAACGCUGU          50

UCCGUGCUAU GAAAGAAUUU UAUAUCUCUA UUGAAAC                        87

(2) INFORMATION FOR SEQ ID NO: 16:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 16:

-continued

```
GGUCCGAAGU GCAACGGGAA AAUGCACUGG UGAGUGAGGC CGAUGCUGUU          50

CCUCGCCGCU AUGAAAGAAU UUUAUAUCUC UAUUGAAAC                     89
```

(2) INFORMATION FOR SEQ ID NO: 17:

(i) SEQUENCE CHARACTERISTICS:
        (A) LENGTH: 91 base pairs
        (B) TYPE: nucleic acid
        (C) STRANDEDNESS: single
        (D) TOPOLOGY: linear (xi) SEQUENCE DESCRIPTION: SEQ ID NO: 17:

```
GGUCCGAAGU GCAACGGGAA AAUGCACUGA CGCGCGAGGU CUUGGUACUG          50

UUCCGUGGCU CUAUGAAAGA AUUUUAUAUC UCUAUUGAAA C                  91
```

(2) INFORMATION FOR SEQ ID NO: 18:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 18:

```
GGUCCGAAGU GCAACGGGAA AAUGCACUCU GGGUGAGACU UGAAGUCGUU          50

CCCCAGGUCU AUGAAAGAAU UUUAUAUCUC UAUUGAAAC                     89
```

(2) INFORMATION FOR SEQ ID NO: 19:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 19:

```
GGUCCGAAGU GCAACGGGAA AAUGCACUCC CGGUGAAGCA UAAUGCUGUU          50

CCUGGGGUCU AUGAAAGAAU UUUAUAUCUC UAUUGAAAC                     89
```

(2) INFORMATION FOR SEQ ID NO: 20:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 20:

```
GGUCCGAAGU GCAACGGGAA AAUGCACUGG GAGUGAGGUU CCCCGUUCCU          50

CCCGCACCCU AUGAAAGAAU UUUAUAUCUC UAUUGAAAC                     89
```

(2) INFORMATION FOR SEQ ID NO: 21:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 21:

```
GGUCCGAAGU GCAACGGGAA AAUGCACUAG CGAUGUGAAG UGAUACUGGU          50

CCAUCGUGCU AUGAAAGAAU UUUAUAUCUC UAUUGAAAC                     89
```

(2) INFORMATION FOR SEQ ID NO: 22:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 22:

```
GGUCCGAAGU GCAACGGGAA AAUGCACUCA CAGUGAGCCU UCUGGUGGUC          50

CUGUGUGCUA UGAAAGAAUU UUAUAUCUCU AUUGAAAC                      88
```

(2) INFORMATION FOR SEQ ID NO: 23:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 23:

```
GGUCCGAAGU GCAACGGGAA AAUGCACUUG UUGUGAGUGG UUGAUUCCAU          50

GGUCCAACCU AUGAAAGAAU UUUAUAUCUC UAUUGAAAC                     89
```

(2) INFORMATION FOR SEQ ID NO: 24:

(i) SEQUENCE CHARACTERISTICS:
        (A) LENGTH: 89 base pairs
        (B) TYPE: nucleic acid
        (C) STRANDEDNESS: single
        (D) TOPOLOGY: linear (xi) SEQUENCE DESCRIPTION: SEQ ID NO: 24:

```
GGUCCGAAGU GCAACGGGAA AAUGCACUGC CUGUGAGCUG UUUAGCGGUC          50

CAGGUCGUCU AUGAAAGAAU UUUAUAUCUC UAUUGAAAC                     89
```

(2) INFORMATION FOR SEQ ID NO: 25:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 25:

```
GGUCCGAAGU GCAACGGGAA AAUGCACUCA AGGCGAAGAC UUAGUCUGCU          50

CCCUGUGCUA UGAAAGAAUU UUAUAUCUCU AUUGAAAC                      88
```

(2) INFORMATION FOR SEQ ID NO: 26:

(i) SEQUENCE CHARACTERISTICS:
        (A) LENGTH: 88 base pairs
        (B) TYPE: nucleic acid
        (C) STRANDEDNESS: single
        (D) TOPOLOGY: linear (xi) SEQUENCE DESCRIPTION: SEQ ID NO: 26:

```
GGUCCGAAGU GCAACGGGAA AAUGCACUUG CGUCGAAGUU AAUUCUGGUC          50

GAUGCCACUA UGAAAGAAUU UUAUAUCUCU AUUGAAAC                      88
```

(2) INFORMATION FOR SEQ ID NO: 27:

(i) SEQUENCE CHARACTERISTICS:

(A) LENGTH: 90 base pairs
(B) TYPE: nucleic acid
(C) STRANDEDNESS: single
(D) TOPOLOGY: linear (xi) SEQUENCE DESCRIPTION: SEQ ID NO: 27:

GGUCCGAAGU GCAACGGGAA AAUGCACUUU CAAUGAGGUA UGUAAUGAUG    50

GUCGUGCGCC UAUGAAAGAA UUUUAUAUCU CUAUUGAAAC              90

(2) INFORMATION FOR SEQ ID NO: 28:

(i) SEQUENCE CHARACTERISTICS:
  (A) LENGTH: 89 base pairs
  (B) TYPE: nucleic acid
  (C) STRANDEDNESS: single
  (D) TOPOLOGY: linear (xi) SEQUENCE DESCRIPTION: SEQ ID NO: 28:

GGUCCGAAGU GCAACGGGAA AAUGCACUGC GGGAGAGUCU UUUGACGUUG    50

CUCCUGCGCU AUGAAAGAAU UUUAUAUCUC UAUUGAAAC               89

(2) INFORMATION FOR SEQ ID NO: 29:

(i) SEQUENCE CHARACTERISTICS:
  (A) LENGTH: 88 base pairs
  (B) TYPE: nucleic acid
  (C) STRANDEDNESS: single
  (D) TOPOLOGY: linear (xi) SEQUENCE DESCRIPTION: SEQ ID NO: 29:

GGUCCGAAGU GCAACGGGAA AAUGCACUCA UGGGAGCCCA UCGAUUCUGG    50

GUGUUGCCUA UGAAGAAUU UUAUAUCUCU AUUGAAAC                 88

(2) INFORMATION FOR SEQ ID NO: 30:

(i) SEQUENCE CHARACTERISTICS:
  (A) LENGTH: 88 base pairs
  (B) TYPE: nucleic acid
  (C) STRANDEDNESS: single
  (D) TOPOLOGY: linear (xi) SEQUENCE DESCRIPTION: SEQ ID NO: 30:

GGUCCGAAGU GCAACGGGAA AAUGCACUUG CACAGAGCCA AAUUUGGUGU    50

UGCUGUGCUA UGAAGAAUU UUAUAUCUCU AUUGAAAC                 88

(2) INFORMATION FOR SEQ ID NO: 31:

(i) SEQUENCE CHARACTERISTICS:
  (A) LENGTH: 89 base pairs
  (B) TYPE: nucleic acid
  (C) STRANDEDNESS: single
  (D) TOPOLOGY: linear (xi) SEQUENCE DESCRIPTION: SEQ ID NO: 31:

GGUCCGAAGU GCAACGGGAA AAUGCACUGG CCAGAGCUUA AAUUCAAGUG    50

UUGCUGGCCU AUGAAAGAAU UUUAUAUCUC UAUUGAAAC               89

(2) INFORMATION FOR SEQ ID NO: 32:

(i) SEQUENCE CHARACTERISTICS:
  (A) LENGTH: 89 base pairs
  (B) TYPE: nucleic acid
  (C) STRANDEDNESS: single
  (D) TOPOLOGY: linear (xi) SEQUENCE DESCRIPTION: SEQ ID NO: 32:

GGUCCGAAGU GCAACGGGAA AAUGCACUCA UAGCAGUCCU UGAUACUAUG          50

GAUGGUGGCU AUGAAAGAAU UUUAUAUCUC UAUUGAAAC                     89

(2) INFORMATION FOR SEQ ID NO: 33:

(i) SEQUENCE CHARACTERISTICS:
            (A) LENGTH: 89 base pairs
            (B) TYPE: nucleic acid
            (C) STRANDEDNESS: single
            (D) TOPOLOGY: linear (xi) SEQUENCE DESCRIPTION: SEQ ID NO: 33:

GGUCCGAAGU GCAACGGGAA AAUGCACUGG AUGCAAGUUA ACUCUGGUGG          50

CAUCCGUCCU AUGAAAGAAU UUUAUAUCUC UAUUGAAAC                     89

(2) INFORMATION FOR SEQ ID NO: 34:

(i) SEQUENCE CHARACTERISTICS:
            (A) LENGTH: 88 base pairs
            (B) TYPE: nucleic acid
            (C) STRANDEDNESS: single
            (D) TOPOLOGY: linear (xi) SEQUENCE DESCRIPTION: SEQ ID NO: 34:

GGUCCGAAGU GCAACGGGAA AAUGCACUCA GUGGAGAUUA AGCCUCGCUA          50

GGGGCCGCUA UGAAGAAUU UUAUAUCUCU AUUGAAAC                       88

(2) INFORMATION FOR SEQ ID NO: 35:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ix) FEATURE:
            (D) OTHER INFORMATION:  Y at position 7 is e (ix) FEATURE:
            (D) OTHER INFORMATION:  S at position 1 is b
                the S at position 34

(xi) SEQUENCE DESCRIPTION: SEQ ID NO: 35:

SUGCGUYGAG AUACACNNNG GUGGACUCCC GCAS                          34

(2) INFORMATION FOR SEQ ID NO: 36:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: RNA (ix) FEATURE:
            (D) OTHER INFORMATION:  The N's as positions
                paired to the N's at positions 21-26

(xi) SEQUENCE DESCRIPTION: SEQ ID NO: 36:

UCCGANNNNN NACGGGANAA NNNNNN                                   26

(2) INFORMATION FOR SEQ ID NO: 37:

```
       (i) SEQUENCE CHARACTERISTICS:
           (A) LENGTH: 89 base pairs
           (B) TYPE: nucleic acid
           (C) STRANDEDNESS: single
           (D) TOPOLOGY: linear (ii) MOLECULE TYPE: RNA (xi) SEQUENCE DESCRIPTION: SEQ ID NO: 37:

GGUCCGAAGU GCAACGGGAA AAUGCACUNN NNNNNNNNNN NNNNNNNNNN            50

NNNNNNNNCU AUGAAAGAAU UUUAUAUCUC UAUUGAAAC                        89

(2) INFORMATION FOR SEQ ID NO: 38:

(i) SEQUENCE CHARACTERISTICS:
           (A) LENGTH: 51 base pairs
           (B) TYPE: nucleic acid
           (C) STRANDEDNESS: single
           (D) TOPOLOGY: linear (ii) MOLECULE TYPE: RNA (ix) FEATURE:
           (D) OTHER INFORMATION:  N's at postiions 29-
               paired with N's at positions 48-51

(ix) FEATURE:
           (D) OTHER INFORMATION:  N's at postiions 38-
               paired with N's at positions 40-41

(ix) FEATURE:
           (D) OTHER INFORMATION:  N at position 44 is (xi) SEQUENCE DESCRIPTION: SEQ ID NO: 38:

GGUCCGAAGU GCAACGGGAA AAUGCACUNN NNGUGARNNN NUGNUCCNNN            50

N                                                                51

(2) INFORMATION FOR SEQ ID NO: 39:

(i) SEQUENCE CHARACTERISTICS:
           (A) LENGTH: 54 base pairs
           (B) TYPE: nucleic acid
           (C) STRANDEDNESS: single
           (D) TOPOLOGY: linear (ii) MOLECULE TYPE: RNA (ix) FEATURE:
           (D) OTHER INFORMATION:  N's at postiions 29-
               paired with N's at positions 48-53

(ix) FEATURE:
           (D) OTHER INFORMATION:  N's at postiions 37-
               paired with N's at positions 40-42

(ix) FEATURE:
           (D) OTHER INFORMATION:  N at position 45 is (xi) SEQUENCE DESCRIPTION: SEQ ID NO: 39:

GGUCCGAAGU GCAACGGGAA AAUGCACUNN NNNNAGNNNN NNUGNUGNNN            50

NNNN                                                             54

(2) INFORMATION FOR SEQ ID NO: 40:

(i) SEQUENCE CHARACTERISTICS:
           (A) LENGTH: 37 base pairs
           (B) TYPE: nucleic acid
           (C) STRANDEDNESS: single
           (D) TOPOLOGY: linear
```

-continued (xi) SEQUENCE DESCRIPTION: SEQ ID NO: 40:

GGGUGCAUUG AGAAACACGU UUGUGGACUC UGUAUCU                37

(2) INFORMATION FOR SEQ ID NO: 41:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO: 41:

GGGUGCAUUG AGAAACACGU UUGUGGACUC UGUAUCUAUG AAAGAAUUUU        50

AUAUCUCUAU UGAAAC                                             66

(2) INFORMATION FOR SEQ ID NO: 42:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 42:

GTTTCAATAG AGATATAAAA TTC                                     23

(2) INFORMATION FOR SEQ ID NO: 43:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 43:

GGGACUAUUG AUGGCCUUCC GACCNNNNNN NNNNNNNNNN NNNNNNNNNN        50

NNNNNNNNNN NCACACAGAG GUAAAGAGGA UCCGGG                       86

(2) INFORMATION FOR SEQ ID NO: 44:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 44:

GGGACUAUUG AUGGCCUUCC GACCGGGUGC AUUGAGAAAC ACGUUUGUGG        50

ACUCUGUAUC UCACACAGAG GUAAAGAGGA UCCGGG                       86

(2) INFORMATION FOR SEQ ID NO: 45:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (xi) SEQUENCE DESCRIPTION: SEQ ID NO: 45:

GGGACUAUUG AUGGCCUUCC GACCUGGUGC GUUGAGAAAC AGGUUUUGG         50

ACUCCGUACC ACACAGAGGU AAAGAGGAUC CGGG                         84

(2) INFORMATION FOR SEQ ID NO: 46:

-continued

```
    (i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 46:

GGGACUAUUG AUGGCCUUCC GACCGUAUGC AUUGAGAGAC ACACUUGUGG          50

ACUCUGCAUC CCACACAGAG GUAAAGAGGA UCCGGG                         86

(2) INFORMATION FOR SEQ ID NO: 47:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 47:

GGGACUAUUG AUGGCCUUCC GACCAGAUGG AUUGAGAAAC ACUAUUAUGG          50

ACUCUCCAUC GCACACAGAG GUAAAGAGGA UCCGGG                         86

(2) INFORMATION FOR SEQ ID NO: 48:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 48:

GGGACUAUUG AUGGCCUUCC GACCAGCUUC GUCGAGAUAC ACGUUGAUGG          50

ACUCCGAAGC ACACACAGAG GUAAAGAGGA UCCGGG                         86

(2) INFORMATION FOR SEQ ID NO: 49:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 49:

GGGACUAUUG AUGGCCUUCC GACCUCGUAC GUUGAGAAAC AAGUUUAUGG          50

ACUCCGUACC UCACACAGAG GUAAAGAGGA UCCGGG                         86

(2) INFORMATION FOR SEQ ID NO: 50:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 50:

GGGACUAUUG AUGGCCUUCC GACCUCGAUC GUUGAGAUAC ACGCUAGUGG          50

ACUCCGAAAC UCACACAGAG GUAAAGAGGA UCCGGG                         86

(2) INFORMATION FOR SEQ ID NO: 51:

(i) SEQUENCE CHARACTERISTICS:
        (A) LENGTH: 86 base pairs
        (B) TYPE: nucleic acid
```

```
        (C) STRANDEDNESS: single
        (D) TOPOLOGY: linear (xi) SEQUENCE DESCRIPTION: SEQ ID NO: 51:

GGGACUAUUG AUGGCCUUCC GACCUACUGC AUCGAGAUAC ACGUUUGUGG              50

ACUCUGCACA UCACACAGAG GUAAAGAGGA UCCGGG                            86

(2) INFORMATION FOR SEQ ID NO: 52:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 52:

GGGACUAUUG AUGGCCUUCC GACCUGAUAC GUUGAGAAAC ACAAUGCUGG              50

ACUCCGCAUC CCACACAGAG GUAAAGAGGA UCCGGG                            86

(2) INFORMATION FOR SEQ ID NO: 53:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 53:

GGGACUAUUG AUGGCCUUCC GACCGCCUGC AUUGAGAAAC AGGAUUCUGG              50

ACUCUGCCAC UCACACAGAG GUAAAGAGGA UCCGGG                            86

(2) INFORMATION FOR SEQ ID NO: 54:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 54:

GGGACUAUUG AUGGCCUUCC GACCCGCUAU GUUGAGAAAC ACUUUGCUGG              50

ACUCCGUAGC UCACACAGAG GUAAAGAGGA UCCGGG                            86

(2) INFORMATION FOR SEQ ID NO: 55:

(i) SEQUENCE CHARACTERISTICS:
        (A) LENGTH: 85 base pairs
        (B) TYPE: nucleic acid
        (C) STRANDEDNESS: single
        (D) TOPOLOGY: linear (xi) SEQUENCE DESCRIPTION: SEQ ID NO: 55:

GGGACUAUUG AUGGCCUUCC GACCUACUGC AUCGAGAAAC ACGUAAGUGA              50

CUCUGCAUCC CACACAGAGG UAAAGAGGAU CCGGG                             85

(2) INFORMATION FOR SEQ ID NO: 56:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 56:
```

```
GGGACUAUUG AUGGCCUUCC GACCCGGUAC GUCGAGAUAC ACGAAGAUGG         50

ACUCCGUAUC GCACACAGAG GUAAAGAGGA UCCGGG                       86

(2) INFORMATION FOR SEQ ID NO: 57:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 57:

GGGACUAUUG AUGGCCUUCC GACCAACUCC AUCGAGAAAC ACGAUAGUGG         50

ACUCUGGAGC UCACACAGAG GUAAAGAGGA UCCGGG                       86

(2) INFORMATION FOR SEQ ID NO: 58:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 58:

GGGACUAUUG AUGGCCUUCC GACCGGAGAC GUCGAGAAAC ACGUUUGUGG        50

ACUCCGUCUC UCACACAGAG GUAAAGAGGA UCCGGG                       86

(2) INFORMATION FOR SEQ ID NO: 59:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 59:

GGGACUAUUG AUGGCCUUCC GACCAGCUAC AUCGAGAAAC AAGAUUUGG         50

ACUCUGUAGC GCACACAGAG GUAAAGAGGA UCCGGG                       86

(2) INFORMATION FOR SEQ ID NO: 60:

(i) SEQUENCE CHARACTERISTICS:
        (A) LENGTH: 83 base pairs
        (B) TYPE: nucleic acid
        (C) STRANDEDNESS: single
        (D) TOPOLOGY: linear (xi) SEQUENCE DESCRIPTION: SEQ ID NO: 60:

GGGACUAUUG AUGGCCUUCC GACCAAGUGC AUUGAGAUAC AAAUGAUGG         50

ACUCUGCACA CACAGAGGUA AAGAGGAUCC GGG                          83

(2) INFORMATION FOR SEQ ID NO: 61:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 61:

GGGACUAUUG AUGGCCUUCC GACCUGCUAC GUUGAGAUAC ACGUUGAUGC         50

ACUCCGUAGC UCACACAGAG GUAAAGAGGA UCCGGG                       86
```

(2) INFORMATION FOR SEQ ID NO: 62:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 62:

```
GGGACUAUUG AUGGCCUUCC GACCAGCUAC GUUGAGAUAC ACGUUACGUG          50
GCUCCGUAGC CCACACAGAG GUAAAGAGGA UCCGGG                         86
```

(2) INFORMATION FOR SEQ ID NO: 63:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 63:

```
GGGACUAUUG AUGGCCUUCC GACCGAGUGG CUCGAGAAAC AGGUUGCUGG          50
ACUCGCCACA UCACACAGAG GUAAAGAGGA UCCGGG                         86
```

(2) INFORMATION FOR SEQ ID NO: 64:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 64:

```
GGGACUAUUG AUGGCCUUCC GACCUCGUGC GUCGAGCAAC ACGUUGAUGG          50
ACUCCGCACA GCACACAGAG GUAAAGAGGA UCCGGG                         86
```

(2) INFORMATION FOR SEQ ID NO: 65:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 65:

```
GGGACUAUUG AUGGCCUUCC GACCGGCACC GUUGAGAAAC ACAUGCGUGG          50
ACUCCGUGCC CCACACAGAG GUAAAGAGGA UCCGGG                         86
```

(2) INFORMATION FOR SEQ ID NO: 66:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 66:

```
GGGACUAUUG AUGGCCUUCC GACCUCCUGC AUUGAGAAAC AGUGAUCUGG          50
ACUCUGCAAC UCACACAGAG GUAAAGAGGA UCCGGG                         86
```

(2) INFORMATION FOR SEQ ID NO: 67:

```
        (i) SEQUENCE CHARACTERISTICS:
            (A) LENGTH: 85 base pairs
            (B) TYPE: nucleic acid
            (C) STRANDEDNESS: single
            (D) TOPOLOGY: linear (xi) SEQUENCE DESCRIPTION: SEQ ID NO: 67:

GGGACUAUUG AUGGCCUUCC GACCUGUGGA UUGAGCAACA CGUGAGUGGA          50

CUCUCCACAU CACACAGAGG UAAAGAGGAU CCGGG                          85

(2) INFORMATION FOR SEQ ID NO: 68:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (xi) SEQUENCE DESCRIPTION: SEQ ID NO: 68:

GGGACUAUUG AUGGCCUUCC GACCCCGUGC GUUGAGACAC ACACCGAUGG          50

ACUCCGCAUG UCACACAGAG GUAAAGAGGA UCCGGG                         86

(2) INFORMATION FOR SEQ ID NO: 69:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (xi) SEQUENCE DESCRIPTION: SEQ ID NO: 69:

GGGACUAUUG AUGGCCUUCC GACCAGCUGC AUCGAGAUAC ACGAUUGUGG          50

ACUCUGCAGC CCACACAGAG GUAAAGAGGA UCCGGG                         86

(2) INFORMATION FOR SEQ ID NO: 70:

(i) SEQUENCE CHARACTERISTICS:
            (A) LENGTH: 87 base pairs
            (B) TYPE: nucleic acid
            (C) STRANDEDNESS: single
            (D) TOPOLOGY: linear (xi) SEQUENCE DESCRIPTION: SEQ ID NO: 70:

GGGACUAUUG AUGGCCUUCC GACCAGAUUC GUUGAGAAAC ACAUGGGUGG          50

ACUCUCCCGC UACACACAGA GGUAAAGAGG AUCCGGG                        87

(2) INFORMATION FOR SEQ ID NO: 71:

(i) SEQUENCE CHARACTERISTICS:
            (A) LENGTH: 86 base pairs
            (B) TYPE: nucleic acid
            (C) STRANDEDNESS: single
            (D) TOPOLOGY: linear (xi) SEQUENCE DESCRIPTION: SEQ ID NO: 71:

GGGACUAUUG AUGGCCUUCC GACCAGAUGG AUUGAGAAAC ACGUUCGUGG          50

ACUCUCCAAC UCACACAGAG GUAAAGAGGA UCCGGG                         86

(2) INFORMATION FOR SEQ ID NO: 72:

(i) SEQUENCE CHARACTERISTICS:
            (A) LENGTH: 86 base pairs
            (B) TYPE: nucleic acid
            (C) STRANDEDNESS: single
```

(D) TOPOLOGY: linear (xi) SEQUENCE DESCRIPTION: SEQ ID NO: 72:

GGGACUAUUG AUGGCCUUCC GACCGACUGC AUCGAGAAAC ACUGAUGUGG          50

CCUCCGCACG GCACACAGAG GUAAAGAGGA UCCGGG                        86

(2) INFORMATION FOR SEQ ID NO: 73:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 73:

GGGACUAUUG AUGGCCUUCC GACCAGCUAC GUUGAGAAAC AGUAUAAUGG          50

ACUCCGUAGC UCACACAGAG GUAAAGAGGA UCCGGG                        86

(2) INFORMATION FOR SEQ ID NO: 74:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 74:

GGGACUAUUG AUGGCCUUCC GACCGAGUGC GUCGAGAAAC ACAUUUGUGG          50

ACUCCGCACA CCACACAGAG GUAAAGAGGA UCCGGG                        86

(2) INFORMATION FOR SEQ ID NO: 75:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 75:

GGGACUAUUG AUGGCCUUCC GACCUCGUAC GUUGAGAAAC ACGCUAGUGG          50

ACUCCGUAUG UCACACAGAG GUAAAGAGGA UCCGGG                        86

(2) INFORMATION FOR SEQ ID NO: 76:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 76:

GGGACUAUUG AUGGCCUUCC GACCAGAUAC GUUGAGAGAC ACGCACGUGG          50

ACUCCGUAUC UCACACAGAG GUAAAGAGGA UCCGGG                        86

(2) INFORMATION FOR SEQ ID NO: 77:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 77:

```
GGGACUAUUG AUGGCCUUCC GACCAGGAUC ACAGAGAAAC ACCGUGGGUG          50

GCUCCCUCUA UCACACAGAG GUAAAGAGGA UCCGGG                        86
```

(2) INFORMATION FOR SEQ ID NO: 78:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (xi) SEQUENCE DESCRIPTION: SEQ ID NO: 78:

```
GGGACUAUUG AUGGCCUUCC GACCGUGCGC AUCGAGAAAC ACGUUGAUGG         50

ACUCUGCAUG CACACACAGA GGUAAAGAGG AUCCGGG                       87
```

(2) INFORMATION FOR SEQ ID NO: 79:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 79:

```
GGGACUAUUG AUGGCCUUCC GACCGAGAGG AUCGAGAAAC ACGUAUGUGG         50

ACUCUCCAUC UCACACAGAG GUAAAGAGGA UCCGGG                        86
```

(2) INFORMATION FOR SEQ ID NO: 80:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 80:

```
GGGACUAUUG AUGGCCUUCC GACCGGAUGG AUUGAGACAC ACGUAUGUGG         50

ACUCUCCAUC ACACACAGAG GUAAAGAGGA UCCGGG                        86
```

(2) INFORMATION FOR SEQ ID NO: 81:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 81:

```
GGGACUAUUG AUGGCCUUCC GACCUCGGGC AUUGAGAUAC ACGUAGAUGG         50

ACUCUGUCUC ACACACAGAG GUAAAGAGGA UCCGGG                        86
```

(2) INFORMATION FOR SEQ ID NO: 82:

(i) SEQUENCE CHARACTERISTICS:
        (A) LENGTH: 86 base pairs
        (B) TYPE: nucleic acid
        (C) STRANDEDNESS: single
        (D) TOPOLOGY: linear (xi) SEQUENCE DESCRIPTION: SEQ ID NO: 82:

```
GGGACUAUUG AUGGCCUUCC GACCUGGACC GUAGAGAAAC ACGUUUGAUG         50

GCUCCCUCUG UCACACAGAG GUAAAGAGGA UCCGGG                        86
```

```
(2) INFORMATION FOR SEQ ID NO: 83:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: RNA (ix) FEATURE:
        (D) OTHER INFORMATION:  N's at positions 1-5
            N's at positions 25-29

(ix) FEATURE:
        (D) OTHER INFORMATION:  N at position 16 is
            position 17

(xi) SEQUENCE DESCRIPTION: SEQ ID NO: 83:

NNNNNUUGAG AUACANNUGG ACUCNNNNN                                       29
```

METHODS OF PRODUCING NUCLEIC ACID LIGANDS

This application is a continuation application of U.S. patent application Ser. No. 10/040,497, filed Jan. 7, 2002, now issued as U.S. Pat. No. 6,716,583, which is a continuation of U.S. patent application Ser. No. 09/165,616, filed Oct. 2, 1998, entitled "Methods of Producing Nucleic Acid Ligands," which is a continuation application of U.S. patent application Ser. No. 08/748,697, filed Nov. 13, 1996, entitled "Methods of Producing Nucleic Acid Ligands," now issued as U.S. Pat. No. 5,817,785, which is a continuation of U.S. patent application Ser. No. 08/442,062, filed May 16, 1995, entitled "Methods of Producing Nucleic Acid Ligands," now issued as U.S. Pat. No. 5,595,877. U.S. patent application Ser. No. 08/442,062 is a divisional of U.S. patent application Ser. No. 07/964,624, filed Oct. 21, 1992, entitled "Nucleic Acid Ligands to HIV-RT and HIV-1 Rev," now issued as U.S. Pat. No. 5,496,938. U.S. patent application Ser. No. 07/964,624 is a continuation-in-part of U.S. patent application Ser. No. 07/714,131, filed Jun. 10, 1991, entitled "Nucleic Acid Ligands," now issued as U.S. Pat. No. 5,475,096, which is a continuation-in-part of U.S. patent application Ser. No. 07/536,428, filed Jun. 11, 1990, entitled "Systematic Evolution of Ligands by Exponential Enrichment," now abandoned. All applications cited herein are expressly incorporated in their entirety by this reference.

FIELD OF THE INVENTION

Described herein are methods for identifying and producing nucleic acid ligands. Nucleic acid ligands are double or single stranded DNA or RNA species that bind specifically to a desired target molecule. The basis for identifying nucleic acid ligands is a method that is called SELEX™, an acronym for Systematic Evolution of Ligands by Exponential Enrichment. The methods of the present invention include means for analyzing and applying the information learned from the SELEX method to create an improved nucleic acid ligand for the selected target. These methods include computer modeling, boundary determination methods and chemical modification methods. According to the methods of this invention it is possible to determine: 1) which nucleic acid residues of a nucleic acid ligand are critical in binding to the selected target; 2) which nucleic acid residues affect the structural conformation of the nucleic acid ligand; and 3) what is the three-dimensional structure of the nucleic acid ligand. This information allows for the identification and production of improved nucleic acid ligands that have superior binding capacity to the target as well as enhanced structural stability. This information may also be utilized to produce non-nucleic acid or hybrid-nucleic acid species that also function as ligands to the target. The methods of the present invention further provide an analysis of the target species that can be used in the preparation of therapeutic and/or diagnostic methods.

BACKGROUND OF THE INVENTION

Most proteins or small molecules are not known to specifically bind to nucleic acids. The known protein exceptions are those regulatory proteins such as repressors, polymerases, activators and the like which function in a living cell to bring about the transfer of genetic information encoded in the nucleic acids into cellular structures and the replication of the genetic material. Furthermore, small molecules such as GTP bind to some intron RNAs.

Living matter has evolved to limit the function of nucleic acids to a largely informational role. The Central Dogma, as postulated by Crick, both originally and in expanded form, proposes that nucleic acids (either RNA or DNA) can serve as templates for the synthesis of other nucleic acids through replicative processes that "read" the information in a template nucleic acid and thus yield complementary nucleic acids. All of the experimental paradigms for genetics and gene expression depend on these properties of nucleic acids: in essence, double-stranded nucleic acids are informationally redundant because of the chemical concept of base pairs and because replicative processes are able to use that base pairing in a relatively error-free manner.

The individual components of proteins, the twenty natural amino acids, possess sufficient chemical differences and activities to provide an enormous breadth of activities for both binding and catalysis. Nucleic acids, however, are thought to have narrower chemical possibilities than proteins, but to have an informational role that allows genetic information to be passed from virus to virus, cell to cell, and organism to organism. In this context nucleic acid components, the nucleotides, must possess only pairs of surfaces that allow informational redundancy within a Watson-Crick base pair. Nucleic acid components need not possess chemical differences and activities sufficient for either a wide range of binding or catalysis.

However, some nucleic acids found in nature do participate in binding to certain target molecules and even a few instances of catalysis have been reported. The range of activities of this kind is narrow compared to proteins and more specifically antibodies. For example, where nucleic acids are known to bind to some protein targets with high affinity and specificity, the binding depends on the exact sequences of nucleotides that comprise the DNA or RNA ligand. Thus, short double-stranded DNA sequences are known to bind to target proteins that repress or activate transcription in both prokaryotes and eukaryotes. Other short double-stranded DNA sequences are known to bind to restriction endonucleases, protein targets that can be selected with high affinity and specificity. Other short DNA sequences serve as centromeres and telomeres on chromosomes, presumably by creating ligands for the binding of specific proteins that participate in chromosome mechanics. Thus, double-stranded DNA has a well-known capacity to bind within the nooks and crannies of target proteins whose functions are directed to DNA binding. Single-stranded DNA can also bind to some proteins with high affinity and specificity, although the number of examples is rather smaller. From the known examples of double-stranded DNA binding proteins, it has become possible to describe the binding interactions as involving various protein motifs projecting amino acid side chains into the major groove of B form double-stranded DNA, providing the sequence inspection that allows specificity.

Double-stranded RNA occasionally serves as a ligand for certain proteins, for example, the endonuclease RNase III from *E. coli*. There are more known instances of target proteins that bind to single-stranded RNA ligands, although in these cases the single-stranded RNA often forms a complex three-dimensional shape that includes local regions of intramolecular double-strandedness. The amino-acyl tRNA synthetases bind tightly to tRNA molecules with high specificity. A short region within the genomes of RNA viruses binds tightly and with high specificity to the viral coat proteins. A short sequence of RNA binds to the bacteriophage T4-encoded DNA polymerase, again with high affinity and specificity. Thus, it is possible to find RNA and DNA ligands, either double- or single-stranded, serving as binding partners for specific protein targets. Most known DNA binding proteins bind specifically to double-stranded DNA, while most RNA binding proteins recognize single-stranded RNA. This statistical bias in the literature no doubt reflects the present biosphere's statistical predisposition to use DNA as a double-stranded genome and RNA as a single-stranded entity in the roles RNA plays beyond serving as a genome. Chemically there is no strong reason to dismiss single-stranded DNA as a fully able partner for specific protein interactions.

RNA and DNA have also been found to bind to smaller target molecules. Double-stranded DNA binds to various antibiotics, such as actinomycin D. A specific single-stranded RNA binds to the antibiotic thiostreptone; specific RNA sequences and structures probably bind to certain other antibiotics, especially those whose functions is to inactivate ribosomes in a target organism. A family of evolutionary related RNAs binds with specificity and decent affinity to nucleotides and nucleosides (Bass and Cech (1984) Nature 308:820-826) as well as to one of the twenty amino acids (Yarus (1988) Science 240:1751-1758). Catalytic RNAs are now known as well, although these molecules perform over a narrow range of chemical possibilities, which are thus far related largely to phosphodiester transfer reactions and hydrolysis of nucleic acids.

Despite these known instances, the great majority of proteins and other cellular components are thought not to bind to nucleic acids under physiological conditions and such binding as may be observed is non-specific. Either the capacity of nucleic acids to bind other compounds is limited to the relatively few instances enumerated above, or the chemical repertoire of the nucleic acids for specific binding is avoided (selected against) in the structures that occur naturally. The present invention is premised on the inventors' fundamental insight that nucleic acids as chemical compounds can form a virtually limitless array of shapes, sizes and configurations, and are capable of a far broader repertoire of binding and catalytic functions than those displayed in biological systems.

The chemical interactions have been explored in cases of certain known instances of protein-nucleic acid binding. For example, the size and sequence of the RNA site of bacteriophage R17 coat protein binding has been identified by Uhlenbeck and coworkers. The minimal natural RNA binding site (21 bases long) for the R17 coat protein was determined by subjecting variable-sized labeled fragments of the mRNA to nitrocellulose filter binding assays in which protein-RNA fragment complexes remain bound to the filter (Carey et al. (1983) Biochemistry 22:2601). A number of sequence variants of the minimal R17 coat protein binding site were created in vitro in order to determine the contributions of individual nucleic acids to protein binding (Uhlenbeck et al. (1983) J. Biomol. Structure & Dynamics 1:539; Romaniuk et al. (1987) Biochemistry 26:1563). It was found that the maintenance of the hairpin loop structure of the binding site was essential for protein binding but, in addition, that nucleotide substitutions at most of the single-stranded residues in the binding site, including a bulged nucleotide in the hairpin stem, significantly affected binding. In similar studies, the binding of bacteriophage Qβ coat protein to its translational operator was examined (Witherell and Uhlenbeck (1989) Biochemistry 28:71). The Qβ coat protein RNA binding site was found to be similar to that of RI 7 in size, and in predicted secondary structure, in that it comprised about 20 bases with an 8 base pair hairpin structure which included a bulged nucleotide and a 3 base loop. In contrast to the R17 coat protein binding site, only one of the single-stranded residues of the loop is essential for binding and the presence of the bulged nucleotide is not required. The protein-RNA binding interactions involved in translational regulation display significant specificity.

Nucleic acids are known to form secondary and tertiary structures in solution. The double-stranded forms of DNA include the so-called B double-helical form, Z-DNA and superhelical twists (Rich et al. (1984) Ann. Rev. Biochem. 53:791-846). Single-stranded RNA forms localized regions of secondary structure such as hairpin loops and pseudoknot structures (Schimmel (1989) Cell 58:9-12). However, little is known concerning the effects of unpaired loop nucleotides on stability of loop structure, kinetics of formation and denaturation, thermodynamics, and almost nothing is known of tertiary structures and three dimensional shape, nor of the kinetics and thermodynamics of tertiary folding in nucleic acids (Tuerk et al. (1988) Proc. Natl. Acad. Sci. USA 85:1364-1368).

A type of in vitro evolution was reported in replication of the RNA bacteriophage Qβ. (See Mills et al. (1967) Proc. Natl. Acad. Sci USA 58:217-224; Levisohn and Spiegelman (1968) Proc. Natl. Acad. Sci. USA 60:866-872; Levisohn and Spiegelman (1969) Proc. Natl. Acad. Sci. USA 63:805-811; Saffhill et al. (1970) J. Mol. Biol. 51:531-539; Kacian et al. (1972) Proc. Natl. Acad. Sci. USA 69:3038-3042; Mills et al. (1973) Science 180:916-927). The phage RNA serves as a poly-cistronic messenger RNA directing translation of phage-specific proteins and also as a template for its own replication catalyzed by Qβ RNA replicase. This RNA replicase was shown to be highly specific for its own RNA templates. During the course of cycles of replication in vitro small variant RNAs were isolated which were also replicated by Qβ replicase. Minor alterations in the conditions under which cycles of replication were performed were found to result in the accumulation of different RNAs, presumably because their replication was favored under the altered conditions. In these experiments, the selected RNA had to be bound efficiently by the replicase to initiate replication and had to serve as a kinetically favored template during elongation of RNA. Kramer et al. (1974) J. Mol. Biol. 89:719 reported the isolation of a mutant RNA template of Qβ replicase, the replication of which was more resistant to inhibition by ethidium bromide than the natural template. It was suggested that this mutant was not present in the initial RNA population but was generated by sequential mutation during cycles of in vitro replication with Qβ replicase. The only source of variation during selection was the intrinsic error rate during elongation by Qβ replicase. In these studies what was termed "selection" occurred by preferential amplification of one or more of a limited number of spontaneous variants of an initially homogenous RNA sequence. There was no selection of a desired result, only that which was intrinsic to the mode of action of Qβ replicase.

Joyce and Robertson reported a method for identifying RNA which specifically cleave single-stranded DNA (Joyce (1989) in *RNA: Catalysis, Splicing Evolution*, Belfort and Shub (eds.), Elsevier, Amsterdam pp. 83-87; Robertson and Joyce (1990) Nature 344:467). The selection for catalytic activity was based on the ability of the ribozyme to catalyze the cleavage of a substrate ssRNA or DNA at a specific position and transfer the 3'-end of the substrate to the 3'-end of the ribozyme. The product of the desired reaction was selected by using an oligodeoxynucleotide primer which could bind only to the completed product across the junction formed by the catalytic reaction and allowed selective reverse transcription of the ribozyme sequence. The selected catalytic sequences were amplified by attachment of the promoter of T7 RNA polymerase to the 3'-end of the cDNA, followed by transcription to RNA. The method was employed to identify from a small number of ribozyme variants, the variant that was most reactive for cleavage of a selected substrate.

The prior art has not taught or suggested more than a limited range of chemical functions for nucleic acids in their interactions with other substances: as targets for proteins evolved to bind certain specific oligonucleotide sequences; and more recently, as catalysts with a limited range of activities. Prior "selection" experiments have been limited to a narrow range of variants of a previously described function. Now, for the first time, it will be understood that the nucleic acids are capable of a vastly broad range of functions and the methodology for realizing that capability is disclosed herein.

U.S. patent application Ser. No. 07/536,428 filed Jun. 11, 1990, entitled "Systematic Evolution of Ligands by Exponential Enrichment," now abandoned and U.S. patent application Ser. No. 07/714,131 filed Jun. 10, 1991 entitled "Nucleic Acid Ligands," now U.S. Pat. No. 5,475,096 (see also WO 91/19813) describe a fundamentally novel method for making a nucleic acid ligand for any desired target. Each of these applications, collectively referred to herein as the SELEX Patent Applications, is specifically incorporated herein by reference.

The method of the SELEX Patent Applications is based on the unique insight that nucleic acids have sufficient capacity for forming a variety of two- and three-dimensional structures and sufficient chemical versatility available within their monomers to act as ligands (form specific binding pairs) with virtually any chemical compound, whether large or small in size.

The method involves selection from a mixture of candidates and step-wise iterations of structural improvement, using the same general selection theme, to achieve virtually any desired criterion of binding affinity and selectivity. Starting from a mixture of nucleic acids, preferably comprising a segment of randomized sequence, the method, termed SELEX herein, includes steps of contacting the mixture with the target under conditions favorable for binding, partitioning unbound nucleic acids from those nucleic acids which have bound to target molecules, dissociating the nucleic acid-target pairs, amplifying the nucleic acids dissociated from the nucleic acid-target pairs to yield a ligand-enriched mixture of nucleic acids, then reiterating the steps of binding, partitioning, dissociating and amplifying through as many cycles as desired.

While not bound by a theory of preparation, SELEX is based on the inventors' insight that within a nucleic acid mixture containing a large number of possible sequences and structures there is a wide range of binding affinities for a given target. A nucleic acid mixture comprising, for example a 20 nucleotide randomized segment can have $4^{20}$ candidate possibilities. Those which have the higher affinity constants for the target are most likely to bind. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands.

Cycles of selection and amplification are repeated until a desired goal is achieved. In the most general case, selection/amplification is continued until no significant improvement in binding strength is achieved on repetition of the cycle. The method may be used to sample as many as about $10^{18}$ different nucleic acid species. The nucleic acids of the test mixture preferably include a randomized sequence portion as well as conserved sequences necessary for efficient amplification. Nucleic acid sequence variants can be produced in a number of ways including synthesis of randomized nucleic acid sequences and size selection from randomly cleaved cellular nucleic acids. The variable sequence portion may contain fully or partially random sequence; it may also contain subportions of conserved sequence incorporated with randomized sequence. Sequence variation in test nucleic acids can be introduced or increased by mutagenesis before or during the selection/amplification iterations.

In one embodiment of the method of the SELEX Patent Applications, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX until a single nucleic acid ligand is identified. The target-specific nucleic acid ligand solution may include a family of nucleic acid structures or motifs that have a number of conserved sequences and a number of sequences which can be substituted or added without significantly effecting the affinity of the nucleic acid ligands to the target. By terminating the SELEX process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, psuedoknots and myriad combinations of the same. Almost all known cases of such motifs suggest that they can be formed in a nucleic acid sequence of no more than 30 nucleotides. For this reason, it is often preferred that SELEX procedures with contiguous randomized segments be initiated with nucleic acid sequences containing a randomized segment of between about 20-50 nucleotides.

The SELEX Patent Applications also describe methods for obtaining nucleic acid ligands that bind to more than one site on the target molecule, and to nucleic acid ligands that include non-nucleic acid species that bind to specific sites on the target. The SELEX method provides means for isolating and identifying nucleic acid ligands which bind to any envisonable target. However, in preferred embodiments the SELEX method is applied to situations where the target is a protein, including both nucleic acid-binding proteins and proteins not known to bind nucleic acids as part of their biological function.

Little is known about RNA structure at high resolution. The basic A-form helical structure of double stranded RNA is known from fiber diffraction studies. X-ray crystallography has yielded the structure of a few tRNAs and a short poly-AU helix. The X-ray structure of a tRNA/synthetase RNA/protein complex has also been solved. The structures of two tetranucleotide hairpin loops and one model pseudoknot are know from NMR studies.

There are several reasons behind the paucity of structural data. Until the advent of in vitro RNA synthesis, it was difficult to isolate quantities of RNA sufficient for structural work. Until the discovery of catalytic RNAs, there were few RNA molecules considered worthy of structural study. Good tRNA crystals have been difficult to obtain, discouraging other crystal studies. The technology for NMR study of molecules of this size has only recently become available.

As described above, several examples of catalytic RNA structures are known, and the SELEX technology has been developed which selects RNAs that bind tightly to a variety of target molecules and may eventually be able to select for new catalytic RNA structures as well. It has become important to know the structure of these molecules, in order to learn how exactly they work, and to use this knowledge to improve upon them.

It would be desirable to understand enough about RNA folding to be able to predict the structure of an RNA with less effort than resorting to rigorous NMR, and X-ray crystal structure determination. For both proteins and RNAs, there has always been a desire to be able to compute structures based on sequences, and with limited (or no) experimental data.

Protein structure prediction is notoriously difficult. To a first approximation, the secondary structure and tertiary structure of proteins form cooperatively; protein folding can be approximated thermodynamically by a two-state model, with completely folded and completely unfolded states. This means that the number of degrees of freedom for modeling a protein structure are very large; without predictable intermediates, one cannot break the prediction problem into smaller, manageable sub problems. In contrast, RNAs often appear to make well-defined secondary structures which provide more stability than the tertiary interactions. For example, the tertiary structure of tRNA can be disrupted without disrupting the secondary structure by chelation of magnesium or by raising the temperature. Secondary structure prediction for RNAs is well-understood, and is generally quite accurate for small RNA molecules. For RNAs, structural prediction can be broken into subproblems; first, predict the secondary structure; then, predict how the resulting helices and remaining single strands are arranged relative to each other.

For RNA, the first attempts at structural prediction were for tRNAs. The secondary structure of the canonical tRNA cloverleaf was known from comparative sequence analysis, reducing the problem to one of arranging four short A-form helices in space relative to each other. Manual CPK modeling, back-of-the-envelope energy minimization, and a few distance restraints available from crosslinking studies and phylogenetic covariations were used to generate a tRNA model, which unfortunately proved wrong when the first crystal structure of phenylalanine tRNA was solved a few years later.

Computer modeling has supplanted manual modeling, relieving the model-builder of the difficulties imposed by gravitation and mass. Computer modeling can only be used without additional experimental data for instances in which a homologous structure is known; for instance, the structure of the 3' end of the turnip yellow mosaic virus RNA genome was modeled, based on the known 3D structure of tRNA and the knowledge that the 3' end of TYMV is recognized as tRNA-like by a number of cellular tRNA modification enzymes. This model was the first 3D model of an RNA pseudoknot; the basic structure of an isolated model pseudoknot has been corroborated by NMR data.

Computer modeling protocols have been used, restrained by the manual inspection of chemical and enzymatic protection data, to model the structures of several RNA molecules. In one isolated substructure, one model for the conformation of a GNRA tetranucleotide loop has been shown to be essentially correct by NMR study of an isolated GNRA hairpin loop.

Francois Michel, has constructed a model for the catalytic core of group I introns (Michel (1989) Nature 342:391). Like the tRNAs, the secondary structure of group I intron cores is well-known from comparative sequence analysis, so the problem is reduced to one of properly arranging helices and the remaining single-stranded regions. Michel analyzed an aligned set of 87 group I intron sequences by eye and detected seven strong pairwise and triplet covariations outside of the secondary structure, which he interpreted as tertiary contacts and manually incorporated as restraints on his model (Michel (1989) Nature 342:391). As yet, there is no independent confirmation of the Michel model.

Others have attempted to devise an automated procedure to deal with distance restraints from crosslinking, fluorescence transfer, or phylogentic co-variation. The RNA is treated as an assemblage of cylinders (A-form helices) and beads (single-stranded residues), and a mathematical technique called distance geometry is used to generate arrangements of these elements which are consistent with a set of distance restraints. Using a small set of seven distance restraints on the phenylalanine tRNA tertiary structure, this protocol generated the familiar L-form of the tRNA structure about ⅔ of the time.

SUMMARY OF THE INVENTION

The present invention includes methods for identifying and producing nucleic acid ligands and the nucleic acid ligands so identified and produced. The SELEX method described above allows for the identification of a single nucleic acid ligand or a family of nucleic acid ligands to a given target. The methods of the present invention allow for the analysis of the nucleic acid ligand or family of nucleic acid ligands obtained by SELEX in order to identify and produce improved nucleic acid ligands.

Included in this invention are methods for determining the three-dimensional structure of nucleic acid ligands. Such methods include mathematical modeling and structure modifications of the SELEX derived ligands. Further included are methods for determining which nucleic acid residues in a nucleic acid ligand are necessary for maintaining the three-dimensional structure of the ligand, and which residues interact with the target to facilitate the formation of ligand-target binding pairs.

In one embodiment of the present invention, nucleic acid ligands are desired for their ability to inhibit one or more of the biological activities of the target. In such cases, methods are provided for determining whether the nucleic acid ligand effectively inhibits the desired biological activity.

Further included in this invention are methods for identifying tighter-binding RNA ligands and smaller, more stable ligands for use in pharmaceutical or diagnostic purposes.

The present invention includes improved nucleic acid ligands to the HIV-RT and HIV-1 Rev proteins. Also included are nucleic acid sequences that are substantially homologous to and that have substantially the same ability to bind HIV-RT or the HIV-1 Rev protein as the nucleic acid ligands specifically identified herein.

Also included within the scope of the invention is a method for performing sequential SELEX experiments in order to identify extended nucleic acid ligands. In particular, extended nucleic acid ligands to the HIV-RT protein are disclosed. Nucleic acid sequences that are substantially homologous to and that have substantially the same ability to bind HIV-RT as the extended HIV-RT nucleic acid ligands are also included in this invention.

(SEQ ID NO:89)
5'-(AAAAA)$_d$(UCCGA)$_x$(AGUGCA)$_m$(ACGGGAAAA)$_x$
(UGCACU)$_m$-3' where subscripted "d" indicates 2'-deoxy, subscripted "x" that those nucleotides are mixed 50-50 for phosphoramidite reagents resulting in 2'-methoxy or 2'-hydroxyl on the ribose, and subscripted "m" indicating that those nucleotides are all 2'-methoxy on the ribose.

FIG. 9 shows the starting RNA sequence (SEQ ID NO:37) and the collection of sequences, grouped into two motifs, Extension Motif I (SEQ ID NOS:14-27) and Extension Motif II (SEQ ID NOS:28-33), obtained from SELEX with HIV-RT as part of a walking experiment.

FIG. 10A illustrates the secondary structure of the first 25 bases of the starting material shown in FIG. 9.

FIGS. 10B and 10C illustrate the consensus extended HIV-RT ligands obtained from the Extension Motif I (SEQ ID NO:38) (FIG. 10B) and Extension Motif II (SEQ ID NO:39) (FIG. 10C), shown in FIG. 9.

FIG. 11 illustrates the revised description of the pseudoknot ligand of HIV-RT. In addition to the labeling conventions of FIG. 1, the S-S' indicates the preferred C-G or G-C base-pair at this position.

FIG. 12A shows the sequence of a high-affinity RNA ligand for HIV-1 Rev protein obtained from SELEX experiments (SEQ ID NO:40). Shown is the numbering scheme used for reference to particular bases in the RNA. This sequence was used for chemical modification with ENU.

FIG. 12B shows the extended RNA sequence (SEQ ID NO:41) used in chemical modification experiments with DMS, kethoxal, CMCT, and DEPC.

FIG. 12C shows the sequence of the oligonucleotide used for primer extension of the extended ligand sequence (SEQ ID NO:42).

FIG. 13 depicts the results of chemical modification of the HIV-1 Rev RNA ligand (SEQ ID NO:40) under native conditions. FIG. 13A lists chemical modifying agents, their specificity, and the symbols denoting partial and full modification. The RNA sequence is shown, with degree and type of modification displayed for every modified base. FIG. 13B depicts the helical, bulge and hairpin structural elements of the HIV-1 Rev RNA ligand corresponding to the modification and computer structural prediction data.

Figure 14:
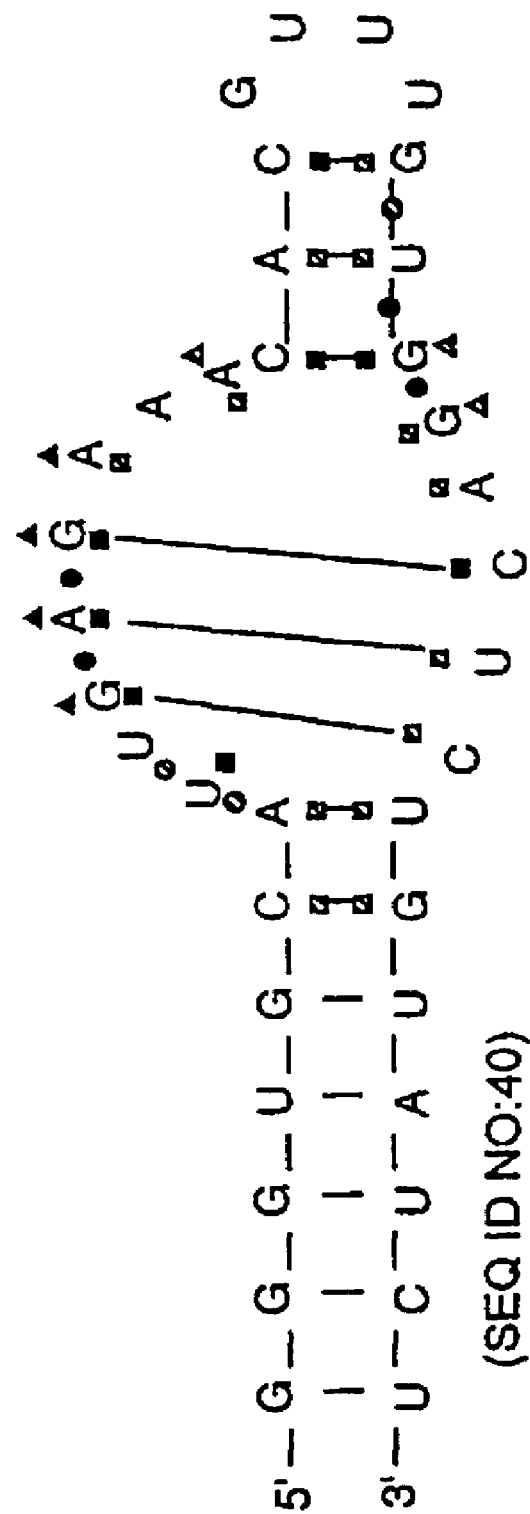

FIG. 14 depicts the results of chemical modification of the RNA ligand (SEQ ID NO:40) that interferes with binding to the HIV-1 Rev protein. Listed are the modifications which interfere with protein binding, classified into categories of strong interference and slight interference. Symbols denote either base-pairing modifications, N7 modifications or phosphate modifications.

Figure 15:
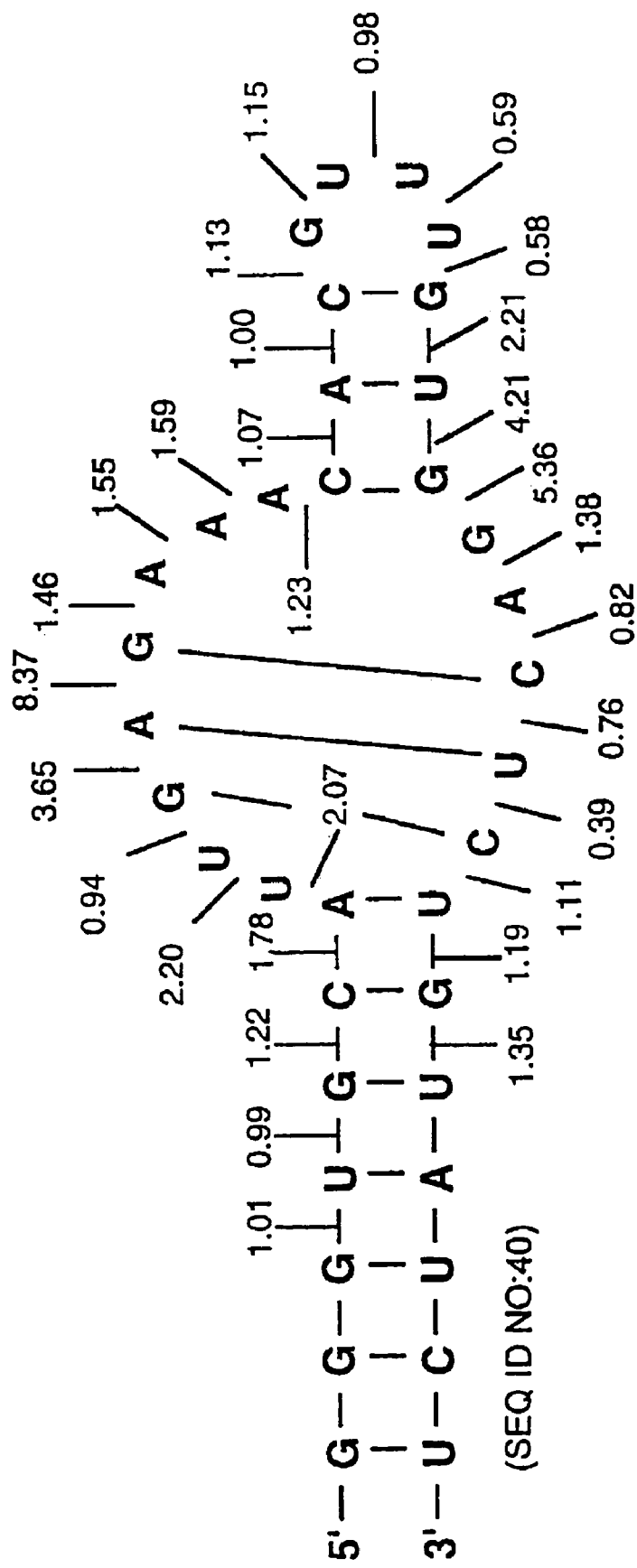

FIG. 15 depicts the modification interference values for phosphate alkylation. Data is normalized to A17 3' phosphate.

Figure 16:
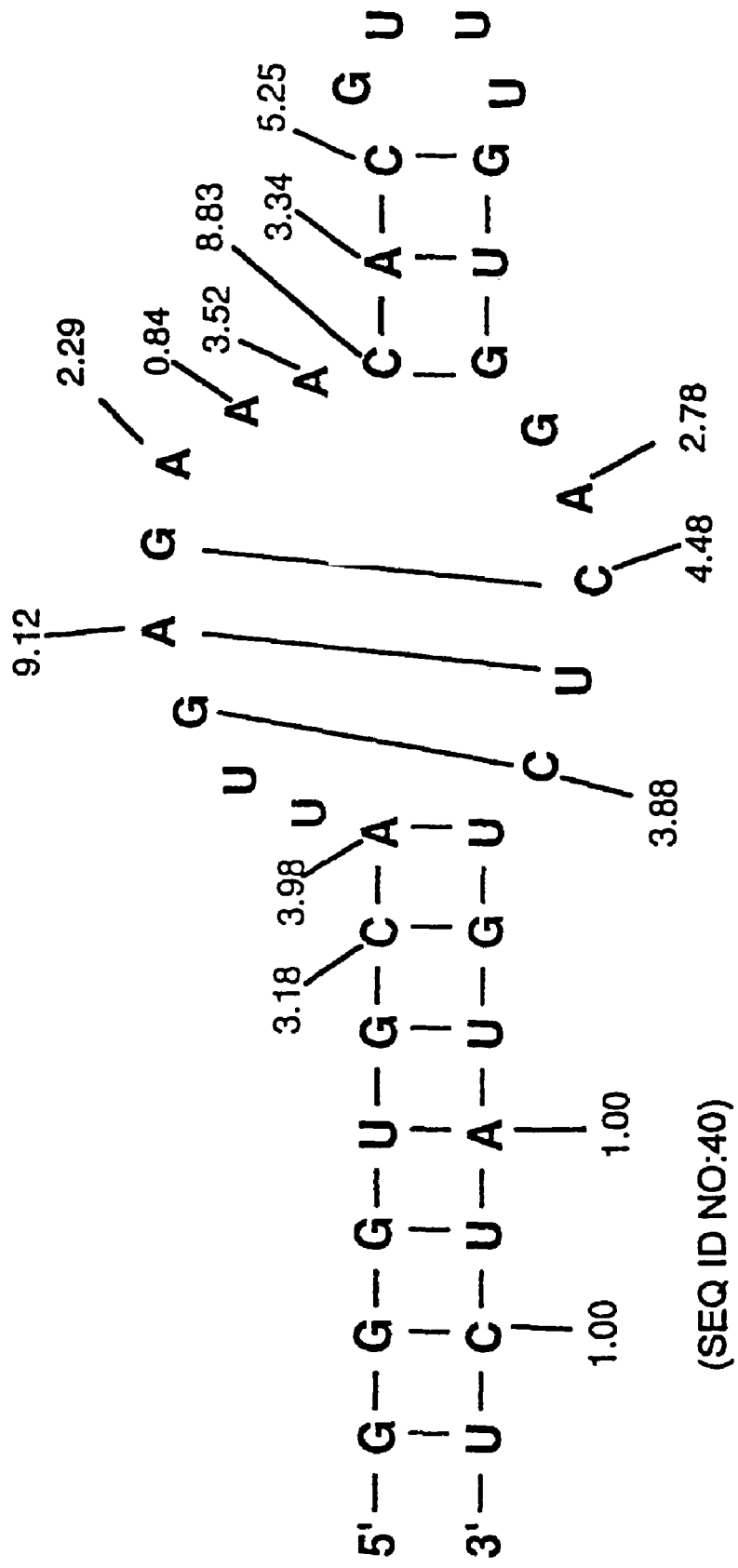

FIG. 16 depicts the modification interference values for DMS modification of N3C and N1A. Data is normalized to C36; A34.

Figure 17:
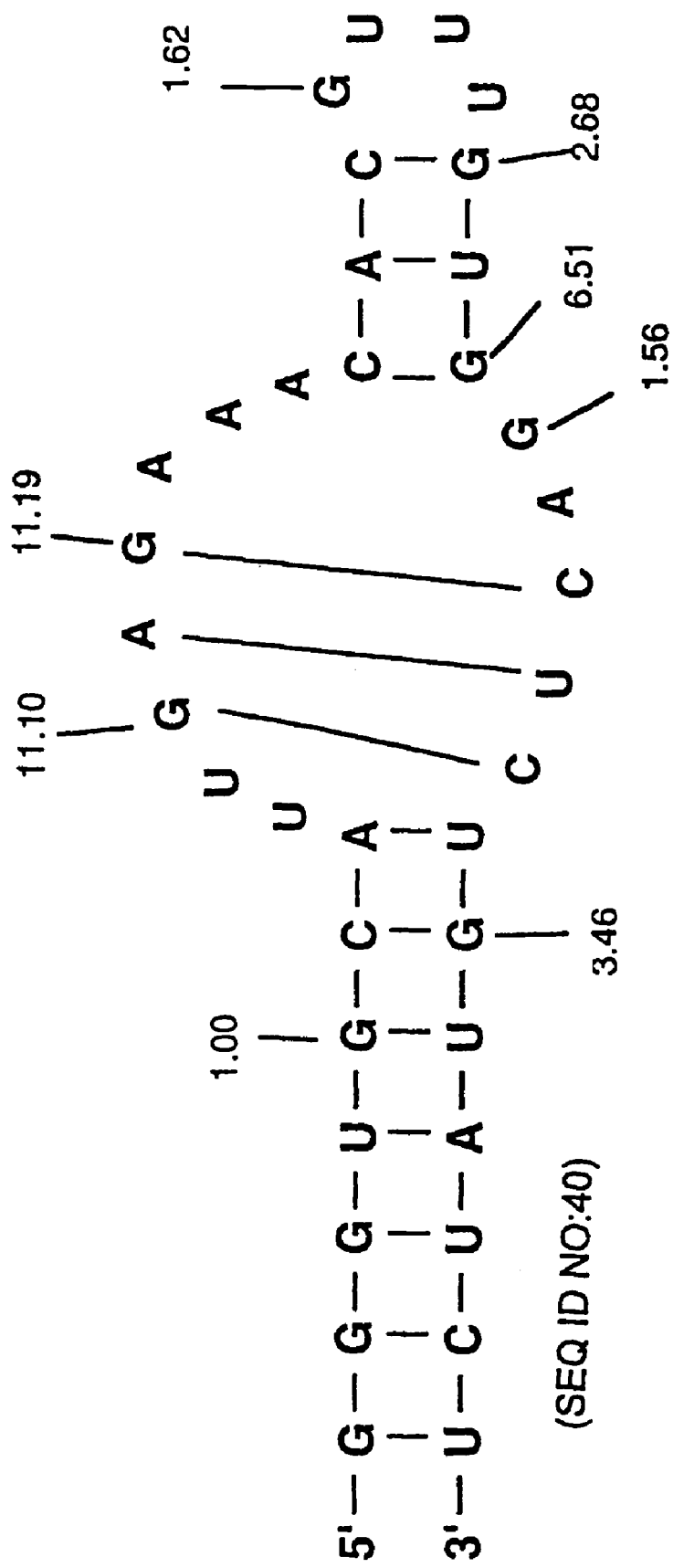

FIG. 17 depicts the modification interference values for kethoxal modification of N1G and N2G. Data is normalized to G5.

Figure 18:
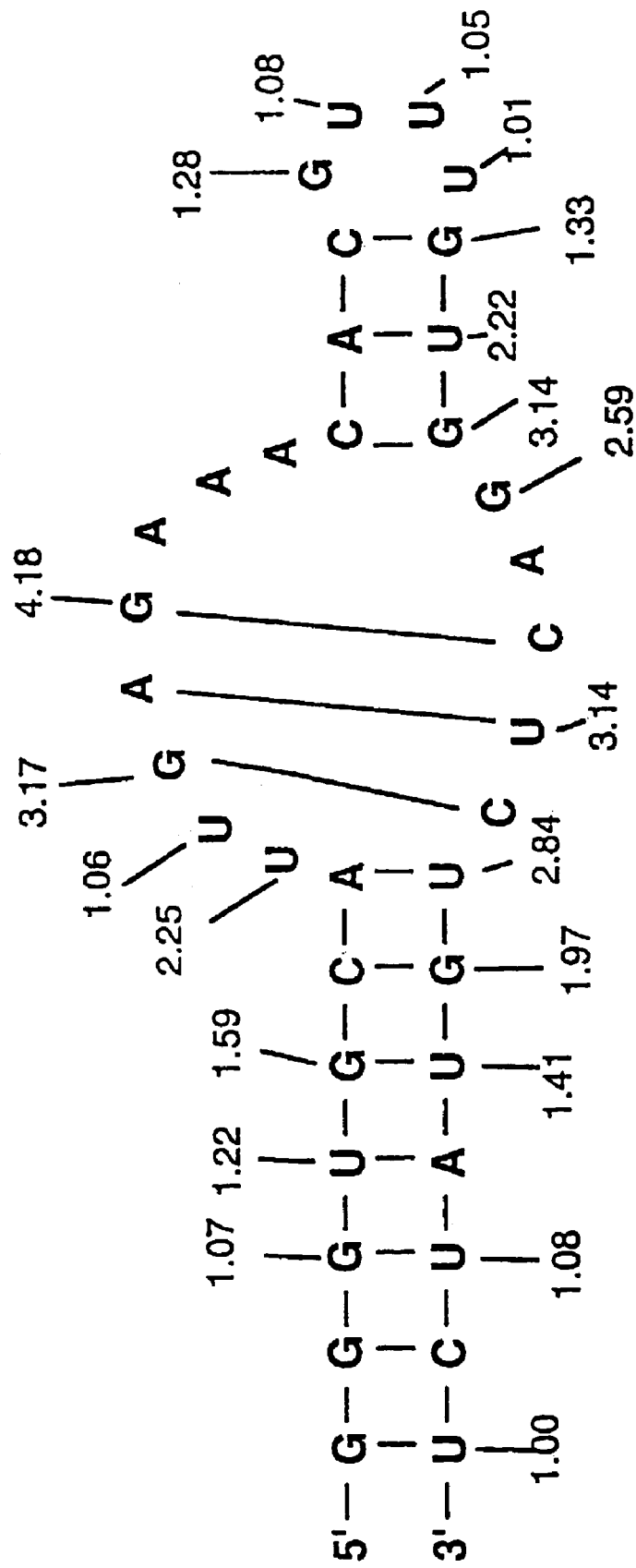

FIG. 18 depicts the modification interference values for CMCT modification of N3U and N1G. Data is normalized to U38.

Figure 19:
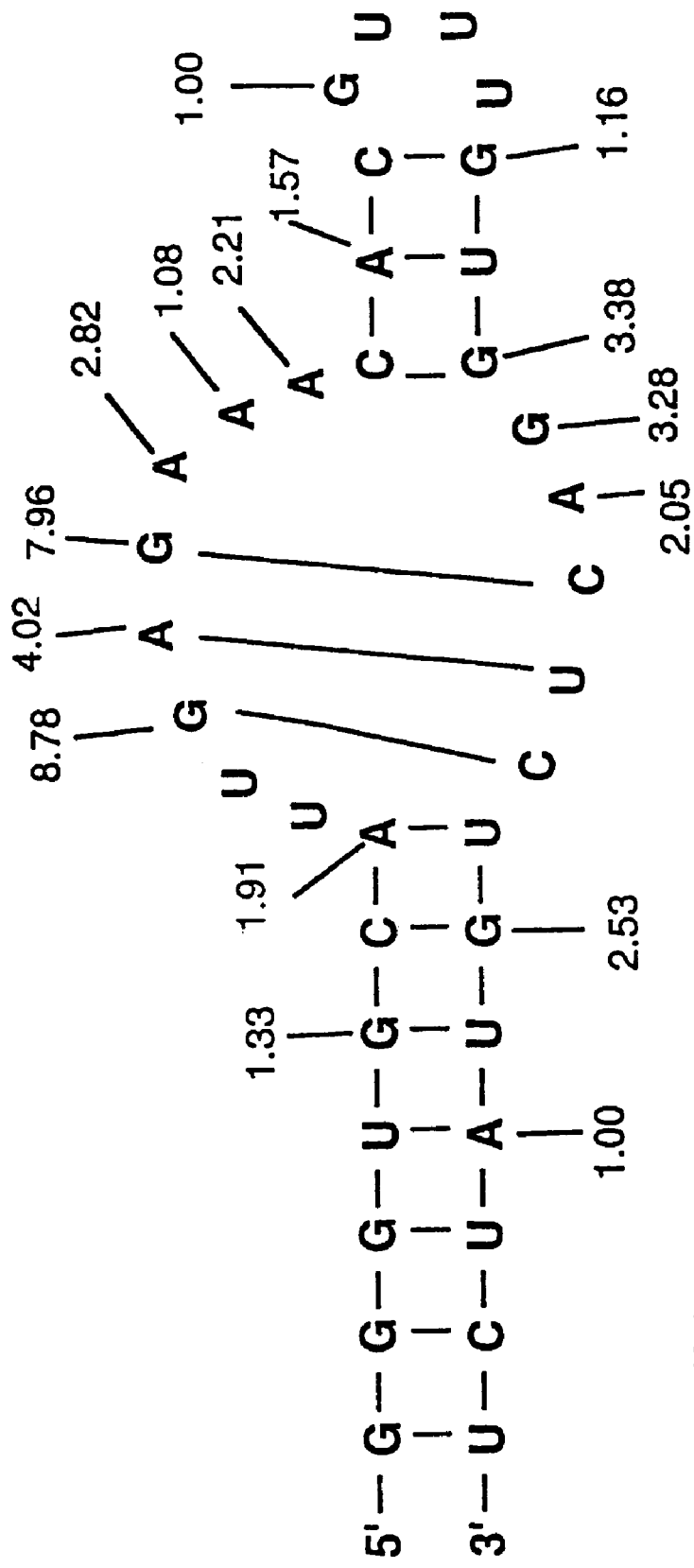

FIG. 19 depicts the modification interference values for DEPC modification of N7A and N7G. Data normalized to G19; A34.

Figure 20:
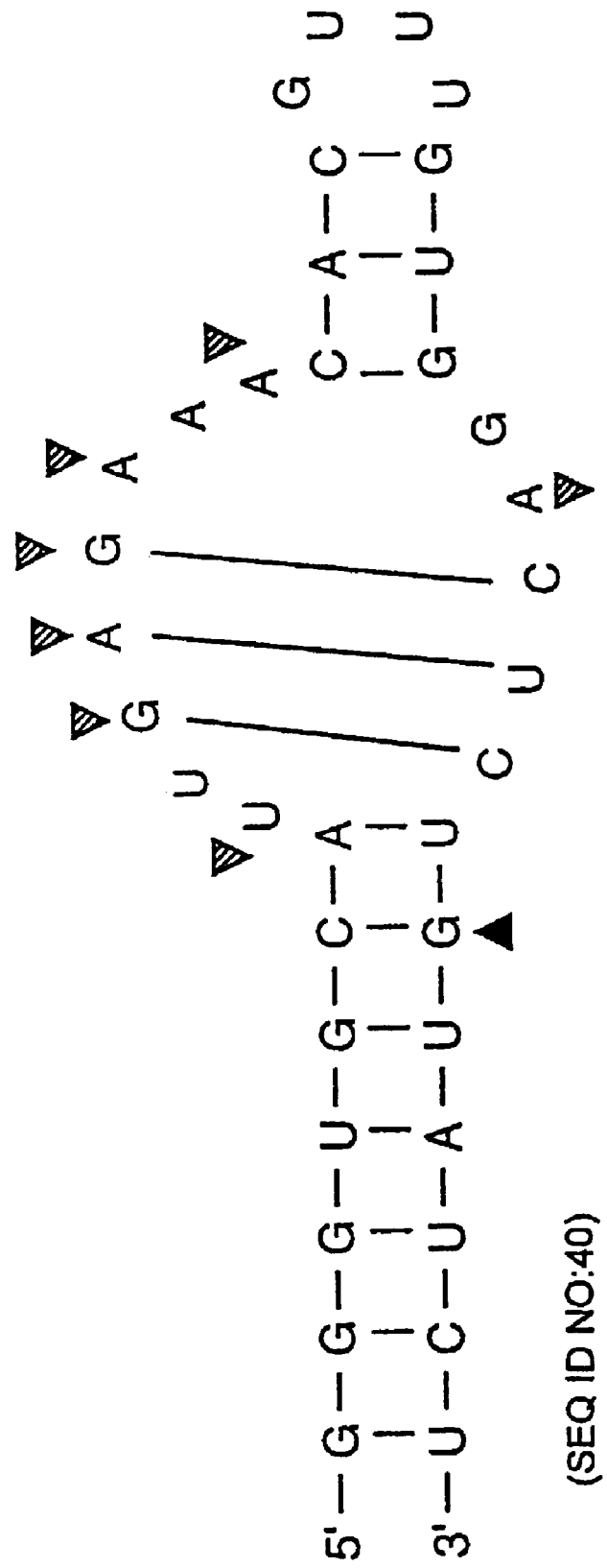
Figures 1, 22A:
Figures 1, 22B:
Figures 2, 22A:
Figures 2, 22B:
Figures 1, 22C:
Figures 2, 22C:

FIG. 20 depicts the chemical modification of the RNA ligand in the presence of the HIV-1 Rev protein. Indicated are those positions that showed either reduced modification or enhanced modification in the presence of protein as compared to modification under native conditions but without protein present.

FIG. 21 shows the 5' and 3' sequences which flank the "6a" biased random region used in SELEX. The template which produced the initial RNA population was constructed from the following oligonucleotides:

```
5'-CCCGGATCCTCTTTACCTCTGTGTGagatacagagtccacaaacgtgttc      (SEQ ID NO:9)
tcaatgcacccGGTCGGAAGGCCATCAATAGTCCC-3'  (template oligo)

5'-CCGAAGCTTAATACGACTCACTATAGGGACTATTGATGGCCTTCCGACC-3'   (SEQ ID NO:10)
(5' primer)

5'-CCCGGATCCTCTTTACCTCTGTGTG-3'  (3' primer)                (SEQ ID NO:11)
``` where the small-case letters in the template oligo indicate that at each position that a mixture of reagents were used in synthesis by an amount of 62.5% of the small case letter, and 12.5% each of the other three nucleotides. Listed below the 6a sequence (SEQ ID NO:40) are the sequences of 38 isolates cloned after six rounds of SELEX performed with Rev protein with this population of RNA (SEQ ID NOS: 45-82). The differences found in these isolates from the 6a sequences are indicated by bold-faced characters. Underlined are the predicted base pairings that comprise the bulge-flanking stems of the Motif I Rev ligands. Bases that are included from the 5' and 3' fixed flanking sequences are lower case.

FIG. 22 shows three sets of tabulations containing:

A) The count of each nucleotide found at corresponding positions of the Rev 6a ligand sequence in the collection of sequences found in FIG. 21;
B) The fractional frequency of each nucleotide found at these positions (x÷38, where x is the count from 1.); and
C) The difference between the fractional frequency of B) and the expected frequency based on the input mixture of oligonucleotides during template synthesis [for "wild type" positions, (x÷38)−0.625 and for alternative sequences (x÷38)−0.125].

FIG. 23 shows three sets of tabulations containing:

A) The count of each base pair found at corresponding positions of the Rev 6a ligand sequence in the collection of sequences found in FIG. 21;
B) The fractional frequency of each nucleotide found at these positions (x÷38, where x is the count from A); and
C) The difference between the fractional frequency of B) and the expected frequency based on the input mixture of oligonucleotides during template synthesis [for "wild type" positions, (x÷38)−0.39; for base pairs that contain one alternate nucleotide and one wild type nucleotide, (x÷38)−0.078; and for base pairings of two alternate nucleotides (x÷38)−0.016]. Values are shown for purine pyrimidine pairings only, the other eight pyrimidine and purine pairings are collectively counted and shown as "other" and are computed for section C) as (x÷38)−0.252.

FIG. 24A shows the previously determined Rev protein ligand Motif I consensus (SEQ ID NO:83) from U.S. patent application Ser. No. 07/714,131, filed Jun. 10, 1991, entitled "Nucleic Acid Ligands," now U.S. Pat. No. 5,475,096, issued Dec. 12, 1995.

FIG. 24B shows the 6a sequence (SEQ ID NO:40) from the same application.

FIG. 24C shows the preferred consensus derived from the biased randomization SELEX as interpreted from the data presented in FIGS. 22 and 23 (SEQ ID NO:35). Absolutely conserved positions in the preferred consensus are shown in bold face characters, and S-S' indicates either a C-G or G-C base pair.

DETAILED DESCRIPTION OF THE PREFERRED EMBODIMENTS

This application is an extension and improvement of the method for identifying nucleic acid ligands referred to as SELEX™. The SELEX method is described in detail in U.S. patent application Ser. No. 07/714,13 1, filed Jun. 10, 1991, entitled "Nucleic Acid Ligands," now issued as U.S. Pat. No. 5,475,096 and U.S. patent application Ser. No. 07/536,428, filed Jun. 11, 1990, entitled "Systematic Evolution of Ligands by EXponential Enrichment," now abandoned. The full text of these applications, including but not limited to, all definitions and descriptions of the SELEX process, are specifically incorporated herein by reference in their entirety.

This application includes methods for identifying and producing improved nucleic acid ligands based on the basic SELEX process. The application includes separate sections covering the following embodiments of the invention: I. The SELEX Process; II. Techniques for Identifying Improved Nucleic Acid Ligands Subsequent to Performing SELEX; III. Sequential SELEX Experiments—Walking; IV. Elucidation of Structure of Ligands Via Covariance Analysis; V. Elucidation of an Improved Nucleic Acid Ligand for HIV-RT; VI. Performance of Walking Experiment With HIV-RT Nucleic Acid Ligand to Identify Extended Nucleic Acid Ligands; and VII. Elucidation of an Improved Nucleic Acid Ligand for HIV-1 Rev Protein.

Improved nucleic acid ligands to the HIV-RT and HIV-1 Rev proteins are disclosed and claimed herein. This invention includes the specific nucleic acid ligands identified herein. The scope of the ligands covered by the invention extends to all ligands of the HIV-RT and Rev proteins identified according to the procedures described herein. More specifically, this invention includes nucleic acid sequences that are substantially homologous to and that have substantially the same ability to bind the HIV-RT or Rev proteins, under physiological conditions, as the nucleic acid ligands identified herein. By substantially homologous, it is meant, a degree of homology in excess of 70%, most preferably in excess of 80%. Substantially homologous also includes base pair flips in those areas of the nucleic acid ligands that include base pairing regions. Substantially the same ability to bind the HIV-RT or Rev proteins means that the affinity is within two orders of magnitude of the affinity of the nucleic acid ligands described herein. It is well within the skill of those of ordinary skill in the art to determine whether a given sequence is substantially homologous to and has substantially the same ability to bind the HIV-RT or HIV-1 Rev proteins as the sequences identified herein.

I. The SELEX Process

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: a) to assist in the amplification steps described below; b) to facilitate mimicry of a sequence known to bind to the target; or c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100 percent).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target pairs between the target and the nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5-50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer unique sequences, and the average degree of affinity of the nucleic acids to the target will generally increase. Taken to its extreme, the SELEX process will yield a candidate mixture containing one or a small number of unique nucleic acids representing those nucleic acids from the original candidate mixture having the highest affinity to the target molecule.

The SELEX Patent Applications describe and elaborate on this process in great detail. Included are targets that can be used in the process; methods for the preparation of the initial candidate mixture; methods for partitioning nucleic acids within a candidate mixture; and methods for amplifying partitioned nucleic acids to generate enriched candidate mixtures. The SELEX Patent Applications also describe ligand solutions obtained to a number of target species, including both protein targets wherein the protein is and is not a nucleic acid binding protein.

SELEX delivers high affinity ligands of a target molecule. This represents a singular achievement that is unprecedented in the field of nucleic acids research. The present invention is directed at methods for taking the SELEX derived ligand solution in order to develop novel nucleic acid ligands having the desired characteristics. The desired characteristics for a given nucleic acid ligand may vary. All nucleic acid ligands are capable of forming a complex with the target species. In some cases, it is desired that the nucleic acid ligand will serve to inhibit one or more of the biological activities of the target. In other cases, it is desired that the nucleic acid ligand serves to modify one or more of the biological activities of the target. In other cases, the nucleic acid ligand serves to identify the presence of the target, and its effect on the biological activity of the target is irrelevant.

II. Techniques for Identifying Improved Nucleic Acid Ligands Subsequent to Performing SELEX In order to produce nucleic acids desirable for use as a pharmaceutical, it is preferred that the nucleic acid ligand 1) binds to the target in a manner capable of achieving the desired effect on the target; 2) be as small as possible to obtain the desired effect; 3) be as stable as possible; and 4) be a specific ligand to the chosen target. In most, if not all, situations it is preferred that the nucleic acid ligand have the highest possible affinity to the target. Modifications or derivatizations of the ligand that confer resistance to degradation and clearance in situ during therapy, the capability to cross various tissue or cell membrane barriers, or any other accessory properties that do not significantly interfere with affinity for the target molecule may also be provided as improvements. The present invention includes the methods for obtaining improved nucleic acid ligands after SELEX has been performed.

Assays of ligand effects on target molecule function. One of the uses of nucleic acid ligands derived by SELEX is to find ligands that alter target molecule function. Because ligand analysis requires much more work than is encountered during SELEX enrichments, it is a good procedure to first assay for inhibition or enhancement of function of the target protein. One could even perform such functional tests of the combined ligand pool prior to cloning and sequencing. Assays for the biological function of the chosen target are generally available and known to those skilled in the art, and can be easily performed in the presence of the nucleic acid ligand to determine if inhibition occurs.

Affinity assays of the ligands. SELEX enrichment will supply a number of cloned ligands of probable variable affinity for the target molecule. Sequence comparisons may yield consensus secondary structures and primary sequences that allow grouping of the ligand sequences into motifs. Although a single ligand sequence (with some mutations) can be found frequently in the total population of cloned sequences, the degree of representation of a single ligand sequence in the cloned population of ligand sequences may not absolutely correlate with affinity for the target molecule. Therefore mere abundance is not the sole criterion for judging "winners" after SELEX and binding assays for various ligand sequences (adequately defining each motif that is discovered by sequence analysis) are required to weigh the significance of the consensus arrived at by sequence comparisons. The combination of sequence comparison and affinity assays should guide the selection of candidates for more extensive ligand characterization.

Information boundaries determination. An important avenue for narrowing down what amount of sequence is relevant to specific affinity is to establish the boundaries of that information within a ligand sequence. This is conveniently accomplished by selecting end-labeled fragments from hydrolyzed pools of the ligand of interest so that 5' and 3' boundaries of the information can be discovered. To determine a 3' boundary, one performs a large-scale in vitro transcription of the PCRd ligand, gel purifies the RNA using UV shadowing on an intensifying screen, phosphatases the purified RNA, phenol extracts extensively, labels by kinasing with $^{32}$P, and gel purifies the labeled product (using a film of the gel as a guide). The resultant product may then be subjected to pilot partial digestions with RNase T1 (varying enzyme concentration and time, at 50° C. in a buffer of 7 M urea, 50 mM sodium citrate pH 5.2) and alkaline hydrolysis (at 50 mM $Na_2CO_3$, adjusted to pH 9.0 by prior mixing of 1M bicarbonate and carbonate solutions; test over ranges of 20 to 60 minutes at 95° C.). Once optimal conditions for alkaline hydrolysis are established (so that there is an even distribution of small to larger fragments) one can scale up to provide enough material for selection by the target (usually on nitrocellulose filters). One then sets up binding assays, varying target protein concentration from the lowest saturating protein concentration to that protein concentration at which approximately 10% of RNA is bound as determined by the binding assays for the ligand. One should vary target concentration (if target supplies allow) by increasing volume rather than decreasing absolute amount of target; this provides a good signal to noise ratio as the amount of RNA bound to the filter is limited by the absolute amount of target. The RNA is eluted as in SELEX and then run on a denaturing gel with T1 partial digests so that the positions of hydrolysis bands can be related to the ligand sequence.

The 5' boundary can be similarly determined. Large-scale in vitro transcriptions are purified as described above. There are two methods for labeling the 3' end of the RNA. One method is to kinase Cp with $^{32}$P (or purchase $^{32}$P-Cp) and ligate to the purified RNA with RNA ligase. The labeled RNA is then purified as above and subjected to very identical protocols. An alternative is to subject unlabeled RNAs to partial alkaline hydrolyses and extend an annealed, labeled primer with reverse transcriptase as the assay for band positions. One of the advantages over pCp labeling is the ease of the procedure, the more complete sequencing ladder (by dideoxy chain termination sequencing) with which one can correlate the boundary, and increased yield of assayable product. A disadvantage is that the extension on eluted RNA sometimes contains artifactual stops, so it may be important to control by spotting and eluting starting material on nitrocellulose filters without washes and assaying as the input RNA. The result is that it is possible to find the boundaries of the sequence information required for high affinity binding to the target.

An instructive example is the determination of the boundaries of the information found in the nucleic acid ligand for HIV-RT. (See U.S. patent application Ser. No. 07/714,131, filed Jun. 10, 1991, now issued as U.S. Pat. No. 5,475,096). These experiments are described in detail below. The original pool of enriched RNAs yielded a few specific ligands for HIV-RT (one ligand, 1.1, represented ¼ of the total population, nitrocellulose affinity sequences represented ½ and some RNAs had no affinity for either). Two high-affinity RT ligands shared the sequence . . . UUC-CGNNNNNNNNCGGGAAAA . . . (SEQ ID NO:1). Boundary experiments of both ligands established a clear 3' boundary and a less clear 5' boundary. It can be surmised from the boundary experiments and secondary SELEX experiments that the highest affinity ligands contained the essential information UCCGNNNNNNNNCGGGAAAAN'N'N'N' (SEQ ID NO:2) (where N's base pair to Ns in the 8 base loop sequence of the hairpin formed by the pairing of UCCG to CGGG) and that the 5' U would be dispensable with some small loss in affinity. In this application, the construction of model compounds confirmed that there was no difference in the affinity of sequences with only one 5' U compared to 2 5' U's (as is shared by the two compared ligands), that removal of both U's caused a 5-fold decrease in affinity and of the next C a more drastic loss in affinity. The 3' boundary which appeared to be clear in the boundary experiments was less precipitous. This new information can be used to deduce that what is critical at the 3' end is to have at least three base-paired nucleotides (to sequences that loop between the two strands of Stem 1). Only two base-paired nucleotides result in a 12-fold reduction in affinity. Having no 3' base-paired nucleotides (truncation at the end of Loop 2) results in an approximately 70-fold reduction in affinity.

Quantitative and Qualitative Assessment of Individual Nucleotide Contributions to Affinity.

SECONDARY SELEX. Once the minimal high affinity ligand sequence is identified, it may be useful to identify the nucleotides within the boundaries that are crucial to the interaction with the target molecule. One method is to create a new random template in which all of the nucleotides of a high affinity ligand sequence are partially randomized or blocks of randomness are interspersed with blocks of complete randomness. Such "secondary" SELEXes produce a pool of ligand sequences in which crucial nucleotides or structures are absolutely conserved, less crucial features preferred, and unimportant positions unbiased. Secondary SELEXes can thus help to further elaborate a consensus that is based on relatively few ligand sequences. In addition, even higher-affinity ligands may be provided whose sequences were unexplored in the original SELEX.

In this application we show such a biased randomization for ligands of the HIV-1 Rev protein. In U.S. patent application Ser. No. 07/714,131, filed Jun. 10, 1991, entitled, "Nucleic Acid Ligands," now issued as U.S. Pat. No. 5,475,096, nucleic acid ligands to the HIV-1 Rev protein were described. One of these ligand sequences bound with higher affinity than all of the other ligand sequences (Rev ligand sequence 6a, (SEQ ID NO:40) shown in FIG. 12), but existed as only two copies in the 53 isolates that were cloned and sequenced. In this application, this sequence was incorporated in a secondary SELEX experiment in which each of the nucleotides of the 6a sequence (confined to that part of the sequence which comprises a Rev protein binding site defined by homology to others of Rev ligand motif I) was mixed during oligonucleotide synthesis with the other three nucleotides in the ratio 62.5:12.5:12.5:12.5. For example, when the sequence at position G1 is incorporated during oligo synthesis, the reagents for G,A,T and C are mixed in the ratios 62.5:12.5:12.5:12.5. After six rounds of SELEX using the Rev protein, ligands were cloned from this mixture so that a more comprehensive consensus description could be derived.

NUCLEOTIDE SUBSTITUTION. Another method is to test oligo-transcribed variants where the SELEX consensus may be confusing. As shown above, this has helped in understanding the nature of the 5' and 3' boundaries of the information required to bind HIV-RT. As is shown in the attached example this has helped to quantitate the consensus of nucleotides within Stem 1 of the HIV-RT pseudoknot.

CHEMICAL MODIFICATION. Another useful set of techniques are inclusively described as chemical modification experiments. Such experiments may be used to probe the native structure of RNAs, by comparing modification patterns of denatured and non-denatured states. The chemical modification pattern of an RNA ligand that is subsequently bound by target molecule may be different from the native pattern, indicating potential changes in structure upon binding or protection of groups by the target molecule. In addition, RNA ligands will fail to be bound by the target molecule when modified at positions crucial to either the bound structure of the ligand or crucial to interaction with the target molecule. Such experiments in which these positions are identified are described as "chemical modification interference" experiments. There are a variety of available reagents to conduct such experiments that are known to those skilled in the art (see Ehresmann et al. (1987) Nucleic Acids Research 15:9109-9128).

Chemicals that modify bases can be used to modify RNA ligands. A pool is bound to the target at varying concentrations and the bound RNA recovered (much as in the boundary experiments) and the eluted RNA analyzed for the modification. Assay can be by subsequent modification-dependent base removal and aniline scission at the baseless position or by reverse transcription assay of sensitive (modified) positions. In such assays bands (indicating modified bases) in unselected RNA appear that disappear relative to other bands in target protein-selected RNA. Similar chemical modifications with ethylnitrosourea, or via mixed chemical or enzymatic synthesis with, for example, 2'-methoxys on ribose or phosphorothioates can be used to identify essential atomic groups on the backbone. In experiments with 2'-methoxy vs. 2'-OH mixtures, the presence of an essential OH group results in enhanced hydrolysis relative to other positions in molecules that have been stringently selected by the target.

An example of how chemical modification can be used to yield useful information about a ligand and help efforts to improve its functional stability is given below for HIV-RT. Ethylnitrosourea modification interference identified 5 positions at which modification interfered with binding and 2 of those positions at which it interfered drastically. Modification of various atomic groups on the bases of the ligand were also identified as crucial to the interaction with HIV-RT. Those positions were primarily in the 5' helix and bridging loop sequence that was highly conserved in the SELEX phylogeny (Stem I and Loop 2, FIG. 1). These experiments not only confirmed the validity of that phylogeny, but informed ongoing attempts to make more stable RNAs. An RT ligand was synthesized in which all positions had 2'-methoxy at the ribose portions of the backbone. This molecule bound with drastically reduced affinity for HIV-RT. Based on the early modification interference experiments and the SELEX phylogeny comparisons, it could be determined that the 3' helix (Stem II, FIG. 1) was essentially a structural component of the molecule. A ligand in which the 12 ribose residues of that helix were 2'-methoxy was then synthesized and it bound with high affinity to HIV-RT. In order to determine if any specific 2'-OHs of the remaining 14 residues were specifically required for binding, a molecule in which all of the riboses of the pseudoknot were synthesized with mixed equimolar (empirically determined to be optimal) reagents for 2'-OH and 2'-OMe formation. Selection by HIV-RT from this mixture followed by alkaline hydrolysis reveals bands of enhanced hydrolysis indicative of predominating 2' hydroxyls at those positions. Analysis of this experiment lead to the conclusion that residues (G4, A5, C13 and G14) must have 2'-OH for high affinity binding to HIV-RT.

Comparisons of the intensity of bands for bound and unbound ligands may reveal not only modifications that interfere with binding, but also modifications that enhance binding. A ligand may be made with precisely that modification and tested for the enhanced affinity. Thus chemical modification experiments can be a method for exploring additional local contacts with the target molecule, just as "walking" (see below) is for additional nucleotide level contacts with adjacent domains.

One of the products of the SELEX procedure is a consensus of primary and secondary structures that enables the chemical or enzymatic synthesis of oligonucleotide ligands whose design is based on that consensus. Because the replication machinery of SELEX requires that rather limited variation at the subunit level (ribonucleotides, for example), such ligands imperfectly fill the available atomic space of a target molecule's binding surface. However, these ligands can be thought of as high-affinity scaffolds that can be derivatized to make additional contacts with the target molecule. In addition, the consensus contains atomic group descriptors that are pertinent to binding and atomic group descriptors that are coincidental to the pertinent atomic group interactions. For example, each ribonucleotide of the pseudoknot ligand of HIV-RT contains a 2' hydroxyl group on the ribose, but only two of the riboses of the pseudoknot ligand cannot be substituted at this position with 2'-methoxy. A similar experiment with deoxyribonucleotide mixtures with ribonucleotide mixtures (as we have done with 2'-methoxy and 2' hydroxy mixtures) would reveal which riboses or how many riboses are dispensable for binding HIV-RT. A similar experiment with more radical substitutions at the 2' position would again reveal the allowable substitutions at 2' positions. One may expect by this method to find derivatives of the pseudoknot ligand that confer higher affinity association with HIV-RT. Such derivatization does not exclude incorporation of cross-linking agents that will give specifically directly covalent linkages to the target protein. Such derivatization analyses are not limited to the 2' position of the ribose, but could include derivatization at any position in the base or backbone of the nucleotide ligand.

A logical extension of this analysis is a situation in which one or a few nucleotides of the polymeric ligand is used as a site for chemical derivative exploration. The rest of the ligand serves to anchor in place this monomer (or monomers) on which a variety of derivatives are tested for non-interference with binding and for enhanced affinity. Such explorations may result in small molecules that mimic the structure of the initial ligand framework, and have significant and specific affinity for the target molecule independent of that nucleic acid framework. Such derivatized subunits, which may have advantages with respect to mass production, therapeutic routes of administration, delivery, clearance or degradation than the initial SELEX ligand, may become the therapeutic and may retain very little of the original ligand. This approach is thus an additional utility of SELEX. SELEX ligands can allow directed chemical exploration of a defined site on the target molecule known to be important for the target function.

Structure determination. These efforts have helped to confirm and evaluate the sequence and structure dependent association of ligands to HIV-RT. Additional techniques may be performed to provide atomic level resolution of ligand/target molecule complexes. These are NMR spectroscopy and X-ray crystallography. With such structures in hand, one can then perform rational design as improvements on the evolved ligands supplied by SELEX. The computer modeling of nucleic acid structures is described below.

Chemical Modification. This invention includes nucleic acid ligands wherein certain chemical modifications have been made in order to increase the in vivo stability of the ligand or to enhance or mediate the delivery of the ligand. Examples of such modifications include chemical substitutions at the ribose and/or phosphate positions of a given RNA sequence. (See, e.g., Cook et al. PCT Application WO 9203568; U.S. Pat. No. 5,118,672 of Schinazi et al.; Hobbs et al. (1973) Biochem. 12:5138; Guschlbauer et al. (1977) Nucleic Acids Research 4:1933; Shibahara et al. (1987) Nucleic Acids Research 15:4403; Pieken et al. (1991) Science 253:314, each of which is specifically incorporated herein by reference in its entirety).

III. Sequential SELEX Experiments—Walking

In one embodiment of this invention, after a minimal consensus ligand sequence has been determined for a given target, it is possible to add random sequence to the minimal consensus ligand sequence and evolve additional contacts with the target, perhaps to separate, adjacent domains of the target. This procedure is referred to as "walking" in the SELEX Patent Applications. The successful application of the walking protocol is presented below to develop an enhanced binding ligand to HIV-RT.

The walking experiment involves two SELEX experiments performed sequentially. A new candidate mixture is produced in which each of the members of the candidate mixture has a fixed nucleic acid region that corresponds to a SELEX-derived nucleic acid ligand. Each member of the candidate mixture also contains a randomized region of sequences. According to this method it is possible to identify what are referred to as "extended" nucleic acid ligands, that contain regions that may bind to more than one binding domain of a target.

IV. Elucidation of Structure of Ligands Via Covariance Analysis

In conjunction with the empirical methods for determining the three dimensional structure of nucleic acids, the present invention includes computer modeling methods for determining structure of nucleic acid ligands. Secondary structure prediction is a useful guide to correct sequence alignment. It is also a highly useful stepping-stone to correct 3D structure prediction, by constraining a number of bases into A-form helical geometry.

Tables of energy parameters for calculating the stability of secondary structures exist. Although early secondary structure prediction programs attempted to simply maximize the number of base-pairs formed by a sequence, most current programs seek to find structures with minimal free energy as calculated by these thermodynamic parameters. There are two problems in this approach. First, the thermodynamic rules are inherently inaccurate, typically to 10% or so, and there are many different possible structures lying within 10% of the global energy minimum. Second, the actual secondary structure need not lie at a global energy minimum, depending on the kinetics of folding and synthesis of the sequence. Nonetheless, for short sequences, these caveats are of minor importance because there are so few possible structures that can form.

The brute force predictive method is a dot-plot: make an N by N plot of the sequence against itself and mark an X everywhere a basepair is possible. Diagonal runs of X's mark the location of possible helices. Exhaustive tree-searching methods can then search for all possible arrangements of compatible (i.e., non-overlapping) helices of length L or more. Energy calculations may be done for these structures to rank them as more or less likely. The advantages of this method are that all possible topologies, including pseudoknotted conformations, may be examined, and that a number of suboptimal structures are automatically generated as well. The disadvantages of the method are that it can run in the worst cases in time proportional to an exponential factor of the sequence size, and may not (depending on the size of the sequence and the actual tree search method employed) look deep enough to find a global minimum.

The elegant predictive method, and currently the most used, is the Zuker program. (Zuker (1989) Science 244:48-52). Originally based on an algorithm developed by Ruth Nussinov, the Zuker program makes a major simplifying assumption that no pseudoknotted conformations will be allowed. This permits the use of a dynamic programming approach which runs in time proportional to only $N^3$ to $N^4$, where N is the length of the sequence. The Zuker program is the only program capable of rigorously dealing with sequences of more than a few hundred nucleotides, so it has come to be the most commonly used by biologists. However, the inability of the Zuker program to predict pseudoknotted conformations is a fatal flaw, in that several different SELEX experiments so far have yielded pseudoknotted RNA structures, which were recognized by eye. A brute-force method capable of predicting pseudoknotted conformations must be used.

The central element of the comparative sequence analysis of the present invention is sequence covariations. A covariation is when the identity of one position depends on the identity of another position; for instance, a required Watson-Crick base pair shows strong covariation in that knowledge of one of the two positions gives absolute knowledge of the identity at the other position. Covariation analysis has been used previously to predict the secondary structure of RNAs for which a number of related sequences sharing a common structure exist, such as tRNA, rRNA, and group I introns. It is now apparent that covariation analysis can be used to detect tertiary contacts as well. Stormo and Gutell (1992) Nucleic Acids Research 29:5785-95, have designed and implemented an algorithm that precisely measures the amount of covariations between two positions in an aligned sequence set. The program is called "MIXY"—Mutual Information at position X and Y.

Consider an aligned sequence set. In each column or position, the frequency of occurrence of A, C, G, U and gaps is calculated. Call this frequency $f(b_x)$, the frequency of base b in column x. Now consider two columns at once. The frequency that a given base b appears in column x is $f(b_x)$ and the frequency that a given base b appears in column y is $f(b_y)$. If position x and position y do not care about each other's identity—that is, the positions are independent; there is no covariation—the frequency of observing bases $b_x$ and $b_y$ at position x and y in any given sequence should be just $f(b_x b_y)=f(b_x)f(b_y)$. If there are substantial deviations of the observed frequencies of pairs from their expected frequencies, the positions are said to covary. The amount of deviation from expectation may be quantified with an information measure $M(x,y)$, the mutual information of x and y:

$$M(x, y) = \sum f(b_x b_y) \ln \frac{f(b_x b_y)}{b_x b_y \; f(b_x) f(b_y)}$$

M(x,y) can be described as the number of bits of information one learns about the identity of position y from knowing just the identity of position y from knowing just the identity of position x. If there is no covariation, M(x,y) is zero; larger values of M(x,y) indicate strong covariation.

These numbers correlated extremely well to a probability for close physical contact in the tertiary structure, when this procedure was applied to the tRNA sequence data set. The secondary structure is extremely obvious as peaks in the M(x,y) values, and most of the tertiary contacts known from the crystal structure appear as peaks as well. These covariation values may be used to develop three-dimensional structural predictions.

In some ways, the problem is similar to that of structure determination by NMR. Unlike crystallography, which in the end yields an actual electron density map, NMR yields a set of interatomic distances. Depending on the number of interatomic distances one can get, there may be one, few, or many 3D structures with which they are consistent. Mathematical techniques had to be developed to transform a matrix of interatomic distances into a structure in 3D space. The two main techniques in use are distance geometry and restrained molecular dynamics.

Distance geometry is the more formal and purely mathematical technique. The interatomic distances are considered to be coordinates in an N-dimensional space, where N is the number of atoms. In other words, the "position" of an atom is specified by N distances to all the other atoms, instead of the three (x,y,z) that we are used to thinking about. Interatomic distances between every atom are recorded in an N by N distance matrix. A complete and precise distance matrix is easily transformed into 3 by N Cartesian coordinates, using matrix algebra operations. The trick of distance geometry as applied to NMR is dealing with incomplete (only some of the interatomic distances are known) and imprecise (distances are known to a precision of only a few angstroms at best) data. Much of the time of distance geometry-based structure calculation is thus spent in pre-processing the distance matrix, calculating bounds for the unknown distance values based on the known ones, and narrowing the bounds on the known ones. Usually, multiple structures are extracted from the distance matrix which are consistent with a set of NMR data; if they all overlap nicely, the data were sufficient to determine a unique structure. Unlike NMR structure determination, covariance gives only imprecise distance values, but also only probabilistic rather than absolute knowledge about whether a given distance constraint should be applied.

Restrained molecular dynamics is a more ad hoc procedure. Given an empirical force field that attempts to describe the forces that all the atoms feel (van der Waals, covalent bonding lengths and angles, electrostatics), one can simulate a number of femtosecond time steps of a molecule's motion, by assigning every atom at a random velocity (from the Boltzmann distribution at a given temperature) and calculating each atom's motion for a femtosecond using Newtonian dynamical equations; that is "molecular dynamics." In restrained molecular dynamics, one assigns extra ad hoc forces to the atoms when they violate specified distance bounds.

In the present case, it is fairly easy to deal with the probabilistic nature of data with restrained molecular dynamics. The covariation values may be transformed into artificial restraining forces between certain atoms for certain distance bounds; varying the magnitude of the force according to the magnitude of the covariance.

NMR and covariance analysis generates distance restraints between atoms or positions, which are readily transformed into structures through distance geometry or restrained molecular dynamics. Another source of experimental data which may be utilized to determine the three dimensional structures of nucleic acids is chemical and enzymatic protection experiments, which generate solvent accessibility restraints for individual atoms or positions.

V. Elucidation of an Improved Nucleic Acid Ligand for HIV-RT

An example of the methods of the present invention are presented herein for the nucleic acid ligand for HIV-1 reverse transcriptase (HIV-RT). U.S. patent application Ser. No. 07/714,131, filed Jun. 10, 1991, entitled "Nucleic Acid Ligands," now issued as U.S. Pat. No. 5,475,096, describes the results obtained when SELEX was performed with the HIV-RT target. By inspection of the nucleic acid sequences that were found to have a high affinity to HIV-RT, it was concluded that the nucleic acid ligand solution was configured as a pseudoknot.

Described herein are experiments which establish the minimum number of sequences necessary to represent the nucleic acid ligand solution via boundary studies. Also described are the construction of variants of the ligand solution which are used to evaluate the contributions of individual nucleotides in the solution to the binding of the ligand solution to HIV-RT. Also described is the chemical modification of the ligand solution; 1) to corroborate its predicted pseudoknot structure; 2) to determine which modifiable groups are protected from chemical attack when bound to HIV-RT (or become unprotected during binding); and 3) to determine what modifications interfere with binding to HIV-RT (presumably by modification of the three dimensional structure of the ligand solution) and, therefore, which are presumably involved in the proximal contacts with the target.

Figure 1:
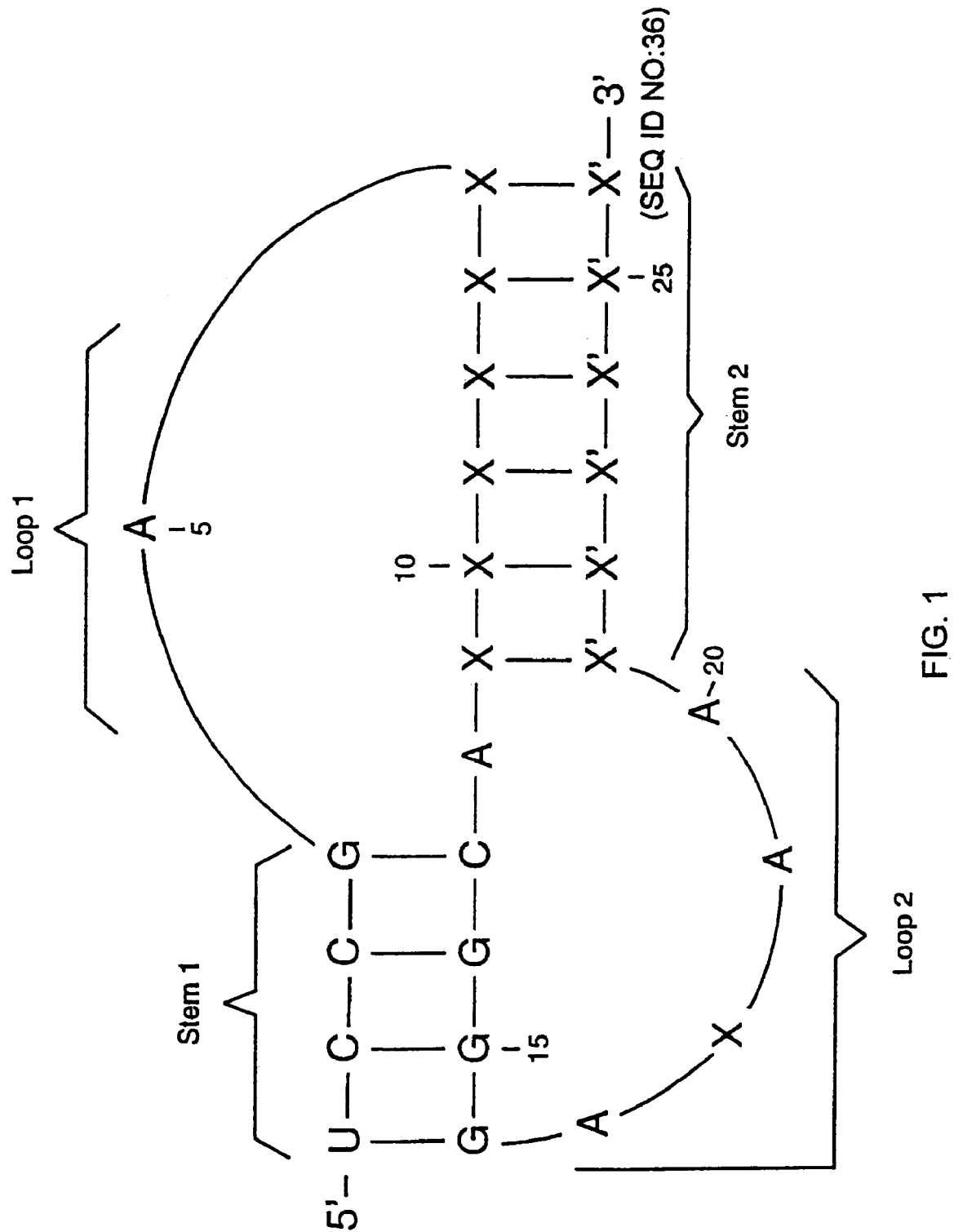
FIG. 1 depicts the consensus pseudoknot derived from primary and secondary SELEX experiments describing high affinity inhibitory ligands of HIV-1 reverse transcriptase (HIV-RT). The consensus secondary structure is a pseudoknot; the 5' helix of that pseudoknot (Stem 1) is conserved at the primary sequence level and the 3' helix or Stem 2 is not. X indicates a nucleotide position that is non-conserved; X-X' indicates a preferred base-pair. The 26 nucleotide positions are numbered as shown.

The nucleic acid ligand 6a (SEQ ID NO:40) previously determined is shown in FIG. 1. Depicted is an RNA pseudoknot in which Stem 1 (as labeled) is conserved and Stem 2 is relatively non-conserved; X indicates no conservation and X' base-pairs to X. In the original SELEX consensus U1 was preferred (existing at this relative position in 11 of the 18 sequences that contributed to the consensus), but A1 was also found frequently (in 6 of the 18). There were two sequences in which C-G was substituted for the base-pair of G4-C 13 and one A-U substitution. The preferred number of nucleotides connecting the two strands of Stem 1 was eight (in 8 of 18). The number and pattern of base-paired nucleotides comprising Stem 2 and the preference for A5 and A12 were derived from the consensus of a secondary SELEX in which the random region was constructed as follows NNUUCCGNNNNNNNNCGGGAAAANNNN (SEQ ID NO:3) (Ns are randomized). One of the ligands was found to significantly inhibit HIV-RT and failed to inhibit AMV or MMLV reverse transcriptases.

Refinement of the information boundaries. The first two SELEX experiments in which 32 nucleotide positions were randomized provided high affinity ligands in which there was variable length for Stem 1 at its 5' end; that is, some ligands had the sequence UUCCG which could base pair to CGGGA, UCCG to CGGG or CCG to CGG. Determination of the boundaries of the sequences donating high-affinity to the interaction with HIV-RT was accomplished by selection from partial alkaline hydrolysates of end-labeled clonal RNAs, a rapid but qualitative analysis which suggested that the highest affinity ligands contained the essential information UCCGNNNNNNNNCGGGAAAAN'N'N'N' (SEQ ID NO:2) (where N's base pair to Ns in the 8 base loop sequence of the hairpin formed by the pairing of UCCG to CGGG) and that the 5' U would be dispensable with some small loss in affinity. In order to more stringently test the 5' sequences in a homogeneous context, the binding experiments depicted in FIG. 2 were performed. The RNA's transcribed from oligonucleotide templates were all the same as the complete sequence shown in the upper right hand corner of the figure, except for the varying 5' ends as shown in the boxes A-E lining the left margin. The result is that one 5' U is sufficient for the highest-affinity binding to HIV-RT (boxes A and B), that with no U there is reduced binding (box C), and that any further removal of 5' sequences reduces binding to that of non-specific sequences (box D). The design (hereafter referred to as ligand B) with only one 5' U (U1) was used for the rest of the experiments described here.

Dependence on the length of Stem 2 was also examined by making various 3' truncations at the 3' end of ligand B. Deletion of as many as 3 nucleotides from the 3' end (A24-U26) made no difference in affinity of the molecule for HIV-RT. Deletion of the 3'-terminal 4 nucleotides (C23-U26) resulted in 7-fold reduced binding, of 5 (G22-U26) resulted in approximately 12-fold reduction and of 6 nucleotides (U21-U26, or no 3' helix) an approximately 70-fold reduction in affinity. Such reductions were less drastic than reductions found for single-base substitutions reported below, suggesting (with other data reported below) that this helix serves primarily a structural role that aids the positioning of crucial groups in Loop 2.

Figure 3:
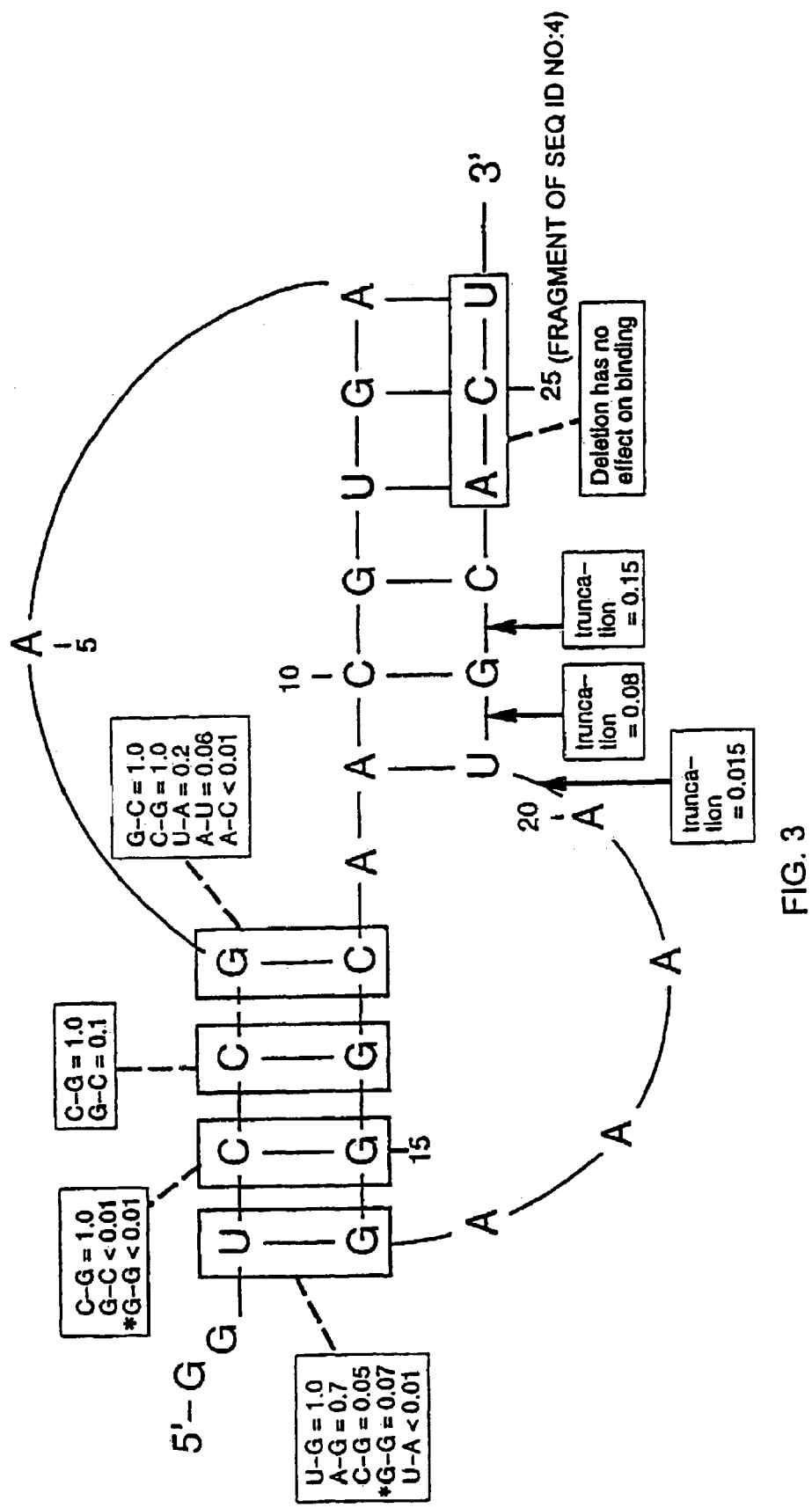
FIG. 3 depicts the effect of various nucleotide substitutions within the ligand B sequence on binding to HIV-RT. Illustrated are the various substitutions and resultant affinities to HIV-RT expressed relative to the binding of ligand B. Ligand B was a control tested in each experiment; the affinity of ligand B is normalized as 1.0 and the relative affinity (Kd of ligand B divided by the Kd of each ligand) is shown. Also shown are the affinities of various truncations of ligand B. The value associated with the asterisked G-G which replaces U1-G16 comes from ligand C of FIG. 2.

Testing the SELEX consensus for Stem 1. Various nucleotide substitutions in the conserved Stem 1 were prepared and their affinity to HIV-RT determined. As shown in FIG. 3, substitution of an A for U1 in model RNAs made little difference in affinity for HIV-RT. C (which would increase the stability of Stem I) or G (represented by the U deletion experiment above) at this position resulted in approximately 20-fold lowering in affinity. Substitution of A for G16 (which would base-pair to U1) abolished specific binding. A G-C pair was substituted for C2-G15 which also abolished binding and for C3-G 14 which reduced binding about 10-fold. These two positions were highly conserved in the phylogeny of SELEX ligands. Various combinations were substituted for the G4-C 13 base pair. The order of affect of these on affinity were G4-C13=C-G>U-A>A-U>>>>A-C where A-U is about 20-fold reduced in affinity compared to G4-C 13 and A-C is at least 100-fold reduced. These results are consistent with the SELEX consensus determined previously.

Chemical probing of the pseudoknot structure. A number of chemical modification experiments were conducted to probe the native structure of ligand B, to identify chemical modifications that significantly reduced affinity of ligand B for HIV-RT, and to discover changes in structure that may accompany binding by HIV-RT. The chemicals used were ethylnitrosourea (ENU) which modifies phosphates, dimethyl sulfate (DMS) which modifies the base-pairing faces of C (at N3) and A (at N1), carbodiimide (CMCT) which modifies the base-pairing face of U (at N3) and to some extent G (at N1), diethylpyrocarbonate (DEPC) which modifies N7 of A and to a lesser extent the N7 of G, and kethoxal which modifies the base-pairing N1 and N2 of G. Most of the assays of chemical modification were done on a ligand B sequence which was lengthened to include sequences to which a labeled primer could be annealed and extended with AMV reverse transcriptase. Assay of ENU or DEPC modified positions were done on ligand B by respective modification-dependent hydrolysis, or modified base removal followed by aniline scission of the backbone at these sites.

Figure 4:
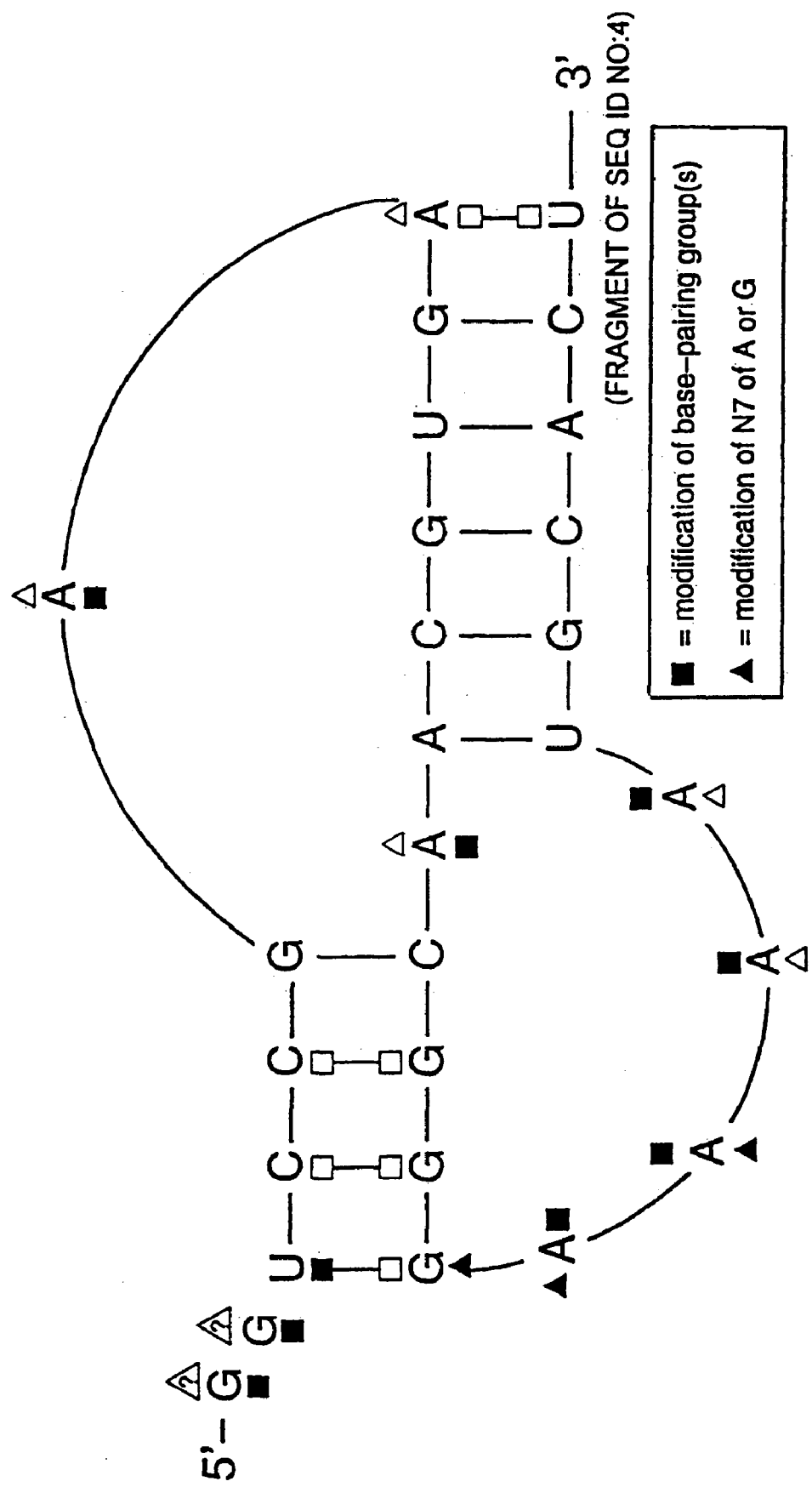
FIG. 4 depicts a chemical probe of the native versus denatured conformations of ligand B. The various nucleotides of ligand B were reacted with chemicals under native and denaturing conditions, assayed for the modified positions, electrophoresed and visualized for comparison. ■ indicate highly reactive base-pairing groups of the base at that position and □ partially reactivity; ∆ indicates strong reactivity of purine N7 positions and ∆ partial reactivity (to modification with DEPC). The question marks indicate that these positions on G(−2) and G(−1) could not be distinguished due to band crowding on the gel.

The results of probing the native structure as compared to modification of denatured ligand B are summarized in FIG. 4. The pattern of ENU modification was not different between denatured native states of the ligand suggesting that there is no stable involvement of the phosphates or N7 positions of purines in the solution structure of the pseudoknot. The other modification data suggest that Stem 2 forms rather stably and is resistant to any chemical modifications affecting the base-pairs shown, although the terminal A6-U26 is somewhat sensitive to modification indicating equilibration between base-paired and denatured states at this position. The single-stranded As (A5,A17,A18, A19 and A20) are fully reactive with DMS although A5, A19 and A20 are diminished in reactivity to DEPC. The base-pairs of Stem 1 seem to exhibit a gradation of resistance to modification such that G4-C13>C3-G14>C2-G15>U1-G16 where G4-C13 is completely resistant to chemical modification and U1-G16 is highly reactive. This suggests that this small helix of the pseudoknot undergoes transient and directional denaturation or "fraying."

Figure 5:
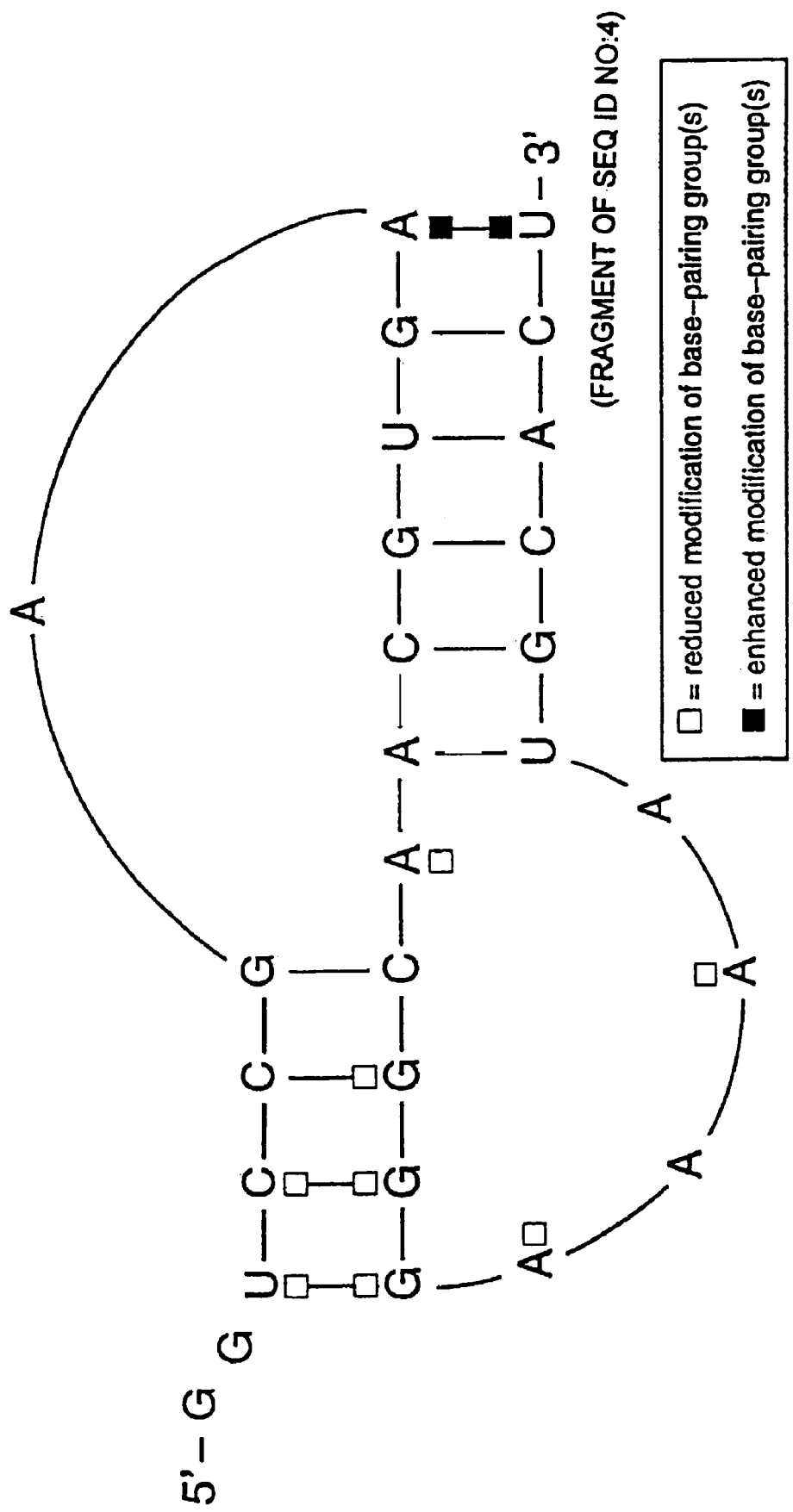
FIG. 5 depicts reactivities of modifiable groups of ligand B when bound to HIV-RT. Diagrammed are those groups that show altered reactivity when bound to HIV-RT as compared to that of the native conformation.

Protection of ligand B from chemical modification by HIV-RT. Binding of protein changes the fraying character of Helix I as shown in FIG. 5 either by stabilizing or protecting it. The natively reactive U1 is also protected upon binding. Binding of protein increases the sensitivity of the base-pair A6-U26 suggesting that this is unpaired in the bound state. This may be an indication of insufficient length of a single nucleotide Loop I during binding, either because it cannot bridge the bound Stem 1 to the end of Stem 2 in the native pseudoknot recognized by RT or because binding increases the length requirement of Loop I by changing the conformation from the native state. A17 and A19 of Loop II are also protected by binding to HIV-RT. In addition, the single base bridge A12 is protected upon binding.

Figure 6:
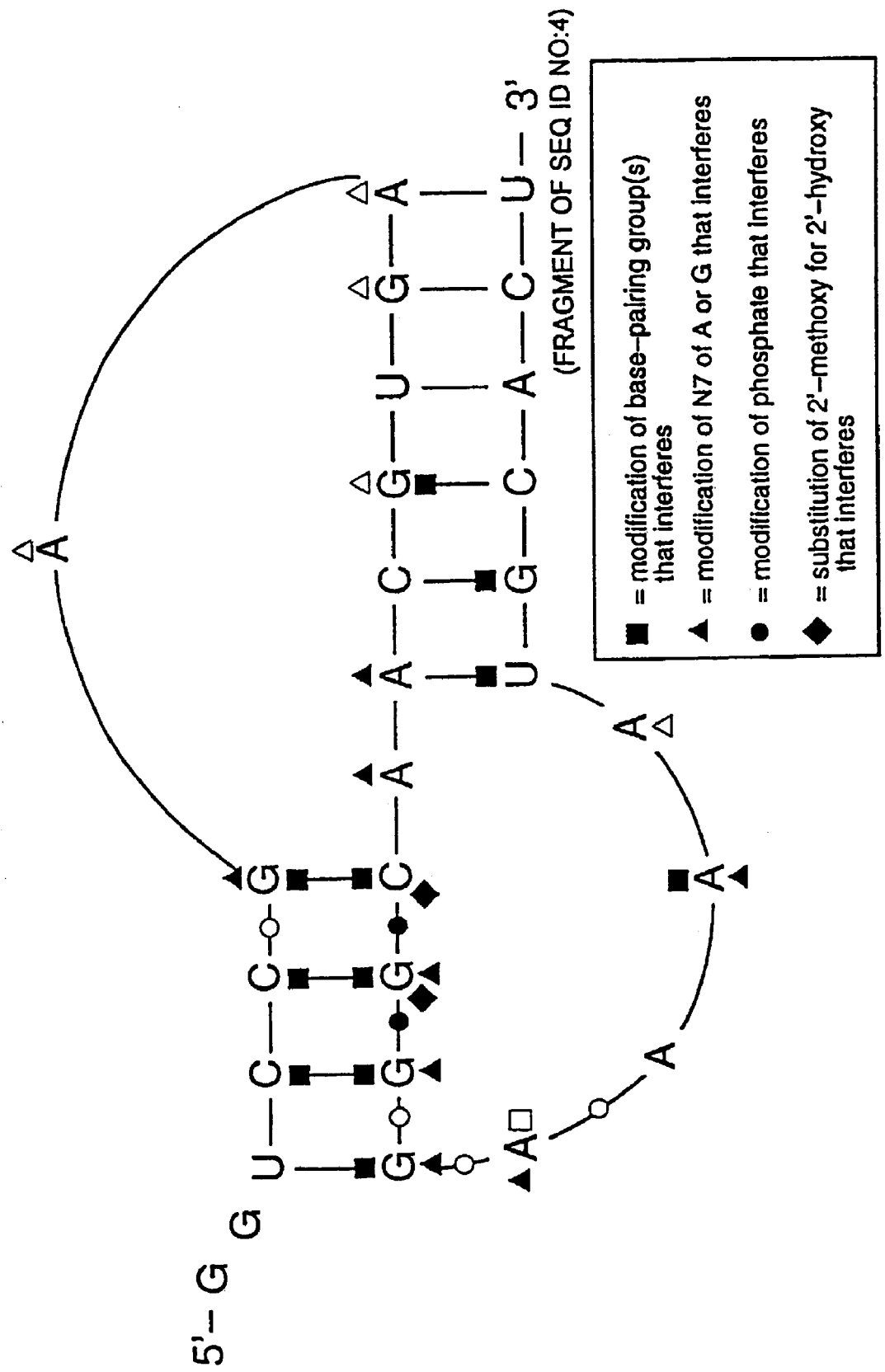
FIG. 6 depicts modification interference results for ligand B complexing with HIV-RT. Symbols for modification are as in the boxed legend. The modifications indicated are those that are strongly (filled symbols) or partially (unfilled symbols) selected against by binding to HIV-RT (reflected by decreased modification at those positions in the selected population).

Modification interference studies of the RT ligand B. The RNA ligand B was partially modified (with all of the chemicals mentioned above for structure determination). This modified population was bound with varying concentrations of the protein, and the bound species were assayed for the modified positions. From this, it can be determined where modification interferes with binding, and where there is no or little effect. A schematic diagram summarizing these modification interference results is shown in FIG. 6. As shown, most of the significant interference with binding is clustered on the left hand side of the pseudoknot which contains the Stem 1 and Loop 2. This is also the part of the molecule that was highly conserved (primary sequence) in the collection of sequences isolated by SELEX and where substitution experiments produced the most drastic reduction in binding affinity to HIV-RT.

Figure 7A:
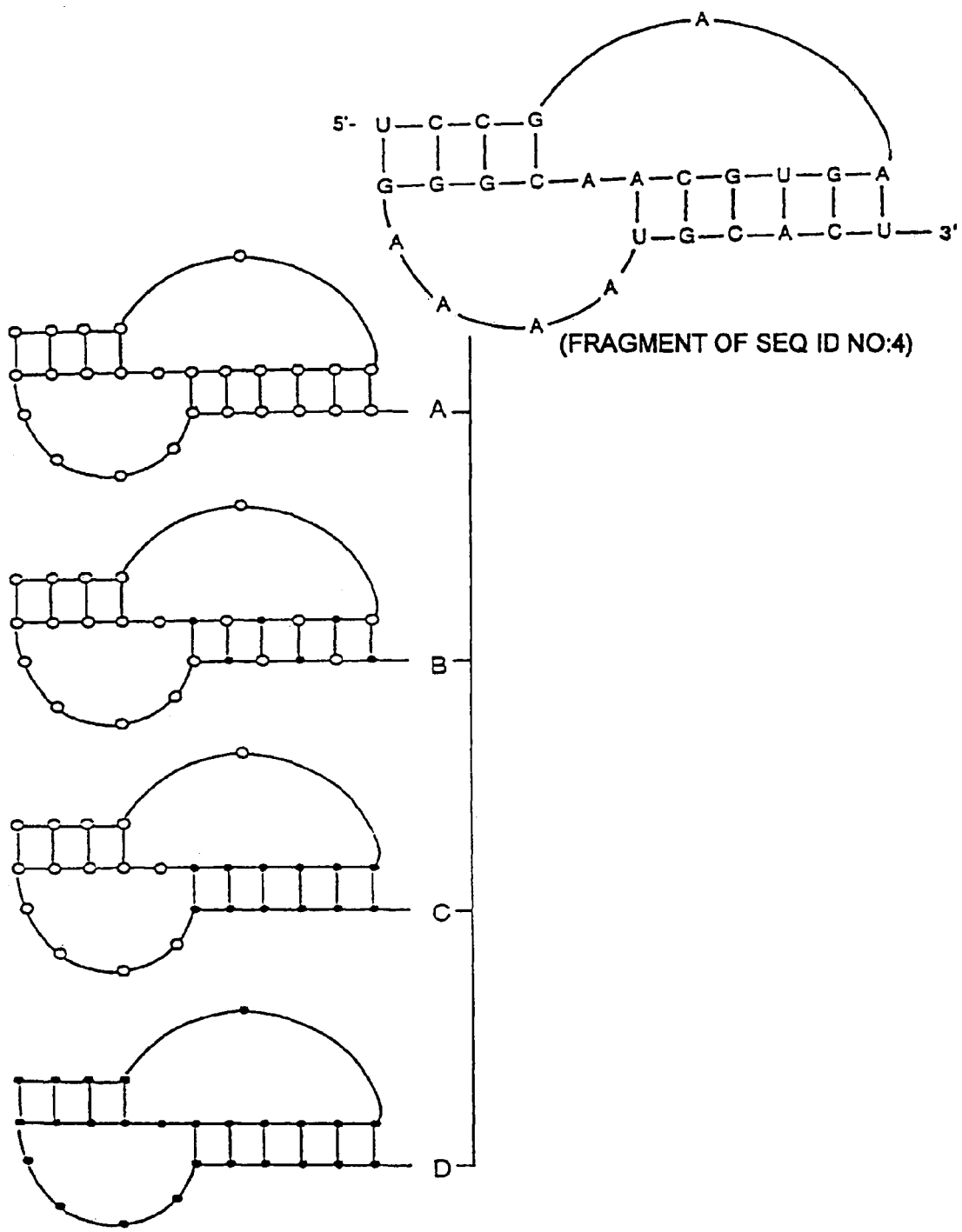
FIG. 7A depicts substitution of 2'-methoxy for the 2'-hydroxy on the riboses of the ligand B sequence shown in the upper right. Illustrated in the upper right is the complete ligand B. On the left margin are shown the variations in the individual ligands A through D that occur in ligand B.
Figure 7B:
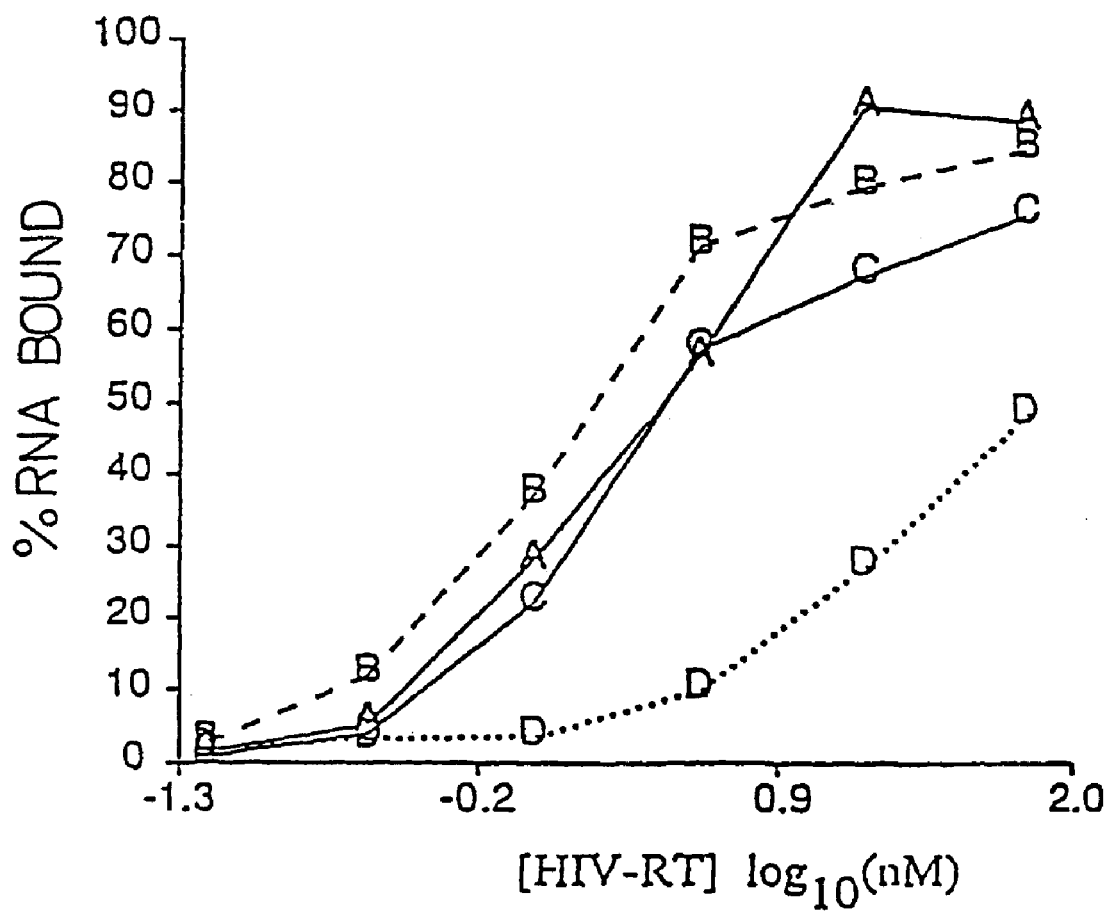
FIG. 7B depicts graphically the individual binding curves for ligands A-D.
Figure 8:
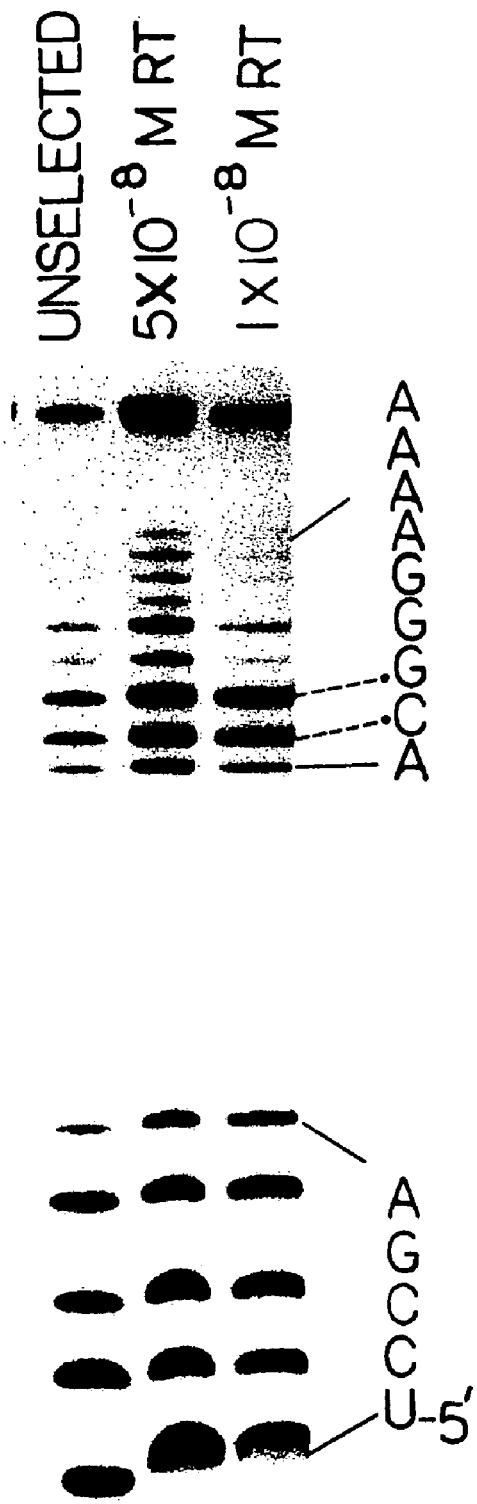
FIG. 8 depicts selection by HIV-RT from mixed populations of 2'-methoxy ribose versus 2'-hydroxyl at positions U1 through A5 and A12 through A20. An oligonucleotide was synthesized with the following sequence.

Substitution of 2'-methoxy for 2'-hydroxyl on riboses of ligand B. "RNA" molecules in which there is a 2'-methoxy bonded to the 2' carbon of the ribose instead of the normal hydroxyl group are resistant to enzymatic and chemical degradation. In order to test how extensively 2'-methoxys can be substituted for 2'-OH's in RT ligands, four oligos were prepared as shown in FIG. 7A. Because fully substituted 2'-methoxy ligand binds poorly (ligand D), and because it was determined that most of the modification interference sites were clustered at one end of the pseudoknot, subsequent attempts to substitute were confined to the non-specific 3' helix as shown in boxes B and C. Both of these ligands bind with high affinity to HIV-RT. Oligonucleotides were then prepared in which the allowed substitutions at the ribose of Stem 2 were all 2'-methoxy as in C of FIG. 7 and at the remaining 14 positions mixed synthesis were done with 2'-methoxy and 2'-OH phosphoramidite reagents. These oligos were subjected to selection by HIV-RT followed by alkaline hydrolysis of selected RNAs and gel separation (2'-methoxys do not participate in alkaline hydrolysis as do 2'-hydroxyls). As judged by visual inspection of films (see FIG. 8) and quantitative determination of relative intensities using an Ambis detection system (see Example below for method of comparison), the ligands selected by HIV-RT from the mixed incorporation populations showed significantly increased hydrolysis at positions C13 and G14 indicating interference by 2'-methoxys at these positions. In a related experiment where mixtures at all positions were analyzed in this way, G4, A5, C13 and G14 showed 2'-OMe interference.

The results of substitution experiments, quantitative boundary experiments and chemical probing experiments are highly informative about the nature of the pseudoknot inhibitor of HIV-RT and highlight crucial regions of contact on this RNA. These results are provided on a nucleotide by nucleotide basis below.

Figure 2A:
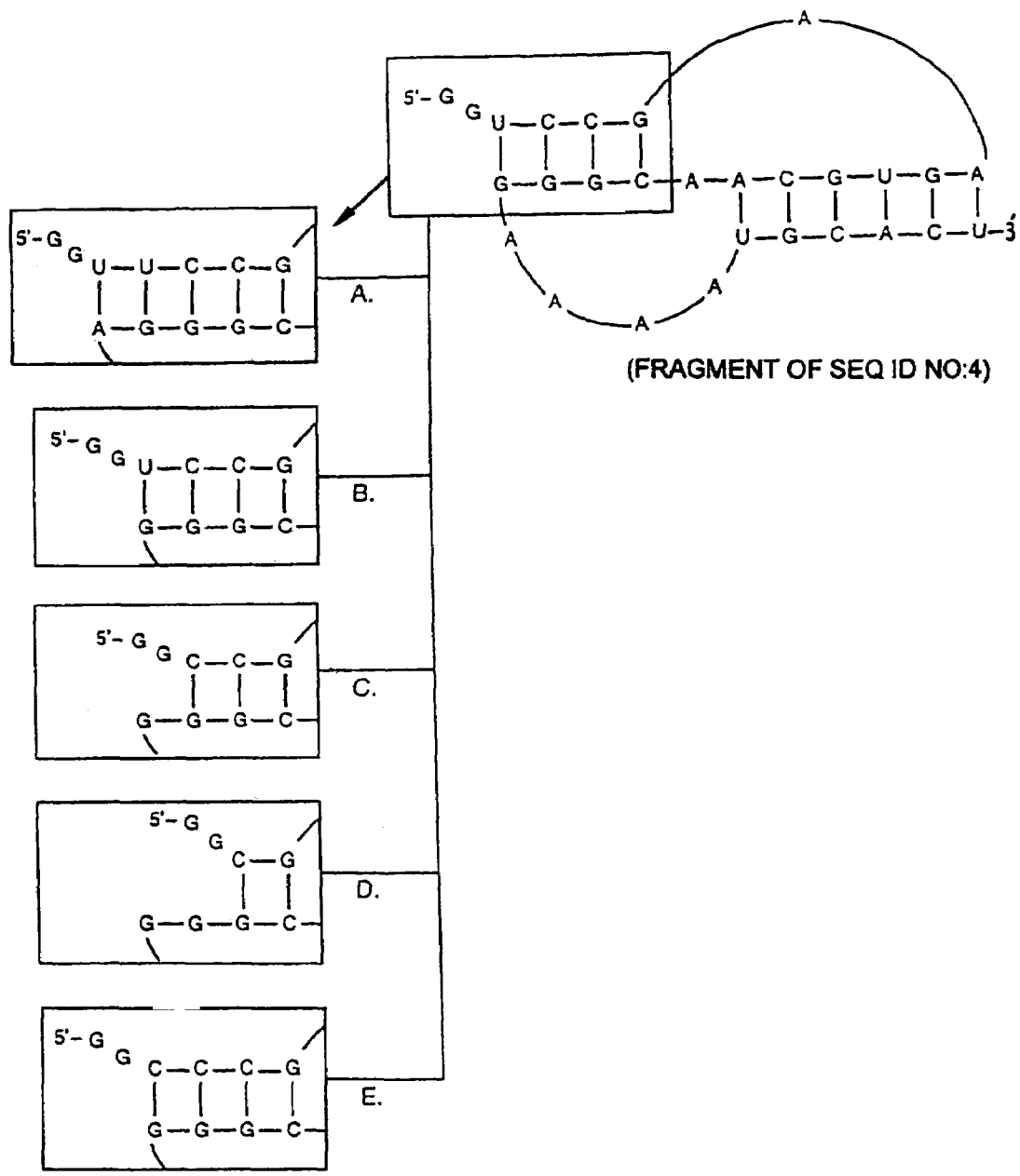
FIG. 2A depicts refinement of the 5' information boundary. A set of model ligands were synthesized with T7 RNA polymerase from template oligos. (Milligan et al. (1987) Nucl. Acid. Res. 15:8783-8798). Illustrated in the upper left is the complete ligand B. On the right margin are shown the variations in the individual ligands A through E that occur in the boxed areas.
Figure 2B:
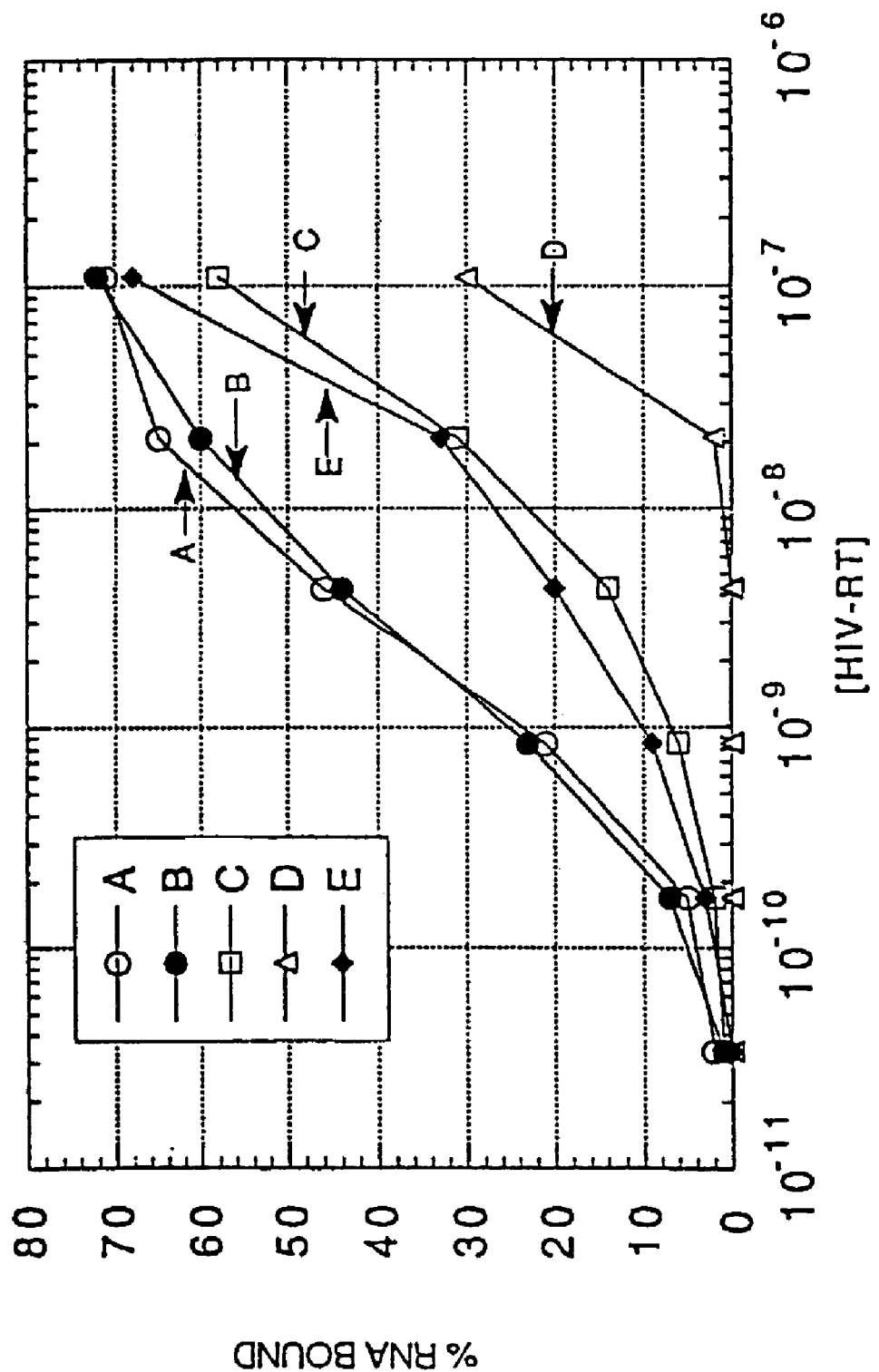
FIG. 2B depicts graphically the individual binding curves for these model ligands.

U1 can be replaced with A with little loss in affinity, but not by C or G. Although U1 probably makes transient base-pairing to G16, modification of U1-N3 with CMCT does not interfere with binding to HIV-RT. However, binding by HIV-RT protects the N3 of U1 perhaps by steric or electrostatic shielding of this position. Substitution with C which forms a more stable base-pair with G16 reduces affinity. Replacement of G16 with A which forms a stable U1-A16 pair abolishes specific affinity for HIV-RT and modification of G16-N1 strongly interferes with binding to HIV-RT. This modification of G16-N1 must prevent a crucial contact with the protein. Why G substitutions for U1 reduce affinity and A substitutions do not is not clear. Admittedly the G substitution is in a context in which the 5' end of the RNA is one nucleotide shorter, however synthetic RNAs in which U1 is the 5' terminal nucleotide bind with unchanged affinity from those in vitro transcripts with two extra Gs at the 5' end (FIG. 2B). Perhaps A at U1 replaces a potential U interaction with a similar or different interaction with HIV-RT a replacement that cannot be performed by C or G at this position.

The next base-pair of Stem 1 (C2-G15) cannot be replaced by a G-C base-pair without complete loss of specific affinity for HIV-RT. Modification of the base-pairing faces of either nucleotide strongly interferes with binding to HIV-RT and binding with HIV-RT protects from these modifications. Substitution of the next base-pair, C3-G14, with a G-C pair shows less drastic reduction of affinity, but modification is strongly interfering at this position. Substitution of a C-G pair for G4-C13 has no effect on binding, and substitution of the less stable A-U and U-A pairs allow some specific affinity. Substitution of the non-pairing A-C for these positions abolishes specific binding. This correlates with the appearance of C-G substitutions and one A-U substitution in the original SELEX phylogeny at this position, the non-reactivity of this base-pair in the native state, and the high degree of modification interference found for these bases.

The chemical modification data of Loop 2 corroborate well the phylogenetic conservation seen in the original SELEX experiments. Strong modification interference is seen at positions A17 and A19. Weak modification interference occurs at A20 which correlates with the finding of some Loop 2's of the original SELEX that are deleted at this relative position (although the chemical interference experiments conducted do not exhaustively test all potential contacts that a base may make with HIV-RT). A18 is unconserved in the original SELEX and modification at this position does not interfere, nor is this position protected from modification by binding to HIV-RT.

Taken together the above data suggest that the essential components of Stem 1 are a single-stranded 5' nucleotide (U or A) which may make sequence specific contact with the protein and a three base-pair helix (C2-G15, C3-G14, G4-C13) where there are sequence-specific interactions with the HIV-RT at the first two base-pairs and a preference for a strong base-pair (i.e. either C-G or G-C) at the third loop closing position of G4-C13. Loop 2 should be more broadly described as GAXAA (16-20) due to the single-stranded character of G16 which probably interacts with HIV-RT in a sequence-specific manner, as likely do A17 and A19. Stem 2 varies considerably in the pattern and number of base-pairing nucleotides, but from 3' deletion experiments reported here one could hypothesize that a minimum of 3 base-pairs in Stem 2 are required for maximal affinity. Within the context of eight nucleotides connecting the two strands comprising the helix of Stem 1, at least 2 nucleotides are required in Loop 1 of the bound ligand.

The revised ligand description for HIV-RT obtained based on the methods of this invention is shown in FIG. 11 (SEQ ID NO:12). The major differences between that shown in FIG. 1 (which is based on the original and secondary SELEX consensuses) is the length of Stem 2, the more degenerate specification of the base-pair G4-C13, the size of Loop 1 (which is directly related to the size of Stem 2) and the single-stranded character of U 1 and G16. How can these differences be reconciled? Although not limited by theory, the SELEX strategy requires 5' and 3' fixed sequences for replication. In any RNA sequence, such additional sequences increase the potential for other conformations that compete with that of the high-affinity ligand. As a result, additional structural elements that do not directly contribute to affinity, such as a lengthened Stem 2, may be selected. Given that the first two base pairs of Stem 1 must be C-G because of sequence-specific contacts the most stable closing base-pair would be G4-C13 (Freier et al. (1986) Proc. Natl: Acad. Sci. USA, 83:9373-9377) again selected to avoid conformational ambiguity. The sequence-specific selection of U1 and G16 may be coincidental to their ability to base-pair; in other nucleic acid ligand-protein complexes such as Klenow fragment/primer-template junction and tRNA/tRNA synthetase there is significant local denaturation of base-paired nucleotides (Freemont et al. (1988) Proc. Natl. Acad. Sci. USA 85:8924; Ronald et al. (1989) Science 246:1135), which may also occur in this case.

VI. Performance of Walking Experiment with HIV-RT Nucleic Acid Ligand to Identify Extended Nucleic Acid Ligands It had previously been found that fixed sequences (of 28 nucleotides) placed 5' to the pseudoknot consensus ligand reduced the affinity to HIV-RT and that sequences (of 31 nucleotides) added 3' to the ligand increased that affinity. A SELEX experiment was therefore performed in which a 30 nucleotide variable region was added 3' to the ligand B sequence to see if a consensus of higher affinity ligands against HIV-RT could be obtained. Individual isolates were cloned and sequenced after the sixteenth round. The sequences are listed in FIG. 9 (SEQ ID NOS: 14-33) grouped in two motifs. A schematic diagram of the secondary structure and primary sequence conservation of each motif is shown in FIG. 10. The distance between the RNase H and polymerase catalytic domains of HIV-RT has recently been determined to be on the order of 18 base-pairs of an A-form RNA-DNA hybrid docked (by computer) in the pocket of a 3.5 Å resolution structure derived from X-ray crystallography (Kohlstaedt et al. (1992) Science 256:1783-1790). The distance from the cluster of bases determined to be crucial to this interaction in the pseudoknot and the conserved bases in the extended ligand sequence is approximately 18 base-pairs as well. Accordingly, it is concluded that the pseudoknot interacts with the polymerase catalytic site—in that the ligand has been shown to bind HIV-RT deleted for the RNAse H domain—and that the evolved extension to the pseudoknot may interact with the RNAse H domain. In general the ligands tested from each of these motifs increase affinity of the ligand B sequence to HIV-RT by at least 10-fold.

VII. Elucidation of an Improved Nucleic Acid Ligand for HIV-1 Rev Protein

An example of the methods of the present invention are presented herein for the nucleic acid ligand for HIV-1 Rev protein. U.S. patent application Ser. No. 07/714,131, filed Jun. 10, 1991, entitled "Nucleic Acid Ligands," now issued as U.S. Pat. No. 5,475,096, describes the results obtained when SELEX was performed with the Rev target. Inspection of the nucleic acid sequences that were found to have a high affinity to Rev revealed a grouping of these sequences into three Motifs (I, II and III). Ligands of Motif I seemed to be a composite of the individual motifs described by Motifs II and III, and in general bound with higher affinity to Rev. One of the Motif I ligand sequences (Rev ligand sequence 6a (SEQ ID NO:40)) bound with significantly higher affinity than all of the ligands that were cloned and sequenced. As shown in FIG. 12, the 6a sequence is hypothesized to form a bulge between two helices with some base-pairing across this bulge.

Described herein are chemical modification experiments performed on ligand 6a designed to confirm the proposed secondary structure, find where binding of the Rev protein protects the ligand from chemical attack, and detect the nucleotides essential for Rev interaction. In addition, a secondary SELEX experiment was conducted with biased randomization of the 6a ligand sequence so as to more comprehensively describe a consensus for the highest affinity binding to the HIV-1 Rev protein.

Chemical modification of the Rev ligand. Chemical modification studies of the Rev ligand 6a were undertaken to determine its possible secondary structural elements, to find which modifications interfere with the binding of the ligand by Rev, to identify which positions are protected from modification upon protein binding, and to detect possible changes in ligand structure that occur upon binding.

The modifying chemicals include ethylnitrosourea (ENU) which modifies phosphates, dimethyl sulfate (DMS) which modifies the base-pairing positions N3 of C and N1 of adenine, kethoxal which modifies base-pairing positions N1 and N2 of guanine, carbodiimide (CMCT) which modifies base-paring position N3 of uracil and to a smaller extent the N1 position of guanine, and diethylpyrocarbonate (DEPC) which modifies the N7 position of adenine and to some extent also the N7 of guanine. ENU modification was assayed by modification-dependent hydrolysis of a labeled RNA chain, while all other modifying agents were used on an extended RNA ligand, with modified positions revealed by primer extension of an annealed oligonucleotide.

The chemical probing of the Rev ligand native structure is summarized in FIG. 13A. The computer predicted secondary structure (Zuker (1989) Science 244:48-52; Jaeger et al. (1989) Proc. Natl. Acad. Sci. USA 86:7706-7710) and native modification data are in general agreement; the ligand is composed of three helical regions, one four-base hairpin loop, and three "bulge" regions (see FIG. 13B for a definition of these structural "elements").

ENU modification of phosphates was unchanged for ligands under native and denaturing conditions, indicating no involvement of phosphate groups in the secondary or tertiary structure of the RNA. In general, all computer-predicted base-pairing regions are protected from modification. One exception is the slight modifications of N7 ($G^{10}$, $A^{11}$, $G^{12}$) in the central helix (normally a protected position in helices). These modifications are possibly a result of helical breathing; the absence of base-pairing face modifications in the central helix suggest that the N7 accessibility is due to small helical distortions rather than a complete, local unfolding of the RNA. The $G^{19}$-$U^{22}$ hairpin loop is fully modified, except for somewhat partial modification of $G^{19}$.

The most interesting regions in the native structure are the three "bulge" regions, $U^8$-$U^9$, $A^{13}$-$A^{14}$-$A^{15}$ and $G^{26}$-$A^{27}$. $U^8$-$U^9$ are fully modified by CMCT, possibly indicating base orientations into solvent. $A^{13}$, $A^{14}$ and $A^{15}$ are all modified by DMS and DEPC with the strongest modifications occurring on the central $A^{14}$. The bulge opposite to the $A^{13}$-$A^{15}$ region shows complete protection of $G^{26}$ and very slight modification of $A^{27}$ by DMS. One other investigation of Rev-binding RNAs (Bartel et al. (1991) Cell 67:529-536) has argued for the existence of A:A and A:G non canonical base pairing, corresponding in the present ligand to $A^{13}$:$A^{27}$ and $A^{15}$:$G^{26}$. These possibilities are not ruled out by this modification data, although the isosteric A:A base pair suggested by Bartel et al. would use the N1A positions for base-pairing and would thus be resistant to DMS treatment. Also, an A:G pair would likely use either a N1A or N7A for pairing, leaving the A resistant to DMS or DEPC.

Modification interference of Rev binding. The results of the modification interference studies is summarized in FIG.

14 (quantitative data on individual modifying agents is presented in FIGS. 15 through 19). In general, phosphate and base modification binding interference is clustered into two regions of the RNA ligand. To a first approximation, these regions correspond to two separate motifs present in the SELEX experiments that preceded this present study. Phosphate modification interference is probably the most suggestive of actual sites for ligand-protein contacts and constitutes an additional criterion for the grouping of the modification interference data into regions.

The first region is centered on $U^{24}$-$G^{25}$-$G^{26}$ and includes interference due to phosphate, base-pairing face and N7 modifications. These same three nucleotides, conserved in the wild-type RRE, were also found to be critical for Rev binding in a modification interference study using short RNAs containing the RRE IIB stem loop (Kjems et al. (1992) EMBO J. 11(3):1119-1129). The second region centers around $G^{10}$-$A^{11}$-$G^{12}$ with interference again from phosphate, base-pairing face and N7 modifications. Additionally, there is a smaller "mini-region" encompassing the stretch $C^6$-$A^7$-$U^8$, with phosphate and base-pairing face modifications interfering with binding.

Throughout the ligand, many base-pairing face modifications showed binding interference, most likely because of perturbations in the ligand's secondary structure. Two of the "bulge" bases, $U^9$ and $A^{14}$, did not exhibit modification interference, indicating that both have neither a role in specific base-pairing interactions/stacking nor in contacting the protein. Chemical modification protection when RNA is bound to Rev. The "footprinting" chemical modification data is summarized in FIG. 20. Four positions, $U^8$, $A^{13}$, $A^{15}$ and $A^{27}$, showed at least two-fold reduction in modification of base-pairing faces (and a like reduction in N7 modification for the A positions) while bound to Rev protein. The slight N7 modifications of $G^{10}$-$A^{11}$-$G^{12}$ under native conditions were not detected when the ligand was modified in the presence of Rev. $G^{32}$, unmodified in chemical probing of the RNA native structure, shows strong modification of its base-pairing face and the N7 position when complexed with Rev. $U^{31}$ and $U^{33}$, 5' and 3' of $G^{32}$, show slight CMCT modification when the ligand is bound to protein. Secondary SELEX using biased randomization of template. A template was synthesized as shown in FIG. 21 in which the Rev ligand 6a sequence was mixed with the other three nucleotides at each position in the ratio of 62.5 (for the 6a sequence) to 12.5 for each of the other three nucleotides. This biased template gave rise to RNAs with background affinity for Rev protein (Kd=$10^{-7}$). Six rounds of SELEX yielded the list of sequences shown in FIG. 21 (SEQ ID NOS:45-82). The frequency distribution of the nucleotides and base pairs found at each position as it differs from that expected from the input distribution during template synthesis is shown in FIGS. 22 and 23. A new consensus based on these data is shown in FIG. 24. The most significant differences from the sequence of Rev ligand 6a are replacement of the relatively weak base pair A7-U31 with a G-C pair and allowed or preferred substitution of U9 with C, A 14 with U, U22 with G. Absolutely conserved positions are at sites G10, A11, G12; A15, C16, A17; U24, G25; and C28, U29, C30. No bases were found substituted for G26 and A25, although there was one and three deletions found at those positions respectively. Two labeled transcripts were synthesized, one with a simple ligand 6a-like sequence, and one with substitutions by the significant preferences found in FIG. 24. These RNAs bound identically to Rev protein.

Most of the substitutions in the stem region increase its stability. There does not seem to be significant selection of stems of length longer than 5 base-pairs although this could be a selection for replicability (for ease of replication during the reverse transcription step of SELEX, for example). There is some scattered substitution of other nucleotides for U9 in the original SELEX reported in U.S. patent application Ser. No. 07/714,131, filed Jun. 10, 1991, entitled "Nucleic Acid Ligands," now issued as U.S. Pat. No. 5,475,096, but this experiment shows preferred substitution with C. Deletions of A27 also appeared in that original SELEX. A surprising result is the appearance of C18-A pairings in place of C 18-G23 at a high frequency.

The reason there may be preferences found in this experiment that do not improve measured binding affinity may lie in the differences in the binding reactions of SELEX and these binding assays. In SELEX a relatively concentrated pool of heterogeneous RNA sequences (flanked by the requisite fixed sequences) are bound to the protein. In binding assays low concentrations of homogeneous RNA sequence are bound. In SELEX there may be selection for more discriminating conformational certainty due to the increased probability of intermolecular and intramolecular contacts with other RNA sequences. In the therapeutic delivery of concentrated doses of RNA ligands and their modified homologs, these preferences found in secondary SELEXes may be relevant.

EXAMPLE I

Elucidation of Improved Nucleic Acid Ligand Solution For HIV-RT

RNA synthesis. In vitro transcription with oligonucleotide templates was conducted as described by (Milligan et al. (1987) Nucleic Acid Research 15:8783-8798). All synthetic nucleic acids were made on an Applied Biosystems model 394-08 DNA/RNA synthesizer using standard protocols. Deoxyribonucleotide phosphoramidites and DNA synthesis solvents and reagents were purchased from Applied Biosystems. Ribonucleotide and 2'-methoxy-ribonucleotide phosphoramidites were purchased from Glen Research Corporation. For mixed base positions, 0.1 M phosphoramidite solutions were mixed by volume to the proportions indicated. Base deprotection was carried out at 55° C. for 6 hours in 3:1 ammonium hydroxide:ethanol. t-Butyl-dimethylsilyl protecting groups were removed from the 2'-OH groups of synthetic RNAs by overnight treatment in tetrabutylammonium fluoride. The deprotected RNAs were then phenol extracted, ethanol precipitated and purified by gel electrophoresis.

Affinity assays with labeled RNA and HIV-RT. Model RNAs for refinement of the 5' and 3' boundaries and for determination of the effect of substitutions were labeled during transcription with T7 RNA polymerase as described in Tuerk et al. (1990) J. Mol. Biol. 213:749; Tuerk and Gold (1990) Science 249:505-510, except that $\alpha$-$^{32}$P-ATP was used, in reactions of 0.5 mM C, G and UTP with 0.05 mM ATP. Synthetic oligonucleotides and phosphatased transcripts (as in Tuerk et al. 1990) were kinased as described in Gauss et al. (1987) Mol. Gen. Genet. 206:24. All RNA-protein binding reactions were done in a "binding buffer" of 200 mM KOAc, 50 mM Tris-HCl pH 7.7, 10 mM dithiothreitol with exceptions noted for chemical protection experiments below. RNA and protein dilutions were mixed and stored on ice for 30 minutes then transferred to 37° C. for 5 minutes. In binding assays the reaction volume was 60 µL of which 50 µL was assayed. Each reaction was suctioned through a pre-wet (with binding buffer) nitrocellulose filter and rinsed with 3 ml of binding buffer after which it was dried and counted for assays or subjected to elution and assayed for chemical modification. In comparisons of binding affinity, results were plotted and the protein concentration at which half-maximal binding occurred (the approximate Kd in conditions of protein excess) was determined graphically.

Selection of modified RNAs by HIV-RT. Binding reactions were as above except that rather than to vary the amount of HIV-RT added to a reaction, the volume of reaction was increased in order to lower concentration. RNAs that were modified under denaturing conditions were selected at concentrations of 20, 4 and 0.8 nanomolar HIV-RT (in volumes of 1, 5 and 25 mls of binding buffer.) The amount of RNA added to each reaction was equivalent for each experiment (approximately 1-5 picomoles). RNA was eluted from filters as described in Tuerk et al. (1990) J. Mol. Biol. 213:749; Tuerk and Gold (1990) Science 249: 505-510, and assayed for modified positions. In each experiment a control was included in which unselected RNA was spotted on a filter, eluted and assayed for modified positions in parallel with the selected RNAs. Determinations of variation in chemical modification for selected versus unselected RNAs were made by visual inspection of exposed films of electrophoresed assay products with the following exceptions. The extent of modification interference by ENU was determined by densitometric scanning of films using an LKB laser densitomer. An index of modification interference (M.I.) at each position was calculated as follows:

$$M.I.=(O.D.\text{unselected}/O.D.\text{unselected } A20)/(O.D.\text{selected}/O.D.\text{selected } A20)$$

where the value at each position assayed for selected modified RNA (O.D.selected) is divided by that value for position A20 (O.D.selected A20) and divided into likewise normalized values for the unselected lane. All values of M.I. greater than 2.0 are reported as interfering and greater than 4.0 as were normalized as shown above but for position A17. In addition, determinations were done by laser densitometry as described below.

Chemical modification of RNA. A useful review of the types of chemical modifications of RNA and their specificities and methods of assay was done by Ehresmann et al. (1987) Nucleic Acids Research 15:9109-9128. Modification of RNA under native conditions was done at 200 mM KOAc, 50 mM Tris-HCl pH 7.7 at 37° C. with ethylnitrosourea (ENU) (⅕ dilution v/v of room temperature ENU-saturated ethanol) for 1-3 hours, dimethyl sulfate (DMS) (¹⁄₇₅₀-fold dilution v/v) for eight minutes, kethoxal (0.5 mg/ml) for eight minutes, carbodiimide (CMCT) (8 mg/ml) for 20 minutes, and diethyl pyrocarbonate (DEPC) (¹⁄₁₀ dilution v/v for native conditions or ¹⁄₁₀₀ dilution for denaturing conditions) for 45 minutes, and under the same conditions bound to HIV-RT with the addition of 1 mM DTT. The concentrations of modifying chemical reagent were identical for denaturing conditions (except where noted for DEPC); those conditions were 7M urea, 50 mM Tris-HCl pH 7.7, 1 mM EDTA at 90° C. for 1-5 minutes except during modification with ENU which was done in the absence of 7M urea.

Assay of chemical modification. Positions of chemical modification were assayed by reverse transcription for DMS, kethoxal and CMCT on the lengthened ligand B RNA, 5'-GGUCCGAAGUGCAACGGGAAAAUGCAC-UAUGAAAGAAUUUUA UAUCUCUAUUGAAAC-3' (SEQ ID NO:4) (the ligand B sequence is underlined), to which is annealed the oligonucleotide primer 5'-CCGGATC-CGTTTCAATAGAGATATA AAATTC-3' (SEQ ID NO:5); reverse transcription products (obtained as in Gauss et al. (1987) Mol. Gen. Genet. 206:24) were separated by electrophoresis on 10% polyacrylamide gels. Positions of ENU and DEPC modification were assayed as in Vlassov et al. (1980) FEBS 120:12-16 and Peattie and Gilbert (1980) Proc. Natl. Acad. Sci. USA 77:4679-4682, respectively (separated by electrophoresis on 20% polyacrylamide gels). Assay of 2'-methoxy ribose versus ribose at various positions was assayed by alkaline hydrolysis for 45 minutes at 90° C. in 50 mM sodium carbonate pH 9.0.

Modification of RNA in the presence of HIV-RT. Conditions were as for modification of native RNA. Concentrations of HIV-RT were approximately 10-fold excess over RNA concentration. In general protein concentrations ranged from 50 nM to 1 µM.

SELEX isolation of accessory contacts with HIV-RT. The starting RNA was transcribed from PCRd templates synthesized from the following oligonucleotides:

```
5'-GGGCAAGCTTTAATACGACTCACTATAGGTCCGAAGTGCAACGGGAAAATG-CAC    (SEQ ID NO:6)
T-3' (5' primer);

5'-GTTTCAATAGAGATATAAAATTCTTTCATAG-3' (3' primer);                (SEQ ID NO:7)

and

5'-GTTTCAATAGAGATATAAAATTCTTTCATAG-[30N]AGTGCATTTCCCGTTGC-ACT  (SEQ ID NO:8)
TCGGACC-3' (variable template).
``` strongly interfering. In determination of the effects of mixed substitution of 2'-methoxys for 2' hydroxyls (on the ribose at each nucleotide position) gels of electrophoresed hydrolysis products were counted on an Ambis detection system directly. The counts associated with each band within a lane SELEX was performed as described previously with HIV-RT with the following exceptions. The concentration of HIV-RT in the binding reaction of the first SELEX round was 13 nanomolar, RNA at 10 micromolar, in 4 ml of binding buffer, in the rounds 2 through 9 selection was done with 2.6 nanomolar HIV-RT, 1.8 micromolar RNA in 20 ml of buffer, in rounds 10-14 we used 1 nanomolar HIV-RT, 0.7 micromolar RNA in 50 ml, and for rounds 15 and 16 we used 0.5 nanomolar HIV-RT, 0.7 micromolar RNA in 50 ml of binding buffer.

Additional References to Example I:
  Moazed et al. (1986) J. Mol. Biol. 187:399-416.
  Roald et al. (1989) Science 246:1135.
  Tuerk et al. (1992) Proc. Natl. Acad. Sci. USA 89:6988-6992.

EXAMPLE II

Elucidation of Improved Nucleic Acid Ligand Solutions for HIV-1 Rev Protein

The Rev ligand sequence used for chemical modification is shown in FIG. 12 (the numbering scheme shown will be used hereinafter). RNA for modification was obtained from T7 RNA polymerase transcription of synthetic oligonucleotide templates. ENU modification was carried out on the ligand sequence as shown in FIG. 12A. DMS, kethoxal, CMCT, and DEPC modifications were carried out on a extended ligand sequence, and analyzed by reverse transcription with the synthetic oligonucleotide primer shown in FIG. 12B.

Chemical Modification of RNA. Chemical modification techniques for nucleic acids are described in general in Ehresmann et al. (1987) Nucleic Acids Research 15:9109-9128. Modification of RNA under native conditions was performed in 200 mM KOAc, 50 mM Tris-HCl pH 7.7, 1 mM EDTA at 37° C. Modification under denaturing conditions was done in 7 M urea, 50 mM Tris-HCl pH 7.7 at 90° C. Concentration of modifying agents and incubation times are as follows: ethylnitrosourea (ENU)—⅕ dilution v/v of ethanol saturated with ENU, native 1-3 hours, denaturing 5 minutes; dimethyl sulfate (DMS)—1/750-fold dilution v/v, native 8 minutes, denaturing 1 minute; kethoxal—0.5 mg/ml, native 5 minutes, denaturing 2 minutes; carbodiimide (CMCT)—10 mg/ml, native 30 minutes, denaturing 3 minutes; diethyl pyrocarbonate (DEPC)—1/10 dilution v/v, native 10 minutes, denaturing 1 minute.

Modification interference of Rev binding. RNAs chemically modified under denaturing conditions were selected for Rev binding through filter partitioning. Selections were carried out at Rev concentrations of 30, 6 and 1.2 nanomolar (in respective volumes of 1, 5 and 25 ml of binding buffer; 200 mM KOAc, 50 mM Tris-HCl pH 7.7, and 10 mM dithiothreitol). Approximately 3 picomoles of modified RNA were added to each protein solution, mixed and stored on ice for 15 minutes, and then transferred to 37° C. for 10 minutes. Binding solutions were passed through pre-wet nitrocellulose filters, and rinsed with 5 ml of binding buffer. RNA was eluted from the filters as described in Tuerk et al. (1990) Science 24:505-510 and assayed for modified positions that remained. Modified RNA was also spotted on filters and eluted to check for uniform recovery of modified RNA.

The extent of modification interference was determined by densitometric scanning of autoradiographs using LKB (ENU) and Molecular Dynamics (DMS, kethoxal, CMCT, and DEPC) laser densitometers. Values for modified phosphates and bases were normalized to a chosen modified position for both selected and unselected lanes; the values for the modified positions in the selected lane were then divided by the corresponding positions in the unselected lane (for specific normalizing positions see FIGS. 15-19). Values above 4.0 for modified bases and phosphates are designated as strongly interfering, and values above 2.0 are termed slightly interfering.

Modification of RNA in the presence of Rev. "Footprinting" of the Rev ligand, modification of the RNA ligand in the presence of Rev protein, was performed in 200 mM KOAc, 50 mM Tris-Cl pH 7.7, 1 mM DTT, and 5 mM $MgCl_2$. Concentration of protein was 500 nanomolar, and approximately in 3-fold molar excess over RNA concentration. Modification with protein present was attempted with all modifying agents listed above except ethylnitrosourea (ENU).

Assay of chemically modified RNA. Positions of ENU modification were detected as in Vlassov et al. (1980) FEBS 120:12-16, and separated by electrophoresis on 20% denaturing acrylamide gels. DMS, kethoxal, CMCT and DEPC were assayed by reverse transcription of the extended Rev ligand with a radiolabelled oligonucleotide primer (FIG. 12) and separated by electrophoresis on 8% denaturing acrylamide gels.

SELEX with biased randomization. The templates for in vitro transcription were prepared by PCR from the following oligonucleotides:

```
5'-CCCGGATCCTCTTTACCTCTGTGTGagatacagagtccacaaacgtgttc    (SEQ ID NO:9)

tcaatgcacccGGTCGGAAGGCCATCAATAGTCCC-3' (template oligo)

5'-CCGAAGCTTAATACGACTCACTATAGGGACTATTGATGGCCTTCCGACC-3'  (SEQ ID NO:10)

(5' primer)

5'-CCCGGATCCTCTTTACCTCTGTGTG-3' (3' primer)                (SEQ ID NO:11)
``` where the small case letters in the template oligo indicates that at each position that a mixture of reagents were used in synthesis by an amount of 62.5% of the small case letter, and 12.5% each of the other three nucleotides.

SELEX was conducted as described previously with the following exceptions. The concentration of HIV-1 Rev protein in the binding reactions of the first and second rounds was 7.2 nanomolar and the RNA 4 micromolar in a volume of 10 ml (of 200 mM potassium acetate, 50 mM Tris-HCl pH 7.7, 10 mM DTT). For rounds three through six the concentration of Rev protein was 1 nanomolar and the RNA 1 micromolar in 40 ml volume. HIV-1 Rev protein was purchased from American Biotechnologies, Inc.

We claim:

1. A method for modifying a nucleic acid ligand for a given target so that the modified ligand has at least one of the following improved properties:
    decreased size;
    improved stability;
    improved binding to the target;
    modification of biological activity of the target;
    resistance to clearance;
wherein said modifying comprises adding, removing or substituting nucleotide residues, wherein said residues may be chemically modified, and/or chemically modifying said nucleic acid ligand based on:
    (a) determining which nucleotides are crucial to the interaction with the target molecule;
    (b) chemical modification experiments; or
    (c) determining the structural conformation of said nucleic acid ligand; and
    (d) modifying said ligand based on said determinations made in steps a) through c).

2. A method according to claim 1 wherein (a), (b) or (c) comprises performing covariance analysis.

3. A method according to claim 1 wherein (a), (b) or (c) comprises determining which nucleotide residues are necessary for maintaining the three dimensional structure of the ligand.

4. A method according to claim 1 wherein (a), (b) or (c) comprises determining the positions of the ligand which are crucial to the bound structure of the ligand with the target.

5. A method according to claim 1 wherein (a), (b) or (c) comprises determining which nucleotide residues interact with the target.

6. A method according to claim 5 wherein (a), (b) or (c) comprises determining which nucleotide residues interact with the target to facilitate the formation of ligand-target binding pairs.

7. A method according to claim 5 wherein (a), (b) or (c) comprises determining which nucleotide residues are involved in proximal contacts with the target.

8. A method according to claim 1 wherein (a), (b) or (c) comprises determining the binding affinity of a modified ligand relative to the ligand before modification, where the modification is provided by nucleotide substitution in the ligand.

9. A method according to claim 1 wherein (a), (b) or (c) comprises determining the binding affinity of a modified ligand relative to the ligand before modification, where the modification is provided by the absence of one or more nucleotides of the ligand.

10. A method according to claim 1 wherein (a), (b) or (c) comprises determining the binding affinity of a chemically modified form of the ligand relative to the ligand before chemical modification.

11. A method according to claim 1 wherein (a), (b) or (c) comprises chemically modifying the ligand in the presence of the target, and determining which nucleotides of the ligand are not chemically modified.

12. A method according to claim 1 wherein (a), (b) or (c) comprises denaturing the ligand and chemically modifying both the denatured and non-denatured forms of the ligand, and determining which nucleic acid residues are modified in the denatured ligand that are not modified in the non-denatured ligand.

13. A method according to claim 1 wherein said modifying comprises truncation of the ligand.

14. A method according to claim 1 wherein said modifying comprises incorporation of a cross-linking agent to covalently link the ligand to the target.

15. A method according to claim 1 wherein said modifying produces a small molecule that mimics the structure of the initial ligand framework.

16. A method according to claim 1 wherein said modifying has the effect of increasing the in vivo stability of the ligand.

17. A method according to claim 1 wherein said modifying has the effect of enhancing or mediating the delivery of the ligand.

18. A method according to claim 1 wherein said modifying provides resistance to enzymatic or chemical degradation.

19. A method according to claim 1 wherein said modifying reduces the rate of clearance of the modified ligand from the body during therapy.

20. A method according to claim 1 wherein said modifying comprises chemical modification or derivatization of the ligand at the ribose and/or phosphate and/or base positions.

21. A method according to claim 1 wherein the chemical modification experiments (b) are performed using a chemical selected from:
ethylnitrosourea;
dimethyl sulfate;
carbodiimide;
diethylpyrocarbonate; and
kethoxal.

22. A method according to claim 1 wherein the target is selected from:
HIV-RT protein;
HIV-1 Rev protein;
Thrombin.

23. The method of claim 1 wherein said nucleic acid ligand has been obtained from a candidate mixture of nucleic acids by:
(1) contacting the candidate mixture with the target molecule, wherein nucleic acids having an increased affinity to the target relative to the candidate mixture may be partitioned from the remainder of the candidate mixture;
(2) partitioning the increased affinity nucleic acids from the remainder of the candidate mixture;
(3) amplifying the increased affinity nucleic acids to yield a ligand-enriched mixture of nucleic acids; and
(4) repeating steps (1)-(3) as necessary to identify a nucleic acid ligand, wherein the ligand-enriched mixture of nucleic acids produced in step (3) is used as the candidate mixture in step (1).

24. A method according to claim 1 wherein the modified ligand is a single stranded nucleic acid.

25. A method according to claim 1 wherein the modified ligand is an RNA or DNA.

26. A method according to claim 1 wherein the modified ligand is an RNA and said ligand modification includes a substitution on ribose of 2'-methoxy for 2'-hydroxyl.

27. A method according to claim 1 wherein the modified ligand is an RNA and said ligand modification includes modification of certain riboses to contain 2'-$NH_2$.

28. A method for modifying a nucleic acid ligand for a given target, such target being a three dimensional chemical structure other than a polynucleotide that binds to said nucleic acid ligand through a mechanism which predominantly depends on Watson/Crick base pairing, wherein said nucleic acid ligand is not a nucleic acid having the known physiological function of being bound by the target so that the modified ligand has at least one of the following improved properties:
decreased size;
improved stability;
improved binding to the target;
modification of biological activity of the target;
capability to cross tissue or cell membrane barriers;
resistance to clearance;
wherein said modifying comprises adding, removing or substituting nucleotide residues, wherein said residues may be chemically modified, and/or chemically modifying said nucleic acid ligand based on:
(a) determining which nucleotides are crucial to the interaction with the target molecule;
(b) chemical modification experiments; or
(c) determining the structural conformation of said nucleic acid ligand; and
(d) modifying said ligand based on said determinations made in steps a) through c).

29. The method according to claim 28 wherein (a), (b) or (c) comprises performing covariance analysis.

30. The method according to claim 28 wherein (a), (b) or (c) comprises determining which nucleotide residues are necessary for maintaining the three dimensional structure of the ligand.

31. The method according to claim 28 wherein (a), (b) or (c) comprises determining the positions of the ligand which are crucial to the bound structure of the ligand with the target.

32. The method according to claim 28 wherein (a), (b)or (c) comprises determining which nucleotide residues interact with the target.

33. The method according to claim 28 wherein (a), (b) or (c) comprises determining which nucleotide residues interact with the target to facilitate the formation of ligand-target binding pairs.

34. The method according to claim 33 wherein (a), (b) or (c) comprises determining which nucleotide residues are involved in proximal contacts with the target.

35. The method according to claim 28 wherein (a), (b) or (c) comprises determining the binding affinity of a modified ligand relative to the ligand before modification, where the modification is provided by nucleotide substitution in the ligand.

36. The method according to claim 28 wherein (a), (b) or (c) comprises determining the binding affinity of a modified ligand relative to the ligand before modification, where the modification is provided by the absence of one or more nucleotides of the ligand.

37. The method according to claim 28 wherein (a), (b) or (c) comprises determining the binding affinity of a chemically modified form of the ligand relative to the ligand before chemical modification.

38. The method according to claim 28 wherein (a), (b) or (c) comprises chemically modifying the ligand in the presence of the target, and determining which nucleotides of the ligand are not chemically modified.

39. The method according to claim 28 wherein (a), (b) or (c) comprises denaturing the ligand and chemically modifying both the denatured and non-denatured forms of the ligand, and determining which nucleic acid residues are modified in the denatured ligand that are not modified in the non-denatured ligand.

40. A method according to claim 28 wherein said modifying comprises truncation of the ligand.

41. The method according to claim 28 wherein said ligand modifying comprises incorporation of a cross-linking agent to covalently link the ligand to the target.

42. The method according to claim 28 wherein said modifying produces a small molecule that mimics the structure of the initial ligand framework.

43. The method according to claim 28 wherein said modifying has the effect of enhancing or mediating the delivery of the ligand.

44. The method according to claim 28 wherein said ligand modification provides resistance to enzymatic or chemical degradation.

45. The method according to 28 wherein said ligand modifying comprises chemical modification or derivatization of the ligand at the ribose and/or phosphate and/or base positions.

46. The method according to claim 28 wherein said modifying has the effect of increasing the in vivo stability of the ligand.

47. A method according to claim 28 wherein said modifying reduces the rate of clearance of the modified ligand from the body during therapy.

48. The method according to claim 28 wherein the chemical modification experiments (b) are performed using a chemical selected from:
ethylnitrosourea;
dimethyl sulfate;
carbodiimide;
diethylpyrocarbonate; and
kethoxal.

49. The method according to claim 28 wherein the target is selected from:
HIV-RT protein;
HIV-1 Rev protein; or
Thrombin.

50. The method of claim 28 wherein said nucleic acid ligand has been obtained from a candidate mixture of nucleic acids by:
(1) contacting the candidate mixture with the target molecule, wherein nucleic acids having an increased affinity to the target relative to the candidate mixture may be partitioned from the remainder of the candidate mixture;
(2) partitioning the increased affinity nucleic acids from the remainder of the candidate mixture;
(3) amplifying the increased affinity nucleic acids to yield a ligand-enriched mixture of nucleic acids; and
(4) repeating steps (1)-(3) as necessary to identify a nucleic acid ligand, wherein the ligand-enriched mixture of nucleic acids produced in step (3) is used as the candidate mixture in step (1).

51. The method according to claim 28 wherein the modified ligand is a single stranded nucleic acid.

52. A method according to claim 28 wherein the modified ligand is an RNA or DNA.

53. The method according to claim 28 wherein the modified ligand is an RNA and said ligand modification includes a substitution on ribose of 2'-methoxy for 2'-hydroxyl.

54. The method according to claim 28 wherein the modified ligand is an RNA and said modifying comprises a 2' substitution on ribose.

55. The method according to claim 28 wherein the modified ligand is an RNA and said ligand modification includes modification of certain riboses to contain 2'-$NH_2$.

56. The method according to claim 1 wherein the modified ligand is an RNA and said modifying comprises a 2' substitution on ribose.

* * * * *